US009005195B2

(12) United States Patent
Mayse et al.

(10) Patent No.: US 9,005,195 B2
(45) Date of Patent: *Apr. 14, 2015

(54) DELIVERY DEVICES WITH COOLABLE ENERGY EMITTING ASSEMBLIES

(75) Inventors: Martin L. Mayse, Wayzata, MN (US); Steven C. Dimmer, Bellevue, WA (US)

(73) Assignee: Holaira, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,529

(22) Filed: Sep. 26, 2011

(65) Prior Publication Data

US 2012/0016363 A1 Jan. 19, 2012

Related U.S. Application Data

(63) Continuation of application No. 12/913,702, filed on Oct. 27, 2010.

(60) Provisional application No. 61/255,367, filed on Oct. 27, 2009, provisional application No. 61/260,348, filed on Nov. 11, 2009.

(51) Int. Cl.
| | |
|---|---|
| *A61B 18/14* | (2006.01) |
| *A61B 1/267* | (2006.01) |
| *A61B 18/18* | (2006.01) |
| *A61B 17/32* | (2006.01) |

(Continued)

(52) U.S. Cl.
CPC ............ *A61B 1/2676* (2013.01); *A61B 18/1492* (2013.01); *A61B 2018/00023* (2013.01); *A61B 2018/00214* (2013.01); *A61B 2018/0022* (2013.01); *A61B 2018/00541* (2013.01); *A61B 2018/0212* (2013.01); *A61B 2018/0262* (2013.01); *A61B 18/18* (2013.01); *A61B 18/1815* (2013.01); *A61B 18/1485* (2013.01); *A61B 17/320068* (2013.01)

(58) Field of Classification Search
USPC ............... 606/42, 47, 41; 607/42, 98, 99, 115
See application file for complete search history.

(56) References Cited

U.S. PATENT DOCUMENTS

| | | | |
|---|---|---|---|
| 612,724 A | 10/1898 | Hamilton | |
| 1,155,169 A | 9/1915 | Starkweather | |
| 1,207,479 A | 12/1916 | Bisgaard | |

(Continued)

FOREIGN PATENT DOCUMENTS

| | | |
|---|---|---|
| CA | 2419228 | 8/2004 |
| CN | 101115448 B | 5/2010 |

(Continued)

OTHER PUBLICATIONS

Abbott, "Present Concepts Relative to Autonomic Nerve Surgery in the Treatment of Pulmonary Disease," *American Journal of Surgery* 90:479-489, 1955.

(Continued)

*Primary Examiner* — Michael Peffley
*Assistant Examiner* — Thomas Giuliani
(74) *Attorney, Agent, or Firm* — Patterson Thuente Pedersen, P.A.

(57) ABSTRACT

Systems, delivery devices, and methods to treat to ablate, damage, or otherwise affect tissue. The treatment systems are capable of delivering a coolable ablation assembly that ablates targeted tissue without damaging non-targeted tissue. The coolable ablation assembly damages nerve tissue to temporarily or permanently decrease nervous system input.

27 Claims, 54 Drawing Sheets

(51) Int. Cl.
*A61B 18/00* (2006.01)
*A61B 18/02* (2006.01)

(56) References Cited

U.S. PATENT DOCUMENTS

| | | | |
|---|---|---|---|
| 1,216,183 A | 2/1917 | Swingle | |
| 1,695,107 A | 12/1928 | Kahl | |
| 2,072,346 A | 3/1937 | Smith | |
| 2,279,714 A | 4/1942 | Meyerhof et al. | |
| 3,320,957 A | 5/1967 | Sokolik | |
| 3,568,659 A | 3/1971 | Karnegis | |
| 3,667,476 A | 6/1972 | Muller | |
| 3,692,029 A | 9/1972 | Adair | |
| 3,918,449 A | 11/1975 | Pistor | 128/218 R |
| 3,946,745 A | 3/1976 | Hsiang-Lai et al. | 128/421 |
| 3,949,743 A | 4/1976 | Shanbrom | 128/173.1 |
| 3,995,617 A | 12/1976 | Watkins et al. | |
| 4,078,864 A | 3/1978 | Howell | |
| 4,095,602 A | 6/1978 | LeVeen | |
| 4,116,589 A | 9/1978 | Rishton | |
| 4,129,129 A | 12/1978 | Amrine | |
| 4,154,246 A | 5/1979 | LeVeen | |
| 4,277,168 A | 7/1981 | Oku | |
| 4,305,402 A | 12/1981 | Katims | 128/741 |
| 4,351,330 A | 9/1982 | Scarberry | 128/207.15 |
| 4,461,283 A | 7/1984 | Doi | |
| 4,502,490 A | 3/1985 | Evans et al. | |
| 4,503,855 A | 3/1985 | Maslanka | |
| 4,503,863 A | 3/1985 | Katims | 128/741 |
| 4,512,762 A | 4/1985 | Spears | |
| 4,522,212 A | 6/1985 | Gelinas et al. | |
| 4,557,272 A | 12/1985 | Carr | |
| 4,565,200 A | 1/1986 | Cosman | 128/642 |
| 4,567,882 A | 2/1986 | Heller | |
| 4,573,481 A | 3/1986 | Bullara | 128/784 |
| 4,584,998 A | 4/1986 | McGrail | |
| 4,612,934 A | 9/1986 | Borkan | |
| 4,621,642 A | 11/1986 | Chen | |
| 4,621,882 A | 11/1986 | Krumme | |
| 4,625,712 A | 12/1986 | Wampler | |
| 4,643,186 A | 2/1987 | Rosen et al. | 128/303.1 |
| 4,646,737 A | 3/1987 | Hussein et al. | |
| 4,649,924 A | 3/1987 | Taccardi | |
| 4,649,935 A | 3/1987 | Charmillot et al. | 128/783 |
| 4,658,836 A | 4/1987 | Turner | 128/804 |
| 4,674,497 A | 6/1987 | Ogasawara | |
| 4,683,890 A | 8/1987 | Hewson | |
| 4,704,121 A | 11/1987 | Moise | |
| 4,706,688 A | 11/1987 | Don Michael et al. | |
| 4,709,698 A | 12/1987 | Johnston et al. | |
| 4,739,759 A | 4/1988 | Rexroth et al. | |
| 4,754,065 A | 6/1988 | Levenson et al. | |
| 4,754,752 A | 7/1988 | Ginsburg et al. | |
| 4,765,322 A | 8/1988 | Charmillot et al. | 128/783 |
| 4,765,959 A | 8/1988 | Fukasawa | |
| 4,767,402 A | 8/1988 | Kost et al. | 604/22 |
| 4,772,112 A | 9/1988 | Zider et al. | |
| 4,773,899 A | 9/1988 | Spears | |
| 4,779,614 A | 10/1988 | Moise | |
| 4,784,135 A | 11/1988 | Blum et al. | |
| 4,790,305 A | 12/1988 | Zoltan et al. | |
| 4,799,479 A | 1/1989 | Spears | |
| 4,802,492 A | 2/1989 | Grunstein | |
| 4,808,164 A | 2/1989 | Hess | 604/95 |
| 4,817,586 A | 4/1989 | Wampler | |
| 4,825,871 A | 5/1989 | Cansell | |
| 4,827,935 A | 5/1989 | Geddes et al. | |
| 4,846,152 A | 7/1989 | Wampler et al. | |
| 4,862,886 A | 9/1989 | Clarke et al. | |
| 4,881,542 A | 11/1989 | Schmidt et al. | 128/207.14 |
| 4,895,557 A | 1/1990 | Moise et al. | |
| 4,902,129 A | 2/1990 | Siegmund et al. | |
| 4,904,472 A | 2/1990 | Belardinelli et al. | 514/263 |
| 4,906,229 A | 3/1990 | Wampler | |
| 4,907,589 A | 3/1990 | Cosman | |
| 4,908,012 A | 3/1990 | Moise et al. | |
| 4,920,978 A | 5/1990 | Colvin | |
| 4,944,722 A | 7/1990 | Carriker et al. | |
| 4,945,910 A | 8/1990 | Budyko et al. | 128/421 |
| 4,955,377 A | 9/1990 | Lennox et al. | 128/401 |
| 4,967,765 A | 11/1990 | Turner et al. | |
| 4,969,865 A | 11/1990 | Hwang et al. | |
| 4,976,709 A | 12/1990 | Sand | |
| 4,976,710 A | 12/1990 | Mackin | |
| 4,985,014 A | 1/1991 | Orejola | |
| 4,989,604 A | 2/1991 | Fang | 128/421 |
| 4,991,603 A | 2/1991 | Cohen et al. | |
| 4,992,474 A | 2/1991 | Skidmore et al. | 514/653 |
| 5,005,559 A | 4/1991 | Blanco et al. | |
| 5,007,908 A | 4/1991 | Rydell | 606/47 |
| 5,009,636 A | 4/1991 | Wortley et al. | |
| 5,009,936 A | 4/1991 | Yamanaka et al. | |
| 5,010,892 A | 4/1991 | Colvin et al. | |
| 5,019,075 A | 5/1991 | Spears et al. | |
| 5,027,829 A | 7/1991 | Larsen | |
| 5,030,645 A | 7/1991 | Kollonitsch | |
| 5,036,848 A | 8/1991 | Hewson | |
| 5,053,033 A | 10/1991 | Clarke | |
| 5,054,486 A | 10/1991 | Yamada | 128/421 |
| 5,056,519 A | 10/1991 | Vince | |
| 5,056,529 A | 10/1991 | de Groot | 128/754 |
| 5,057,107 A | 10/1991 | Parins et al. | 606/48 |
| 5,074,860 A | 12/1991 | Gregory et al. | |
| 5,078,716 A | 1/1992 | Doll | |
| 5,084,044 A | 1/1992 | Quint | |
| 5,096,916 A | 3/1992 | Skupin | |
| 5,100,388 A | 3/1992 | Behl et al. | |
| 5,100,423 A | 3/1992 | Fearnot | |
| 5,103,804 A | 4/1992 | Abele et al. | |
| 5,105,826 A | 4/1992 | Smits et al. | |
| 5,106,360 A | 4/1992 | Ishiwara et al. | |
| 5,107,830 A | 4/1992 | Younes | |
| 5,107,835 A | 4/1992 | Thomas | 128/419 R |
| 5,109,846 A | 5/1992 | Thomas | 128/421 |
| 5,114,423 A | 5/1992 | Kasprzyk et al. | |
| 5,116,864 A | 5/1992 | March et al. | |
| 5,117,828 A | 6/1992 | Metzger et al. | 128/642 |
| 5,123,413 A | 6/1992 | Hasegawa et al. | 128/419 G |
| 5,126,375 A | 6/1992 | Skidmore et al. | 514/651 |
| 5,135,480 A | 8/1992 | Bannon et al. | 604/20 |
| 5,135,517 A | 8/1992 | McCoy | |
| 5,139,029 A | 8/1992 | Fishman et al. | 128/743 |
| 5,151,100 A | 9/1992 | Abele et al. | 606/28 |
| 5,152,286 A | 10/1992 | Sitko et al. | 128/422 |
| 5,158,536 A | 10/1992 | Sekins | |
| 5,165,420 A | 11/1992 | Strickland | |
| 5,167,223 A | 12/1992 | Koros et al. | |
| 5,170,802 A | 12/1992 | Mehra | |
| 5,170,803 A | 12/1992 | Hewson et al. | |
| 5,174,288 A | 12/1992 | Bardy et al. | |
| 5,188,602 A | 2/1993 | Nichols | |
| 5,190,540 A | 3/1993 | Lee | 606/28 |
| 5,191,883 A | 3/1993 | Lennox et al. | |
| 5,213,576 A | 5/1993 | Abiuso et al. | |
| 5,215,103 A | 6/1993 | Desai | |
| 5,224,491 A | 7/1993 | Mehra | |
| 5,225,445 A | 7/1993 | Skidmore et al. | 514/651 |
| 5,231,996 A | 8/1993 | Bardy et al. | |
| 5,232,444 A | 8/1993 | Just et al. | |
| 5,234,456 A | 8/1993 | Silvestrini | |
| 5,239,982 A | 8/1993 | Trauthen | |
| 5,254,088 A | 10/1993 | Lundquist et al. | |
| 5,255,678 A | 10/1993 | Deslauriers et al. | |
| 5,255,679 A | 10/1993 | Imran | |
| 5,265,604 A | 11/1993 | Vince | |
| 5,269,758 A | 12/1993 | Taheri | |
| 5,281,218 A | 1/1994 | Imran | |
| 5,286,254 A | 2/1994 | Shapland et al. | 604/21 |
| 5,292,331 A | 3/1994 | Boneau | |
| 5,293,869 A | 3/1994 | Edwards et al. | |
| 5,309,910 A | 5/1994 | Edwards et al. | |
| 5,311,866 A | 5/1994 | Kagan et al. | |
| 5,313,943 A | 5/1994 | Houser et al. | |
| 5,324,255 A | 6/1994 | Passafaro et al. | 604/22 |

(56) References Cited

U.S. PATENT DOCUMENTS

| | | | |
|---|---|---|---|
| 5,324,284 A | 6/1994 | Imran | |
| 5,343,936 A | 9/1994 | Beatenbough et al. | |
| 5,344,398 A | 9/1994 | Hara | 604/96 |
| 5,345,936 A | 9/1994 | Pomeranz et al. | |
| 5,348,554 A | 9/1994 | Imran et al. | 606/41 |
| 5,366,443 A | 11/1994 | Eggers et al. | |
| 5,368,591 A | 11/1994 | Lennox et al. | |
| 5,370,644 A | 12/1994 | Langberg | |
| 5,370,675 A | 12/1994 | Edwards et al. | 607/101 |
| 5,370,679 A | 12/1994 | Atlee, III | |
| 5,372,603 A | 12/1994 | Acker et al. | 606/194 |
| 5,374,287 A | 12/1994 | Rubin | |
| 5,379,765 A | 1/1995 | Kajiwara et al. | |
| 5,383,917 A | 1/1995 | Desai et al. | |
| 5,393,207 A | 2/1995 | Maher et al. | |
| 5,394,880 A | 3/1995 | Atlee, III | |
| 5,396,887 A | 3/1995 | Imran | |
| 5,400,778 A | 3/1995 | Jonson et al. | |
| 5,400,783 A | 3/1995 | Pomeranz et al. | |
| 5,405,362 A | 4/1995 | Kramer et al. | 607/5 |
| 5,405,366 A | 4/1995 | Fox et al. | 607/50 |
| 5,409,483 A | 4/1995 | Campbell et al. | |
| 5,411,025 A | 5/1995 | Webster, Jr. | |
| 5,415,166 A | 5/1995 | Imran | |
| 5,415,656 A | 5/1995 | Tihon et al. | |
| 5,417,687 A | 5/1995 | Nardella et al. | |
| 5,422,362 A | 6/1995 | Vincent et al. | |
| 5,423,744 A | 6/1995 | Gencheff et al. | |
| 5,423,811 A | 6/1995 | Imran et al. | |
| 5,425,023 A | 6/1995 | Haraguchi et al. | |
| 5,425,703 A | 6/1995 | Feiring | |
| 5,425,811 A | 6/1995 | Mashita | |
| 5,431,696 A | 7/1995 | Atlee, III | |
| 5,433,730 A | 7/1995 | Alt | |
| 5,437,665 A | 8/1995 | Munro | |
| 5,443,470 A | 8/1995 | Stern et al. | |
| 5,454,782 A | 10/1995 | Perkins | |
| 5,454,840 A | 10/1995 | Krakovsky et al. | 607/39 |
| 5,456,667 A | 10/1995 | Ham et al. | |
| 5,458,596 A | 10/1995 | Lax et al. | |
| 5,465,717 A | 11/1995 | Imran et al. | |
| 5,470,352 A | 11/1995 | Rappaport | |
| 5,471,982 A | 12/1995 | Edwards et al. | |
| 5,474,530 A | 12/1995 | Passafaro et al. | |
| 5,478,309 A | 12/1995 | Sweezer et al. | |
| 5,478,578 A | 12/1995 | Arnold et al. | 424/499 |
| 5,496,271 A | 3/1996 | Burton et al. | 604/54 |
| 5,496,304 A | 3/1996 | Chasan | 606/1 |
| 5,496,311 A | 3/1996 | Abele et al. | |
| 5,496,312 A | 3/1996 | Klicek | |
| 5,500,011 A | 3/1996 | Desai | |
| 5,505,728 A | 4/1996 | Ellman et al. | |
| 5,505,730 A | 4/1996 | Edwards | |
| 5,507,791 A | 4/1996 | Sitko | |
| 5,509,419 A | 4/1996 | Edwards et al. | |
| 5,522,862 A | 6/1996 | Testerman et al. | |
| 5,531,779 A | 7/1996 | Dahl et al. | |
| 5,540,681 A | 7/1996 | Strul et al. | |
| 5,540,730 A | 7/1996 | Terry, Jr. et al. | 607/40 |
| 5,545,161 A | 8/1996 | Imran | |
| 5,545,193 A | 8/1996 | Fleischman et al. | |
| 5,547,469 A | 8/1996 | Rowland et al. | |
| 5,549,559 A | 8/1996 | Eshel | |
| 5,549,655 A | 8/1996 | Erickson | |
| 5,549,661 A | 8/1996 | Kordis et al. | |
| RE35,330 E | 9/1996 | Malone et al. | |
| 5,553,611 A | 9/1996 | Budd et al. | |
| 5,558,073 A | 9/1996 | Pomeranz et al. | |
| 5,562,608 A | 10/1996 | Sekins et al. | 604/20 |
| 5,571,074 A | 11/1996 | Buckman, Jr. et al. | |
| 5,571,088 A | 11/1996 | Lennox et al. | 604/96 |
| 5,574,059 A | 11/1996 | Regunathan et al. | |
| 5,578,072 A | 11/1996 | Barone et al. | |
| 5,582,609 A | 12/1996 | Swanson et al. | |
| 5,588,432 A | 12/1996 | Crowley | |
| 5,588,812 A | 12/1996 | Taylor et al. | |
| 5,595,183 A | 1/1997 | Swanson et al. | |
| 5,598,848 A | 2/1997 | Swanson et al. | |
| 5,599,345 A | 2/1997 | Edwards et al. | |
| 5,601,088 A | 2/1997 | Swanson et al. | |
| 5,605,157 A | 2/1997 | Panescu et al. | |
| 5,607,419 A | 3/1997 | Amplatz et al. | |
| 5,607,462 A | 3/1997 | Imran | |
| 5,620,438 A | 4/1997 | Amplatz et al. | |
| 5,620,463 A | 4/1997 | Drolet | 607/3 |
| 5,623,940 A | 4/1997 | Daikuzono | |
| 5,624,392 A | 4/1997 | Saab | |
| 5,624,439 A | 4/1997 | Edwards et al. | |
| 5,626,618 A | 5/1997 | Ward et al. | |
| 5,630,425 A | 5/1997 | Panescu et al. | |
| 5,630,794 A | 5/1997 | Lax et al. | |
| 5,630,813 A | 5/1997 | Kieturakis | |
| 5,634,471 A | 6/1997 | Fairfax et al. | |
| 5,641,326 A | 6/1997 | Adams | |
| 5,647,870 A | 7/1997 | Kordis et al. | |
| 5,658,278 A | 8/1997 | Imran et al. | 606/41 |
| 5,658,322 A | 8/1997 | Fleming | 607/50 |
| 5,658,549 A | 8/1997 | Akehurst et al. | 424/45 |
| 5,660,175 A | 8/1997 | Dayal | 128/207.15 |
| 5,662,108 A | 9/1997 | Budd et al. | |
| 5,669,930 A | 9/1997 | Igarashi | |
| 5,669,932 A | 9/1997 | Fischell et al. | |
| 5,674,472 A | 10/1997 | Akehurst et al. | 424/45 |
| 5,678,535 A | 10/1997 | Di Marco | |
| 5,680,860 A | 10/1997 | Imran | |
| 5,681,280 A | 10/1997 | Rusk et al. | |
| 5,681,308 A | 10/1997 | Edwards et al. | |
| 5,687,723 A | 11/1997 | Avitall | |
| 5,688,267 A | 11/1997 | Panescu et al. | |
| 5,690,692 A | 11/1997 | Fleming | 607/50 |
| 5,693,078 A | 12/1997 | Desai et al. | |
| 5,694,934 A | 12/1997 | Edelman | |
| 5,695,471 A | 12/1997 | Wampler | |
| 5,699,799 A | 12/1997 | Xu et al. | |
| 5,702,386 A | 12/1997 | Stern et al. | |
| 5,707,218 A | 1/1998 | Maher et al. | |
| 5,707,336 A | 1/1998 | Rubin | |
| 5,707,352 A | 1/1998 | Sekins et al. | |
| 5,707,400 A | 1/1998 | Terry, Jr. et al. | 607/44 |
| 5,722,401 A | 3/1998 | Pietroski et al. | |
| 5,722,403 A | 3/1998 | McGee et al. | |
| 5,722,416 A | 3/1998 | Swanson et al. | |
| 5,725,525 A | 3/1998 | Kordis | |
| 5,727,569 A | 3/1998 | Benetti et al. | |
| 5,728,094 A | 3/1998 | Edwards | |
| 5,730,128 A | 3/1998 | Pomeranz et al. | |
| 5,730,704 A | 3/1998 | Avitall | |
| 5,730,726 A | 3/1998 | Klingenstein | |
| 5,730,741 A | 3/1998 | Horzewski et al. | |
| 5,733,316 A | 3/1998 | Tierney et al. | |
| 5,733,319 A | 3/1998 | Neilson et al. | |
| 5,735,846 A | 4/1998 | Panescu et al. | |
| 5,740,808 A | 4/1998 | Panescu et al. | |
| 5,741,248 A | 4/1998 | Stern et al. | |
| 5,746,224 A | 5/1998 | Edwards | |
| 5,752,518 A | 5/1998 | McGee et al. | |
| 5,755,714 A | 5/1998 | Murphy-Chutorian | |
| 5,755,753 A | 5/1998 | Knowlton | |
| 5,759,158 A | 6/1998 | Swanson | |
| 5,765,568 A | 6/1998 | Sweezer, Jr. et al. | |
| 5,766,605 A | 6/1998 | Sanders et al. | 424/239.1 |
| 5,769,846 A | 6/1998 | Edwards et al. | |
| 5,772,590 A | 6/1998 | Webster, Jr. | |
| 5,779,669 A | 7/1998 | Haissaguerre et al. | |
| 5,779,698 A | 7/1998 | Clayman et al. | |
| 5,782,239 A | 7/1998 | Webster, Jr. | |
| 5,782,797 A | 7/1998 | Schweich, Jr. et al. | |
| 5,782,827 A | 7/1998 | Gough et al. | |
| 5,782,848 A | 7/1998 | Lennox | |
| 5,782,899 A | 7/1998 | Imran | |
| 5,792,064 A | 8/1998 | Panescu et al. | |
| 5,795,303 A | 8/1998 | Swanson et al. | |
| 5,800,375 A | 9/1998 | Sweezer et al. | |
| 5,800,486 A | 9/1998 | Thome et al. | 607/105 |

(56) References Cited

U.S. PATENT DOCUMENTS

| | | | |
|---|---|---|---|
| 5,807,306 A | 9/1998 | Shapland et al. | |
| 5,810,757 A | 9/1998 | Sweezer, Jr. et al. | |
| 5,810,807 A | 9/1998 | Ganz et al. | |
| 5,814,078 A | 9/1998 | Zhou et al. | 607/1 |
| 5,817,028 A | 10/1998 | Anderson | |
| 5,817,073 A | 10/1998 | Krespi | |
| 5,820,554 A | 10/1998 | Davis et al. | |
| 5,820,589 A | 10/1998 | Torgerson et al. | 604/93 |
| 5,823,189 A | 10/1998 | Kordis | |
| 5,827,277 A | 10/1998 | Edwards | |
| 5,833,651 A | 11/1998 | Donovan et al. | |
| 5,836,874 A | 11/1998 | Swanson et al. | |
| 5,836,905 A | 11/1998 | Lemelson et al. | |
| 5,836,947 A | 11/1998 | Fleischman et al. | |
| 5,837,001 A | 11/1998 | Mackey | |
| 5,843,075 A | 12/1998 | Taylor | |
| 5,843,077 A | 12/1998 | Edwards | |
| 5,843,088 A | 12/1998 | Barra et al. | 606/108 |
| 5,846,238 A | 12/1998 | Jackson et al. | |
| 5,848,969 A | 12/1998 | Panescu et al. | |
| 5,848,972 A | 12/1998 | Triedman et al. | |
| 5,849,026 A | 12/1998 | Zhou et al. | 607/90 |
| 5,855,577 A | 1/1999 | Murphy-Chutorian et al. | |
| 5,860,974 A * | 1/1999 | Abele | 606/41 |
| 5,863,291 A | 1/1999 | Schaer | |
| 5,865,791 A | 2/1999 | Whayne et al. | |
| 5,868,740 A | 2/1999 | LeVeen et al. | |
| 5,871,443 A | 2/1999 | Edwards et al. | |
| 5,871,483 A | 2/1999 | Jackson et al. | |
| 5,871,523 A | 2/1999 | Fleischman et al. | |
| 5,873,852 A | 2/1999 | Vigil et al. | |
| 5,873,865 A | 2/1999 | Horzewski et al. | |
| 5,876,340 A | 3/1999 | Tu et al. | |
| 5,876,399 A | 3/1999 | Chia et al. | |
| 5,881,727 A | 3/1999 | Edwards | |
| 5,882,346 A | 3/1999 | Pomeranz et al. | |
| 5,891,027 A | 4/1999 | Tu et al. | 600/374 |
| 5,891,135 A | 4/1999 | Jackson et al. | |
| 5,891,136 A | 4/1999 | McGee et al. | |
| 5,891,138 A | 4/1999 | Tu et al. | |
| 5,891,182 A | 4/1999 | Fleming | 607/50 |
| 5,893,847 A | 4/1999 | Kordis | |
| 5,893,887 A | 4/1999 | Jayaraman | |
| 5,897,554 A | 4/1999 | Chia et al. | |
| 5,899,882 A | 5/1999 | Waksman et al. | |
| 5,902,268 A * | 5/1999 | Saab | 604/96.01 |
| 5,904,651 A | 5/1999 | Swanson et al. | |
| 5,904,711 A | 5/1999 | Flom et al. | |
| 5,906,636 A | 5/1999 | Casscells, III et al. | |
| 5,908,445 A | 6/1999 | Whayne et al. | |
| 5,908,446 A | 6/1999 | Imran | |
| 5,908,839 A | 6/1999 | Levitt et al. | |
| 5,911,218 A | 6/1999 | DiMarco | 128/200.24 |
| 5,916,235 A | 6/1999 | Guglielmi | |
| 5,919,147 A | 7/1999 | Jain | |
| 5,919,172 A | 7/1999 | Golba, Jr. | |
| 5,924,424 A | 7/1999 | Stevens et al. | |
| 5,928,228 A | 7/1999 | Kordis et al. | |
| 5,931,806 A | 8/1999 | Shimada | 604/24 |
| 5,931,835 A | 8/1999 | Mackey | |
| 5,935,079 A | 8/1999 | Swanson et al. | |
| 5,941,869 A | 8/1999 | Patterson et al. | |
| 5,951,494 A | 9/1999 | Wang et al. | |
| 5,951,546 A | 9/1999 | Lorentzen | |
| 5,954,661 A | 9/1999 | Greenspon et al. | |
| 5,954,662 A | 9/1999 | Swanson et al. | |
| 5,954,717 A | 9/1999 | Behl et al. | |
| 5,956,501 A | 9/1999 | Brown | 395/500.32 |
| 5,957,919 A | 9/1999 | Laufer | 606/28 |
| 5,957,961 A | 9/1999 | Maguire et al. | |
| 5,964,223 A | 10/1999 | Baran | 128/207.14 |
| 5,964,753 A | 10/1999 | Edwards | |
| 5,964,796 A | 10/1999 | Imran | |
| 5,971,983 A | 10/1999 | Lesh | |
| 5,972,026 A | 10/1999 | Laufer et al. | 607/96 |
| 5,976,175 A | 11/1999 | Hirano et al. | |
| 5,976,709 A | 11/1999 | Kageyama et al. | |
| 5,979,456 A | 11/1999 | Magovern | |
| 5,980,563 A | 11/1999 | Tu et al. | |
| 5,984,917 A | 11/1999 | Fleischman et al. | |
| 5,984,971 A | 11/1999 | Faccioli et al. | |
| 5,989,545 A | 11/1999 | Foster et al. | 424/183.1 |
| 5,991,650 A | 11/1999 | Swanson et al. | |
| 5,992,419 A | 11/1999 | Sterzer et al. | |
| 5,993,462 A | 11/1999 | Pomeranz et al. | |
| 5,995,873 A | 11/1999 | Rhodes | 607/46 |
| 5,997,534 A | 12/1999 | Tu et al. | |
| 5,999,855 A | 12/1999 | DiMarco | |
| 6,001,054 A | 12/1999 | Regulla et al. | |
| 6,003,517 A | 12/1999 | Sheffield et al. | |
| 6,004,269 A | 12/1999 | Crowley et al. | |
| 6,006,134 A | 12/1999 | Hill et al. | 607/9 |
| 6,006,755 A | 12/1999 | Edwards | |
| 6,008,211 A | 12/1999 | Robinson et al. | |
| 6,009,877 A | 1/2000 | Edwards | |
| 6,010,500 A | 1/2000 | Sherman et al. | |
| 6,014,579 A | 1/2000 | Pomeranz et al. | |
| 6,016,437 A | 1/2000 | Tu et al. | 600/374 |
| 6,023,638 A | 2/2000 | Swanson | |
| 6,024,740 A | 2/2000 | Lesh et al. | |
| 6,029,091 A | 2/2000 | De La Rama et al. | |
| 6,033,397 A | 3/2000 | Laufer et al. | |
| 6,036,687 A | 3/2000 | Laufer et al. | |
| 6,036,689 A | 3/2000 | Tu et al. | |
| 6,039,731 A | 3/2000 | Taylor et al. | |
| 6,043,273 A | 3/2000 | Duhaylongsod | 514/478 |
| 6,045,549 A | 4/2000 | Smethers et al. | |
| 6,045,550 A | 4/2000 | Simpson et al. | |
| 6,050,992 A | 4/2000 | Nichols | |
| 6,052,607 A | 4/2000 | Edwards et al. | |
| 6,053,172 A | 4/2000 | Hovda et al. | |
| 6,053,909 A | 4/2000 | Shadduck | |
| 6,056,744 A | 5/2000 | Edwards | |
| 6,056,745 A | 5/2000 | Panescu et al. | |
| 6,056,769 A | 5/2000 | Epstein et al. | |
| 6,060,454 A | 5/2000 | Duhaylongsod | 514/26 |
| 6,063,078 A | 5/2000 | Wittkampf | |
| 6,063,768 A | 5/2000 | First | 514/14 |
| 6,071,280 A | 6/2000 | Edwards et al. | |
| 6,071,281 A | 6/2000 | Burnside et al. | |
| 6,071,282 A | 6/2000 | Fleischman | |
| 6,081,749 A | 6/2000 | Ingle et al. | |
| 6,083,249 A | 7/2000 | Familoni | 607/40 |
| 6,083,255 A | 7/2000 | Laufer et al. | 607/96 |
| 6,087,394 A | 7/2000 | Duhaylongsod | 514/478 |
| 6,090,104 A | 7/2000 | Webster, Jr. | |
| 6,091,995 A | 7/2000 | Ingle et al. | |
| 6,092,528 A | 7/2000 | Edwards | |
| 6,097,985 A | 8/2000 | Kasevich et al. | 607/102 |
| 6,101,412 A | 8/2000 | Duhaylongsod | 607/2 |
| 6,102,886 A | 8/2000 | Lundquist et al. | |
| 6,106,524 A | 8/2000 | Eggers et al. | |
| 6,117,101 A | 9/2000 | Diedrich et al. | |
| 6,123,702 A | 9/2000 | Swanson et al. | |
| 6,123,703 A | 9/2000 | Tu et al. | |
| 6,123,718 A | 9/2000 | Tu et al. | |
| 6,125,301 A | 9/2000 | Capel | 607/74 |
| 6,127,410 A | 10/2000 | Duhaylongsod | 514/478 |
| 6,129,726 A | 10/2000 | Edwards et al. | 606/41 |
| 6,135,997 A | 10/2000 | Laufer et al. | |
| 6,139,527 A | 10/2000 | Laufer et al. | |
| 6,139,571 A | 10/2000 | Fuller et al. | |
| 6,139,845 A | 10/2000 | Donovan | 424/236.1 |
| 6,141,589 A | 10/2000 | Duhaylongsod | 607/10 |
| 6,142,993 A | 11/2000 | Whayne et al. | |
| 6,143,013 A | 11/2000 | Samson et al. | |
| 6,143,277 A | 11/2000 | Ashurst et al. | 424/45 |
| 6,149,647 A | 11/2000 | Tu et al. | |
| 6,152,143 A | 11/2000 | Edwards | |
| 6,152,899 A | 11/2000 | Farley et al. | |
| 6,152,953 A | 11/2000 | Hipskind | 607/109 |
| 6,159,194 A | 12/2000 | Eggers et al. | |
| 6,163,716 A | 12/2000 | Edwards et al. | |
| 6,174,323 B1 | 1/2001 | Biggs et al. | 606/232 |

(56) References Cited

U.S. PATENT DOCUMENTS

| | | | |
|---|---|---|---|
| 6,179,833 B1 | 1/2001 | Taylor | |
| 6,183,468 B1 | 2/2001 | Swanson et al. | |
| 6,197,013 B1 | 3/2001 | Reed et al. | |
| 6,198,970 B1 | 3/2001 | Freed et al. | 607/42 |
| 6,200,311 B1 | 3/2001 | Danek et al. | |
| 6,200,332 B1 | 3/2001 | Del Giglio | |
| 6,200,333 B1 | 3/2001 | Laufer | |
| 6,203,562 B1 | 3/2001 | Ohkubo | 606/204 |
| 6,210,355 B1 | 4/2001 | Edwards et al. | |
| 6,210,367 B1 | 4/2001 | Carr | |
| 6,212,432 B1 | 4/2001 | Matsuura | 607/76 |
| 6,212,433 B1 | 4/2001 | Behl | |
| 6,214,002 B1 | 4/2001 | Fleischman et al. | |
| 6,216,043 B1 | 4/2001 | Swanson et al. | |
| 6,216,044 B1 | 4/2001 | Kordis | |
| 6,216,704 B1 | 4/2001 | Ingle et al. | |
| 6,217,576 B1 | 4/2001 | Tu et al. | |
| 6,226,543 B1 | 5/2001 | Gilboa et al. | |
| 6,230,052 B1 | 5/2001 | Wolff et al. | 607/2 |
| 6,231,595 B1 | 5/2001 | Dobak, III | |
| 6,235,024 B1 | 5/2001 | Tu | |
| 6,240,307 B1 | 5/2001 | Beatty et al. | |
| 6,241,727 B1 | 6/2001 | Tu et al. | |
| 6,245,065 B1 | 6/2001 | Panescu et al. | |
| 6,251,368 B1 | 6/2001 | Akehurst et al. | 424/45 |
| 6,253,762 B1 | 7/2001 | Britto | 128/200.14 |
| 6,254,598 B1 | 7/2001 | Edwards et al. | |
| 6,254,599 B1 | 7/2001 | Lesh et al. | 606/41 |
| 6,258,083 B1 | 7/2001 | Daniel et al. | 606/15 |
| 6,258,087 B1 | 7/2001 | Edwards et al. | |
| 6,264,653 B1 | 7/2001 | Falwell | |
| 6,265,379 B1 | 7/2001 | Donovan | 514/14 |
| 6,269,813 B1 | 8/2001 | Fitzgerald et al. | |
| 6,270,476 B1 | 8/2001 | Santoianni et al. | |
| 6,273,886 B1 | 8/2001 | Edwards et al. | |
| 6,273,907 B1 | 8/2001 | Laufer | |
| 6,283,987 B1 | 9/2001 | Laird et al. | |
| 6,283,988 B1 | 9/2001 | Laufer et al. | 607/96 |
| 6,283,989 B1 | 9/2001 | Laufer et al. | |
| 6,287,304 B1 | 9/2001 | Eggers et al. | |
| 6,296,639 B1 | 10/2001 | Truckai et al. | |
| 6,299,633 B1 | 10/2001 | Laufer | |
| 6,302,870 B1 | 10/2001 | Jacobsen et al. | 604/272 |
| 6,303,509 B1 | 10/2001 | Chen et al. | 438/706 |
| 6,306,423 B1 | 10/2001 | Donovan et al. | 424/423 |
| 6,315,173 B1 | 11/2001 | Di Giovanni et al. | 222/402.2 |
| 6,315,778 B1 | 11/2001 | Gambale et al. | |
| 6,317,615 B1 | 11/2001 | KenKnight et al. | |
| 6,322,559 B1 * | 11/2001 | Daulton et al. | 606/41 |
| 6,322,584 B2 | 11/2001 | Ingle et al. | |
| 6,325,798 B1 | 12/2001 | Edwards et al. | |
| 6,327,503 B1 | 12/2001 | Familoni | 607/40 |
| 6,338,727 B1 | 1/2002 | Noda et al. | |
| 6,338,836 B1 | 1/2002 | Kuth et al. | |
| 6,341,236 B1 | 1/2002 | Osorio et al. | 607/45 |
| 6,346,104 B2 | 2/2002 | Daly et al. | |
| 6,355,031 B1 | 3/2002 | Edwards et al. | |
| 6,356,786 B1 | 3/2002 | Rezai et al. | 607/45 |
| 6,356,787 B1 | 3/2002 | Rezai et al. | 607/45 |
| 6,357,447 B1 | 3/2002 | Swanson et al. | |
| 6,358,245 B1 | 3/2002 | Edwards et al. | |
| 6,358,926 B2 | 3/2002 | Donovan | 514/14 |
| 6,361,554 B1 | 3/2002 | Brisken | 623/1.1 |
| 6,363,937 B1 | 4/2002 | Hovda et al. | 128/898 |
| 6,366,814 B1 | 4/2002 | Boveja et al. | 607/45 |
| 6,379,352 B1 | 4/2002 | Reynolds et al. | |
| 6,383,509 B1 | 5/2002 | Donovan et al. | 424/423 |
| 6,394,956 B1 | 5/2002 | Chandrasekaran et al. | |
| 6,402,744 B2 | 6/2002 | Edwards et al. | |
| 6,405,732 B1 | 6/2002 | Edwards et al. | |
| 6,409,723 B1 | 6/2002 | Edwards | |
| 6,411,852 B1 | 6/2002 | Danek et al. | |
| 6,414,018 B1 | 7/2002 | Duhaylongsod | 514/478 |
| 6,416,511 B1 | 7/2002 | Lesh et al. | |
| 6,416,740 B1 | 7/2002 | Unger | |
| 6,423,058 B1 | 7/2002 | Edwards et al. | |
| 6,423,105 B1 | 7/2002 | Iijima et al. | |
| 6,424,864 B1 | 7/2002 | Matsuura | 607/3 |
| 6,425,877 B1 | 7/2002 | Edwards | |
| 6,425,887 B1 | 7/2002 | McGuckin et al. | 604/272 |
| 6,425,895 B1 | 7/2002 | Swanson et al. | |
| 6,432,092 B2 | 8/2002 | Miller | 604/272 |
| 6,436,130 B1 | 8/2002 | Philips et al. | |
| 6,438,423 B1 | 8/2002 | Rezai et al. | 607/46 |
| 6,440,128 B1 | 8/2002 | Edwards et al. | |
| 6,440,129 B1 | 8/2002 | Simpson | |
| 6,442,435 B2 | 8/2002 | King et al. | |
| 6,447,505 B2 | 9/2002 | McGovern et al. | 606/41 |
| 6,447,785 B1 | 9/2002 | Donovan | 424/239.1 |
| 6,448,231 B2 | 9/2002 | Graham | 514/21 |
| 6,451,013 B1 | 9/2002 | Bays et al. | |
| 6,458,121 B1 | 10/2002 | Rosenstock et al. | |
| 6,460,545 B2 | 10/2002 | Kordis | |
| 6,464,680 B1 | 10/2002 | Brisken et al. | 604/501 |
| 6,464,697 B1 | 10/2002 | Edwards et al. | |
| 6,475,160 B1 | 11/2002 | Sher | 600/556 |
| 6,480,746 B1 | 11/2002 | Ingle et al. | |
| 6,485,416 B1 | 11/2002 | Platt et al. | 600/300 |
| 6,488,673 B1 * | 12/2002 | Laufer et al. | 604/516 |
| 6,488,679 B1 | 12/2002 | Swanson et al. | |
| 6,491,710 B2 | 12/2002 | Satake | 606/191 |
| 6,493,589 B1 | 12/2002 | Medhkour et al. | |
| 6,494,880 B1 | 12/2002 | Swanson et al. | |
| 6,496,737 B2 | 12/2002 | Rudie et al. | 607/101 |
| 6,496,738 B2 | 12/2002 | Carr | |
| 6,506,399 B2 | 1/2003 | Donovan | 424/423 |
| 6,510,969 B2 | 1/2003 | Di Giovanni et al. | 222/402.2 |
| 6,514,246 B1 | 2/2003 | Swanson et al. | |
| 6,514,290 B1 | 2/2003 | Loomas | 623/23.65 |
| 6,519,488 B2 | 2/2003 | KenKnight et al. | |
| 6,522,913 B2 | 2/2003 | Swanson et al. | |
| 6,524,555 B1 | 2/2003 | Ashurst et al. | 424/45 |
| 6,526,320 B2 | 2/2003 | Mitchell | |
| 6,526,976 B1 | 3/2003 | Baran | 128/207.14 |
| 6,529,756 B1 | 3/2003 | Phan et al. | |
| 6,532,388 B1 | 3/2003 | Hill et al. | |
| 6,533,780 B1 | 3/2003 | Laird et al. | |
| 6,536,427 B2 | 3/2003 | Davies et al. | 128/203.15 |
| 6,544,226 B1 | 4/2003 | Gaiser et al. | |
| 6,544,262 B2 | 4/2003 | Fleischman | |
| 6,546,928 B1 | 4/2003 | Ashurst et al. | 128/200.23 |
| 6,546,932 B1 | 4/2003 | Nahon et al. | 128/898 |
| 6,546,934 B1 | 4/2003 | Ingle et al. | |
| 6,547,776 B1 | 4/2003 | Gaiser et al. | 604/506 |
| 6,547,788 B1 | 4/2003 | Maguire et al. | |
| 6,549,808 B1 | 4/2003 | Gisel et al. | 607/53 |
| 6,551,274 B2 | 4/2003 | Heiner | |
| 6,551,310 B1 | 4/2003 | Ganz et al. | |
| 6,558,333 B2 | 5/2003 | Gilboa et al. | |
| 6,558,378 B2 | 5/2003 | Sherman et al. | |
| 6,558,381 B2 | 5/2003 | Ingle et al. | |
| 6,562,034 B2 | 5/2003 | Edwards et al. | |
| 6,572,612 B2 | 6/2003 | Stewart et al. | |
| 6,575,623 B2 | 6/2003 | Werneth | |
| 6,575,969 B1 | 6/2003 | Rittman, III et al. | |
| 6,582,427 B1 | 6/2003 | Goble et al. | |
| 6,582,430 B2 | 6/2003 | Hall | |
| 6,587,718 B2 | 7/2003 | Talpade | |
| 6,587,719 B1 | 7/2003 | Barrett et al. | 607/2 |
| 6,587,731 B1 | 7/2003 | Ingle et al. | |
| 6,589,235 B2 | 7/2003 | Wong et al. | |
| 6,589,238 B2 | 7/2003 | Edwards et al. | |
| 6,593,130 B1 | 7/2003 | Sen et al. | |
| 6,599,311 B1 | 7/2003 | Biggs et al. | 606/232 |
| 6,601,581 B1 | 8/2003 | Babaev | 128/200.16 |
| 6,603,996 B1 | 8/2003 | Beatty et al. | |
| 6,610,054 B1 | 8/2003 | Edwards et al. | |
| 6,610,083 B2 | 8/2003 | Keller et al. | |
| 6,610,713 B2 | 8/2003 | Tracey | 514/343 |
| 6,613,002 B1 | 9/2003 | Clark et al. | |
| 6,613,045 B1 | 9/2003 | Laufer et al. | |
| 6,620,159 B2 | 9/2003 | Hegde | |
| 6,620,415 B2 | 9/2003 | Donovan | 424/239.1 |
| 6,622,047 B2 | 9/2003 | Barrett et al. | 607/45 |

(56) References Cited

U.S. PATENT DOCUMENTS

| | | |
|---|---|---|
| 6,623,742 B2 | 9/2003 | Voet .................. 424/236.1 |
| 6,626,855 B1 | 9/2003 | Weng et al. ................ 601/3 |
| 6,626,903 B2 | 9/2003 | McGuckin, Jr. et al. |
| 6,629,535 B2 | 10/2003 | Ingle et al. |
| 6,629,951 B2 | 10/2003 | Laufer et al. .............. 604/96.01 |
| 6,632,440 B1 | 10/2003 | Quinn et al. ................ 424/239.1 |
| 6,633,779 B1 | 10/2003 | Schuler et al. ................ 607/42 |
| 6,634,363 B1 | 10/2003 | Danek et al. ................ 128/898 |
| 6,635,054 B2 | 10/2003 | Fjield et al. |
| 6,635,056 B2 | 10/2003 | Kadhiresan et al. |
| 6,638,273 B1 | 10/2003 | Farley et al. |
| 6,640,119 B1 | 10/2003 | Budd et al. |
| 6,640,120 B1 | 10/2003 | Swanson et al. |
| 6,645,200 B1 | 11/2003 | Koblish et al. |
| 6,645,496 B2 | 11/2003 | Aoki et al. ................ 424/184.1 |
| 6,647,617 B1 | 11/2003 | Beatty et al. |
| 6,648,881 B2 | 11/2003 | KenKnight et al. |
| 6,649,161 B1 | 11/2003 | Donovan ................ 424/94.5 |
| 6,652,517 B1 | 11/2003 | Hall et al. |
| 6,652,548 B2 | 11/2003 | Evans et al. |
| 6,656,960 B2 | 12/2003 | Puskas ................ 514/345 |
| 6,658,279 B1 | 12/2003 | Swanson et al. |
| 6,663,622 B1 | 12/2003 | Foley et al. |
| 6,666,858 B2 | 12/2003 | Lafontaine |
| 6,669,693 B2 | 12/2003 | Friedman |
| 6,671,533 B2 | 12/2003 | Chen et al. |
| 6,673,068 B1 | 1/2004 | Berube |
| 6,673,070 B2 | 1/2004 | Edwards et al. |
| 6,675,047 B1 | 1/2004 | Konoplev et al. ................ 607/50 |
| 6,676,686 B2 | 1/2004 | Naganuma ................ 607/1 |
| 6,681,136 B2 | 1/2004 | Schuler et al. ................ 607/44 |
| 6,692,492 B2 | 2/2004 | Simpson et al. |
| 6,692,494 B1 | 2/2004 | Cooper et al. ................ 606/46 |
| 6,699,180 B2 | 3/2004 | Kobayashi |
| 6,699,243 B2 | 3/2004 | West et al. |
| 6,708,064 B2 | 3/2004 | Rezai ................ 607/45 |
| 6,711,436 B1 | 3/2004 | Duhaylongsod ................ 607/9 |
| 6,712,074 B2 | 3/2004 | Edwards et al. |
| 6,712,812 B2 | 3/2004 | Roschak et al. ................ 606/41 |
| 6,712,814 B2 | 3/2004 | Edwards et al. |
| 6,714,822 B2 | 3/2004 | King et al. |
| 6,719,685 B2 | 4/2004 | Fujikura et al. |
| 6,719,694 B2 | 4/2004 | Weng et al. ................ 600/439 |
| 6,723,053 B2 | 4/2004 | Ackerman et al. |
| 6,723,091 B2 | 4/2004 | Goble et al. |
| 6,728,562 B1 | 4/2004 | Budd et al. |
| 6,735,471 B2 | 5/2004 | Hill et al. |
| 6,735,475 B1 | 5/2004 | Whitehurst et al. ........... 607/46 |
| 6,740,321 B1 | 5/2004 | Donovan ................ 424/94.6 |
| 6,743,197 B1 | 6/2004 | Edwards |
| 6,743,413 B1 | 6/2004 | Schultz et al. ................ 424/45 |
| 6,749,604 B1 | 6/2004 | Eggers et al. |
| 6,749,606 B2 | 6/2004 | Keast et al. ................ 606/41 |
| 6,752,765 B1 | 6/2004 | Jensen et al. ................ 600/536 |
| 6,755,026 B2 | 6/2004 | Wallach |
| 6,755,849 B1 | 6/2004 | Gowda et al. ................ 607/89 |
| 6,767,347 B2 | 7/2004 | Sharkey et al. |
| 6,767,544 B2 | 7/2004 | Brooks et al. ................ 424/247.1 |
| 6,770,070 B1 | 8/2004 | Balbierz |
| 6,772,013 B1 | 8/2004 | Ingle et al. |
| 6,773,711 B2 | 8/2004 | Voet et al. ................ 424/239.1 |
| 6,776,991 B2 | 8/2004 | Naumann ................ 424/239.1 |
| 6,777,423 B2 | 8/2004 | Banholzer et al. ............ 514/291 |
| 6,778,854 B2 | 8/2004 | Puskas ................ 607/2 |
| 6,780,183 B2 | 8/2004 | Jimenez et al. |
| 6,786,889 B1 | 9/2004 | Musbach et al. |
| 6,802,843 B2 | 10/2004 | Truckai et al. |
| 6,805,131 B2 | 10/2004 | Kordis |
| 6,819,956 B2 | 11/2004 | DiLorenzo ................ 607/45 |
| 6,826,420 B1 | 11/2004 | Beatty et al. |
| 6,826,421 B1 | 11/2004 | Beatty et al. |
| 6,827,931 B1 | 12/2004 | Donovan ................ 424/94.63 |
| 6,836,688 B2 | 12/2004 | Ingle et al. |
| 6,837,888 B2 | 1/2005 | Ciarrocca et al. |
| 6,838,429 B2 | 1/2005 | Paslin ................ 514/2 |
| 6,838,434 B2 | 1/2005 | Voet ................ 514/2 |
| 6,838,471 B2 | 1/2005 | Tracey ................ 514/343 |
| 6,840,243 B2 | 1/2005 | Deem et al. |
| 6,841,156 B2 | 1/2005 | Aoki et al. ................ 424/184.1 |
| 6,843,998 B1 | 1/2005 | Steward et al. ............ 424/236.1 |
| 6,846,312 B2 | 1/2005 | Edwards et al. |
| 6,847,849 B2 | 1/2005 | Mamo et al. ................ 607/117 |
| 6,849,073 B2 | 2/2005 | Hoey et al. |
| 6,852,091 B2 | 2/2005 | Edwards et al. |
| 6,852,110 B2 | 2/2005 | Roy et al. |
| 6,861,058 B2 | 3/2005 | Aoki et al. ................ 424/184.1 |
| 6,866,662 B2 | 3/2005 | Fuimaono et al. |
| 6,871,092 B2 | 3/2005 | Piccone ................ 607/3 |
| 6,872,206 B2 | 3/2005 | Edwards et al. |
| 6,872,397 B2 | 3/2005 | Aoki et al. ................ 424/239.1 |
| 6,878,156 B1 | 4/2005 | Noda |
| 6,881,213 B2 | 4/2005 | Ryan et al. |
| 6,885,888 B2 | 4/2005 | Rezai ................ 607/9 |
| 6,890,347 B2 | 5/2005 | Machold et al. |
| 6,893,436 B2 | 5/2005 | Woodard et al. |
| 6,893,438 B2 | 5/2005 | Hall et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,908,462 B2 | 6/2005 | Joye et al. |
| 6,908,928 B2 | 6/2005 | Banholzer et al. ............ 514/291 |
| 6,913,616 B2 | 7/2005 | Hamilton et al. ................ 607/89 |
| 6,917,834 B2 | 7/2005 | Koblish et al. |
| 6,934,583 B2 | 8/2005 | Weinberg et al. ................ 607/9 |
| 6,937,896 B1 | 8/2005 | Kroll ................ 607/9 |
| 6,937,903 B2 | 8/2005 | Schuler et al. ................ 607/42 |
| 6,939,309 B1 | 9/2005 | Beatty et al. |
| 6,939,345 B2 | 9/2005 | KenKnight et al. |
| 6,939,346 B2 | 9/2005 | Kannenberg et al. |
| 6,947,785 B1 | 9/2005 | Beatty et al. |
| 6,954,977 B2 | 10/2005 | Maguire et al. |
| 6,957,106 B2 | 10/2005 | Schuler et al. ................ 607/44 |
| 6,961,622 B2 | 11/2005 | Gilbert ................ 607/148 |
| 6,970,742 B2 | 11/2005 | Mann et al. ................ 607/23 |
| RE38,912 E | 12/2005 | Walz et al. ................ 424/46 |
| 6,971,395 B2 | 12/2005 | Edwards et al. |
| 6,974,224 B2 | 12/2005 | Thomas-Benedict ......... 362/103 |
| 6,974,456 B2 | 12/2005 | Edwards et al. |
| 6,974,578 B1 | 12/2005 | Aoki et al. ................ 424/239.1 |
| 6,978,168 B2 | 12/2005 | Beatty et al. |
| 6,978,174 B2 | 12/2005 | Gelfand et al. ................ 607/3 |
| 6,990,370 B1 | 1/2006 | Beatty et al. |
| 6,994,706 B2 | 2/2006 | Chornenky et al. |
| 6,997,189 B2 | 2/2006 | Biggs et al. ................ 128/898 |
| 7,004,942 B2 | 2/2006 | Laird et al. |
| 7,022,088 B2 | 4/2006 | Keast et al. ................ 601/2 |
| 7,022,105 B1 | 4/2006 | Edwards ................ 604/103.01 |
| 7,027,869 B2 | 4/2006 | Danek et al. ................ 607/42 |
| 7,043,307 B1 | 5/2006 | Zelickson et al. |
| 7,070,800 B2 | 7/2006 | Bechtold-Peters et al. ... 424/434 |
| 7,072,720 B2 | 7/2006 | Puskas |
| 7,083,614 B2 | 8/2006 | Fjield et al. |
| 7,101,368 B2 | 9/2006 | Lafontaine |
| 7,101,387 B2 | 9/2006 | Garabedian et al. ........... 607/105 |
| 7,104,987 B2 | 9/2006 | Biggs et al. ................ 606/34 |
| 7,104,990 B2 | 9/2006 | Jenkins et al. |
| 7,112,198 B2 | 9/2006 | Satake ................ 606/41 |
| 7,118,568 B2 | 10/2006 | Hassett et al. |
| 7,122,031 B2 | 10/2006 | Edwards et al. |
| 7,122,033 B2 | 10/2006 | Wood |
| 7,125,407 B2 | 10/2006 | Edwards et al. |
| 7,131,445 B2 | 11/2006 | Amoah |
| 7,142,910 B2 | 11/2006 | Puskas ................ 607/2 |
| 7,150,745 B2 | 12/2006 | Stern et al. |
| 7,162,303 B2 | 1/2007 | Levin et al. ................ 607/44 |
| 7,165,551 B2 | 1/2007 | Edwards et al. |
| 7,167,757 B2 | 1/2007 | Ingle et al. |
| 7,175,644 B2 | 2/2007 | Cooper et al. ................ 606/191 |
| 7,179,257 B2 | 2/2007 | West et al. ................ 606/41 |
| 7,186,251 B2 | 3/2007 | Malecki et al. |
| 7,187,964 B2 | 3/2007 | Khoury |
| 7,187,973 B2 | 3/2007 | Hauck |
| 7,189,208 B1 | 3/2007 | Beatty et al. |
| 7,198,635 B2 | 4/2007 | Danek et al. ................ 607/96 |

(56) References Cited

U.S. PATENT DOCUMENTS

| | | | |
|---|---|---|---|
| 7,200,445 B1 | 4/2007 | Dalbec et al. | 607/101 |
| 7,229,469 B1 | 6/2007 | Witzel et al. | |
| 7,238,357 B2 | 7/2007 | Barron | 424/239.1 |
| 7,241,295 B2 | 7/2007 | Maguire | 606/41 |
| 7,255,693 B1 | 8/2007 | Johnston et al. | |
| RE39,820 E | 9/2007 | Banholzer et al. | 514/291 |
| 7,264,002 B2 | 9/2007 | Danek et al. | 128/898 |
| 7,266,414 B2 | 9/2007 | Cornelius et al. | |
| 7,273,055 B2 | 9/2007 | Danek et al. | |
| 7,289,843 B2 | 10/2007 | Beatty et al. | |
| 7,291,146 B2 | 11/2007 | Steinke et al. | |
| 7,292,890 B2 | 11/2007 | Whitehurst et al. | 607/45 |
| 7,309,707 B2 | 12/2007 | Bender et al. | 514/291 |
| 7,310,552 B2 | 12/2007 | Puskas | 607/2 |
| RE40,045 E | 2/2008 | Palmer | 424/43 |
| 7,326,207 B2 | 2/2008 | Edwards | |
| 7,344,535 B2 | 3/2008 | Stern et al. | |
| 7,371,231 B2 | 5/2008 | Rioux et al. | |
| 7,393,330 B2 | 7/2008 | Keast et al. | 601/2 |
| 7,393,350 B2 | 7/2008 | Maurice | |
| 7,394,976 B2 | 7/2008 | Entenman et al. | |
| 7,402,172 B2 | 7/2008 | Chin et al. | |
| 7,422,563 B2 | 9/2008 | Roschak et al. | 601/2 |
| 7,422,584 B2 | 9/2008 | Loomas et al. | 606/32 |
| 7,425,212 B1 | 9/2008 | Danek et al. | 606/47 |
| 7,430,449 B2 | 9/2008 | Aldrich et al. | 607/40 |
| 7,462,162 B2 | 12/2008 | Phan et al. | 604/8 |
| 7,462,179 B2 | 12/2008 | Edwards et al. | |
| 7,473,273 B2 | 1/2009 | Campbell | |
| 7,477,945 B2 | 1/2009 | Rezai et al. | |
| 7,483,755 B2 | 1/2009 | Ingle et al. | |
| 7,493,160 B2 | 2/2009 | Weber et al. | |
| 7,494,661 B2 | 2/2009 | Sanders | 424/239.1 |
| 7,507,234 B2 | 3/2009 | Utley et al. | |
| 7,507,238 B2 | 3/2009 | Edwards et al. | |
| 7,517,320 B2 | 4/2009 | Wibowo et al. | 600/529 |
| 7,530,979 B2 | 5/2009 | Ganz et al. | |
| 7,532,938 B2 | 5/2009 | Machado et al. | |
| 7,542,802 B2 | 6/2009 | Danek et al. | 607/42 |
| 7,553,307 B2 | 6/2009 | Bleich et al. | 606/1 |
| 7,556,624 B2 | 7/2009 | Laufer et al. | |
| 7,559,890 B2 | 7/2009 | Wallace et al. | |
| 7,572,245 B2 | 8/2009 | Herweck et al. | |
| 7,585,296 B2 | 9/2009 | Edwards et al. | |
| 7,588,549 B2 | 9/2009 | Eccleston | |
| 7,594,925 B2 | 9/2009 | Danek et al. | 607/96 |
| 7,608,275 B2 | 10/2009 | Deem et al. | 424/236.1 |
| 7,613,515 B2 | 11/2009 | Knudson et al. | |
| 7,617,005 B2 | 11/2009 | Demarais et al. | |
| 7,620,451 B2 | 11/2009 | Demarais et al. | |
| 7,628,789 B2 | 12/2009 | Soltesz et al. | |
| 7,632,268 B2 | 12/2009 | Edwards et al. | |
| 7,641,632 B2 | 1/2010 | Noda et al. | |
| 7,641,633 B2 | 1/2010 | Laufer et al. | |
| 7,648,500 B2 | 1/2010 | Edwards et al. | |
| 7,653,438 B2 | 1/2010 | Deem et al. | |
| 7,684,865 B2 | 3/2010 | Aldrich et al. | 607/40 |
| 7,689,290 B2 | 3/2010 | Ingle et al. | |
| 7,691,079 B2 | 4/2010 | Gobel | |
| RE41,334 E | 5/2010 | Beatty et al. | |
| 7,708,712 B2 | 5/2010 | Phan et al. | 604/8 |
| 7,708,768 B2 | 5/2010 | Danek et al. | 607/96 |
| 7,711,430 B2 | 5/2010 | Errico et al. | 607/42 |
| 7,717,948 B2 | 5/2010 | Demarais et al. | |
| 7,722,538 B2 | 5/2010 | Khoury | |
| 7,725,188 B2 | 5/2010 | Errico et al. | 607/23 |
| 7,734,355 B2 | 6/2010 | Cohen et al. | 607/118 |
| 7,734,535 B1 | 6/2010 | Burns | 705/37 |
| 7,740,017 B2 | 6/2010 | Danek et al. | 128/898 |
| 7,740,631 B2 | 6/2010 | Bleich et al. | 606/79 |
| 7,742,795 B2 | 6/2010 | Stone et al. | |
| 7,747,324 B2 | 6/2010 | Errico et al. | 607/42 |
| 7,756,583 B2 | 7/2010 | Demarais et al. | |
| 7,765,010 B2 | 7/2010 | Chornenky et al. | |
| 7,770,584 B2 | 8/2010 | Danek et al. | |
| 7,783,358 B2 | 8/2010 | Aldrich et al. | 607/40 |
| 7,815,590 B2 | 10/2010 | Cooper | 604/8 |
| 7,826,881 B1 | 11/2010 | Beatty et al. | |
| 7,831,288 B1 | 11/2010 | Beatty et al. | |
| 7,837,676 B2 | 11/2010 | Sinelnikov et al. | |
| 7,837,679 B2 | 11/2010 | Biggs et al. | 606/34 |
| 7,841,986 B2 | 11/2010 | He et al. | |
| 7,844,338 B2 | 11/2010 | Knudson et al. | |
| 7,853,331 B2 | 12/2010 | Kaplan et al. | |
| 7,854,734 B2 | 12/2010 | Biggs et al. | 606/34 |
| 7,854,740 B2 | 12/2010 | Carney | |
| 7,869,879 B2 | 1/2011 | Errico et al. | 607/23 |
| 7,869,880 B2 | 1/2011 | Errico et al. | 607/42 |
| 7,873,417 B2 | 1/2011 | Demarais et al. | |
| 7,877,146 B2 | 1/2011 | Rezai et al. | |
| 7,904,159 B2 | 3/2011 | Errico et al. | 607/23 |
| 7,906,124 B2 | 3/2011 | Laufer et al. | 424/239.1 |
| 7,914,448 B2 | 3/2011 | Bob et al. | |
| 7,921,855 B2 | 4/2011 | Danek et al. | 128/898 |
| 7,930,012 B2 | 4/2011 | Beatty et al. | |
| 7,931,647 B2 | 4/2011 | Wizeman et al. | 606/41 |
| 7,937,143 B2 | 5/2011 | Demarais et al. | |
| 7,938,123 B2 | 5/2011 | Danek et al. | |
| 7,949,407 B2 | 5/2011 | Kaplan et al. | 607/101 |
| 7,967,782 B2 | 6/2011 | Laufer et al. | |
| 7,985,187 B2 | 7/2011 | Wibowo et al. | 600/529 |
| 7,992,572 B2 | 8/2011 | Danek et al. | 128/898 |
| 7,993,336 B2 | 8/2011 | Jackson et al. | |
| 8,002,740 B2 | 8/2011 | Willink et al. | 604/96.01 |
| 8,007,495 B2 * | 8/2011 | McDaniel et al. | 606/41 |
| 8,010,197 B2 | 8/2011 | Errico et al. | 607/42 |
| 8,012,149 B2 | 9/2011 | Jackson et al. | |
| 8,041,428 B2 | 10/2011 | Errico et al. | 607/44 |
| 8,046,085 B2 | 10/2011 | Knudson et al. | |
| 8,052,668 B2 | 11/2011 | Sih | |
| 8,088,127 B2 | 1/2012 | Mayse et al. | |
| 8,099,167 B1 | 1/2012 | Errico et al. | 607/42 |
| 8,105,817 B2 | 1/2012 | Deem et al. | |
| 8,128,595 B2 | 3/2012 | Walker et al. | |
| 8,128,617 B2 | 3/2012 | Bencini et al. | |
| 8,131,371 B2 | 3/2012 | Demarals et al. | |
| 8,152,803 B2 | 4/2012 | Edwards et al. | |
| 8,204,598 B2 | 6/2012 | Errico et al. | |
| 8,208,998 B2 | 6/2012 | Beatty et al. | |
| 8,209,034 B2 | 6/2012 | Simon et al. | |
| 8,216,216 B2 | 7/2012 | Warnking et al. | |
| 8,226,638 B2 | 7/2012 | Mayse et al. | |
| 8,229,564 B2 | 7/2012 | Rezai | |
| 8,231,621 B2 | 7/2012 | Hutchins et al. | |
| 8,233,988 B2 | 7/2012 | Errico et al. | |
| 8,251,992 B2 | 8/2012 | Utley et al. | |
| 8,267,094 B2 | 9/2012 | Danek et al. | |
| 8,295,902 B2 | 10/2012 | Salahieh et al. | |
| 8,303,581 B2 | 11/2012 | Arts et al. | |
| 8,313,484 B2 | 11/2012 | Edwards et al. | |
| 8,328,798 B2 | 12/2012 | Witzel et al. | |
| 8,347,891 B2 | 1/2013 | Demarais et al. | |
| 8,357,118 B2 | 1/2013 | Orr | |
| 8,364,237 B2 | 1/2013 | Stone et al. | |
| 8,371,303 B2 | 2/2013 | Schaner et al. | |
| 8,377,055 B2 | 2/2013 | Jackson et al. | |
| 8,777,943 B2 * | 7/2014 | Mayse et al. | 606/41 |
| 2001/0020151 A1 | 9/2001 | Reed et al. | |
| 2001/0044596 A1 | 11/2001 | Jaafar | 604/103.01 |
| 2002/0002387 A1 | 1/2002 | Naganuma | 607/1 |
| 2002/0010495 A1 | 1/2002 | Freed et al. | 607/42 |
| 2002/0016344 A1 | 2/2002 | Tracey | 514/343 |
| 2002/0042564 A1 | 4/2002 | Cooper et al. | 600/407 |
| 2002/0042565 A1 | 4/2002 | Cooper et al. | 600/407 |
| 2002/0049370 A1 | 4/2002 | Laufer et al. | 600/300 |
| 2002/0072738 A1 | 6/2002 | Edwards et al. | 606/41 |
| 2002/0082197 A1 | 6/2002 | Aoki et al. | 514/2 |
| 2002/0087153 A1 | 7/2002 | Roschak et al. | 606/27 |
| 2002/0087208 A1 * | 7/2002 | Koblish et al. | 607/113 |
| 2002/0091379 A1 | 7/2002 | Danek et al. | 606/32 |
| 2002/0107512 A1 | 8/2002 | Edwards | |
| 2002/0107515 A1 | 8/2002 | Edwards et al. | 606/41 |
| 2002/0111386 A1 | 8/2002 | Sekins et al. | 514/759 |
| 2002/0111619 A1 | 8/2002 | Keast et al. | 606/41 |

(56) References Cited

U.S. PATENT DOCUMENTS

| | | | |
|---|---|---|---|
| 2002/0111620 A1 | 8/2002 | Cooper et al. ................ 606/41 |
| 2002/0115991 A1* | 8/2002 | Edwards ...................... 606/41 |
| 2002/0116030 A1 | 8/2002 | Rezai .......................... 607/9 |
| 2002/0143302 A1 | 10/2002 | Hinchliffe et al. ........... 604/272 |
| 2002/0143326 A1 | 10/2002 | Foley et al. |
| 2002/0143373 A1 | 10/2002 | Courtnage et al. ............ 607/91 |
| 2002/0151888 A1 | 10/2002 | Edwards et al. ............... 606/41 |
| 2002/0183682 A1 | 12/2002 | Darvish et al. ................ 604/20 |
| 2002/0198512 A1 | 12/2002 | Seward ........................ 604/522 |
| 2002/0198570 A1 | 12/2002 | Puskas ......................... 607/40 |
| 2002/0198574 A1 | 12/2002 | Gumpert ...................... 607/58 |
| 2003/0018344 A1 | 1/2003 | Kaji et al. .................... 606/130 |
| 2003/0023287 A1* | 1/2003 | Edwards et al. ............. 607/101 |
| 2003/0027752 A1 | 2/2003 | Steward et al. ............... 514/12 |
| 2003/0050591 A1 | 3/2003 | McHale ....................... 604/4.01 |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0070676 A1 | 4/2003 | Cooper et al. ............ 128/200.24 |
| 2003/0074039 A1 | 4/2003 | Puskas ........................ 607/118 |
| 2003/0093069 A1 | 5/2003 | Panescu et al. |
| 2003/0093128 A1 | 5/2003 | Freed et al. ................... 607/42 |
| 2003/0125786 A1 | 7/2003 | Gliner et al. |
| 2003/0130657 A1 | 7/2003 | Tom et al. .................... 606/47 |
| 2003/0144572 A1 | 7/2003 | Oschman et al. ............ 600/16 |
| 2003/0153905 A1 | 8/2003 | Edwards et al. |
| 2003/0159700 A1 | 8/2003 | Laufer et al. ................ 128/898 |
| 2003/0181949 A1 | 9/2003 | Whale .......................... 607/2 |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. ........... 424/239.1 |
| 2003/0208103 A1 | 11/2003 | Sonnenschein et al. |
| 2003/0211121 A1 | 11/2003 | Donovan ................... 424/247.1 |
| 2003/0216791 A1 | 11/2003 | Schuler et al. ............... 607/44 |
| 2003/0216792 A1 | 11/2003 | Levin et al. .................. 607/48 |
| 2003/0216891 A1 | 11/2003 | Wegener ..................... 702/188 |
| 2003/0225443 A1 | 12/2003 | Kiran et al. |
| 2003/0233099 A1 | 12/2003 | Danaek et al. ............... 606/96 |
| 2003/0236455 A1 | 12/2003 | Swanson et al. |
| 2004/0006268 A1 | 1/2004 | Gilboa et al. |
| 2004/0009180 A1 | 1/2004 | Donovan ................... 424/184.1 |
| 2004/0010289 A1 | 1/2004 | Biggs et al. .................. 607/2 |
| 2004/0010290 A1 | 1/2004 | Schroeppel et al. .......... 607/3 |
| 2004/0028676 A1 | 2/2004 | Klein et al. .................. 424/125 |
| 2004/0029849 A1 | 2/2004 | Schatzberg et al. .......... 514/179 |
| 2004/0030368 A1 | 2/2004 | Kemeny et al. .............. 607/88 |
| 2004/0031494 A1 | 2/2004 | Danek et al. |
| 2004/0044390 A1 | 3/2004 | Szeles ......................... 607/142 |
| 2004/0059383 A1 | 3/2004 | Puskas ........................ 607/1 |
| 2004/0073201 A1 | 4/2004 | Cooper et al. ............... 606/14 |
| 2004/0073206 A1 | 4/2004 | Foley et al. |
| 2004/0073278 A1 | 4/2004 | Pachys ......................... 607/88 |
| 2004/0086531 A1 | 5/2004 | Barron ....................... 424/239.1 |
| 2004/0087936 A1 | 5/2004 | Stern et al. |
| 2004/0088030 A1 | 5/2004 | Jung, Jr. ...................... 607/109 |
| 2004/0088036 A1 | 5/2004 | Gilbert ......................... 607/148 |
| 2004/0091880 A1 | 5/2004 | Wiebusch et al. ............ 435/6 |
| 2004/0106954 A1 | 6/2004 | Whitehurst et al. .......... 607/3 |
| 2004/0116981 A1 | 6/2004 | Mazar ......................... 607/60 |
| 2004/0122488 A1 | 6/2004 | Mazar et al. ................. 607/60 |
| 2004/0122489 A1 | 6/2004 | Mazar et al. ................. 607/60 |
| 2004/0127942 A1 | 7/2004 | Yomtov et al. ............... 607/3 |
| 2004/0127958 A1 | 7/2004 | Mazar et al. ................. 607/60 |
| 2004/0142005 A1 | 7/2004 | Brooks et al. .............. 424/239.1 |
| 2004/0147921 A1 | 7/2004 | Edwards et al. |
| 2004/0147969 A1 | 7/2004 | Mann et al. .................. 607/17 |
| 2004/0147988 A1 | 7/2004 | Stephens ..................... 607/108 |
| 2004/0151741 A1 | 8/2004 | Borodic ...................... 424/239.1 |
| 2004/0153056 A1 | 8/2004 | Muller et al. |
| 2004/0162584 A1 | 8/2004 | Hill et al. |
| 2004/0162597 A1 | 8/2004 | Hamilton et al. ............. 607/89 |
| 2004/0167509 A1 | 8/2004 | Taimisto ...................... 606/41 |
| 2004/0167580 A1 | 8/2004 | Mann et al. .................. 607/17 |
| 2004/0172075 A1 | 9/2004 | Shafer et al. ................. 607/9 |
| 2004/0172080 A1 | 9/2004 | Stadler et al. ................ 607/17 |
| 2004/0172084 A1 | 9/2004 | Knudson et al. ............. 607/40 |
| 2004/0175399 A1 | 9/2004 | Schiffman ................... 424/239.1 |
| 2004/0176803 A1 | 9/2004 | Whelan et al. ............... 607/2 |
| 2004/0176805 A1 | 9/2004 | Whelan et al. ............... 607/2 |
| 2004/0182399 A1 | 9/2004 | Danek et al. ................. 128/898 |
| 2004/0186435 A1 | 9/2004 | Seward ....................... 604/164.12 |
| 2004/0204747 A1 | 10/2004 | Kemeny et al. .............. 607/94 |
| 2004/0213813 A1 | 10/2004 | Ackerman .................. 424/239.1 |
| 2004/0213814 A1 | 10/2004 | Ackerman .................. 424/239.1 |
| 2004/0215235 A1 | 10/2004 | Jackson et al. |
| 2004/0215289 A1 | 10/2004 | Fukui ........................... 607/48 |
| 2004/0215296 A1 | 10/2004 | Ganz et al. |
| 2004/0220556 A1 | 11/2004 | Cooper et al. ............... 606/1 |
| 2004/0220621 A1 | 11/2004 | Zhou et al. ................... 607/2 |
| 2004/0226556 A1 | 11/2004 | Deem et al. ................ 128/200.24 |
| 2004/0230251 A1 | 11/2004 | Schuler et al. ............... 607/42 |
| 2004/0230252 A1 | 11/2004 | Kullok et al. ................. 607/48 |
| 2004/0243118 A1 | 12/2004 | Ayers et al. |
| 2004/0243182 A1 | 12/2004 | Cohen et al. ................. 607/2 |
| 2004/0248188 A1 | 12/2004 | Sanders ....................... 435/7.1 |
| 2004/0249401 A1 | 12/2004 | Rabiner et al. |
| 2004/0249416 A1 | 12/2004 | Yun et al. ..................... 607/2 |
| 2004/0253274 A1 | 12/2004 | Voet ........................... 424/239.1 |
| 2005/0004609 A1 | 1/2005 | Stahmann et al. ............ 607/17 |
| 2005/0004631 A1 | 1/2005 | Benedict ...................... 607/88 |
| 2005/0010263 A1 | 1/2005 | Schauerte .................... 607/48 |
| 2005/0010270 A1 | 1/2005 | Laufer ......................... 607/88 |
| 2005/0015117 A1 | 1/2005 | Gerber ......................... 607/39 |
| 2005/0019346 A1 | 1/2005 | Boulis ........................ 424/190.1 |
| 2005/0021092 A1 | 1/2005 | Yun et al. ..................... 607/3 |
| 2005/0049615 A1 | 3/2005 | Cooper et al. ............... 606/140 |
| 2005/0056292 A1 | 3/2005 | Cooper ........................ 128/898 |
| 2005/0059153 A1 | 3/2005 | George et al. ............... 435/446 |
| 2005/0060041 A1 | 3/2005 | Phan et al. ................... 623/23.7 |
| 2005/0060042 A1 | 3/2005 | Phan et al. ................... 623/23.7 |
| 2005/0060044 A1 | 3/2005 | Roschak et al. ............. 623/23.65 |
| 2005/0065553 A1 | 3/2005 | Ben Ezra et al. ............. 607/2 |
| 2005/0065562 A1 | 3/2005 | Rezai ........................... 607/9 |
| 2005/0065567 A1 | 3/2005 | Lee et al. ..................... 607/17 |
| 2005/0065573 A1 | 3/2005 | Rezai ........................... 607/42 |
| 2005/0065574 A1 | 3/2005 | Rezai ........................... 607/45 |
| 2005/0065575 A1 | 3/2005 | Dobak |
| 2005/0065584 A1 | 3/2005 | Schiff et al. |
| 2005/0074461 A1 | 4/2005 | Donovan .................... 424/184.1 |
| 2005/0076909 A1 | 4/2005 | Stahmann et al. .......... 128/204.23 |
| 2005/0080461 A1 | 4/2005 | Stahmann et al. ............ 607/17 |
| 2005/0085801 A1 | 4/2005 | Cooper et al. ............... 606/14 |
| 2005/0090722 A1 | 4/2005 | Perez ........................... 600/315 |
| 2005/0096529 A1 | 5/2005 | Cooper et al. ............... 600/407 |
| 2005/0096644 A1 | 5/2005 | Hall et al. |
| 2005/0107783 A1 | 5/2005 | Tom et al. .................... 606/47 |
| 2005/0107829 A1 | 5/2005 | Edwards et al. ............. 607/2 |
| 2005/0107853 A1 | 5/2005 | Krespi et al. ................. 607/89 |
| 2005/0125044 A1 | 6/2005 | Tracey ......................... 607/45 |
| 2005/0137518 A1 | 6/2005 | Biggs et al. .................. 604/8 |
| 2005/0137611 A1 | 6/2005 | Escudero et al. ............ 606/108 |
| 2005/0137715 A1 | 6/2005 | Phan et al. ................... 623/23.65 |
| 2005/0143788 A1 | 6/2005 | Yun et al. ..................... 607/46 |
| 2005/0149146 A1 | 7/2005 | Boveja et al. ................ 607/58 |
| 2005/0152924 A1 | 7/2005 | Voet ........................... 424/239.1 |
| 2005/0153885 A1 | 7/2005 | Yun et al. ..................... 514/12 |
| 2005/0159736 A9 | 7/2005 | Danek et al. ................. 606/32 |
| 2005/0165456 A1 | 7/2005 | Mann et al. .................. 607/30 |
| 2005/0171396 A1 | 8/2005 | Pankratov et al. |
| 2005/0177144 A1 | 8/2005 | Phan et al. ................... 606/14 |
| 2005/0177192 A1 | 8/2005 | Rezai et al. .................. 607/3 |
| 2005/0182288 A1 | 8/2005 | Zabara ......................... 600/14 |
| 2005/0182393 A1 | 8/2005 | Abboud et al. |
| 2005/0183732 A1 | 8/2005 | Edwards ..................... 128/898 |
| 2005/0187579 A1 | 8/2005 | Danek et al. ................. 607/1 |
| 2005/0193279 A1 | 9/2005 | Daners |
| 2005/0203503 A1 | 9/2005 | Edwards et al. |
| 2005/0222628 A1 | 10/2005 | Krakousky .................. 607/3 |
| 2005/0222635 A1 | 10/2005 | Krakovsky ................... 607/39 |
| 2005/0222651 A1 | 10/2005 | Jung, Jr. ...................... 607/104 |
| 2005/0228054 A1 | 10/2005 | Tatton ......................... 514/656 |
| 2005/0228459 A1 | 10/2005 | Levin et al. .................. 607/40 |
| 2005/0228460 A1 | 10/2005 | Levin et al. .................. 607/40 |

(56) References Cited

U.S. PATENT DOCUMENTS

| | | | |
|---|---|---|---|
| 2005/0234523 A1 | 10/2005 | Levin et al. | 607/42 |
| 2005/0238693 A1 | 10/2005 | Whyte | 424/439 |
| 2005/0240176 A1 | 10/2005 | Oral et al. | |
| 2005/0240241 A1 | 10/2005 | Yun et al. | 607/42 |
| 2005/0245992 A1 | 11/2005 | Persen et al. | 607/60 |
| 2005/0251128 A1 | 11/2005 | Amoah | |
| 2005/0251213 A1 | 11/2005 | Freeman | 607/5 |
| 2005/0255317 A1 | 11/2005 | Bavaro et al. | |
| 2005/0256028 A1 | 11/2005 | Yun et al. | 514/2 |
| 2005/0261747 A1 | 11/2005 | Schuler et al. | 607/42 |
| 2005/0267536 A1 | 12/2005 | Freeman et al. | 607/5 |
| 2005/0277993 A1 | 12/2005 | Mower | 607/9 |
| 2005/0283197 A1 | 12/2005 | Daum et al. | 607/17 |
| 2006/0015151 A1 | 1/2006 | Aldrich | 607/40 |
| 2006/0058692 A1 | 3/2006 | Beatty et al. | |
| 2006/0058693 A1 | 3/2006 | Beatty et al. | |
| 2006/0058780 A1 | 3/2006 | Edwards et al. | 606/40 |
| 2006/0062808 A1 | 3/2006 | Laufer et al. | 424/239.1 |
| 2006/0079887 A1 | 4/2006 | Buysse et al. | |
| 2006/0084884 A1 | 4/2006 | Beatty et al. | |
| 2006/0084966 A1* | 4/2006 | Maguire et al. | 606/41 |
| 2006/0084970 A1 | 4/2006 | Beatty et al. | |
| 2006/0084971 A1 | 4/2006 | Beatty et al. | |
| 2006/0084972 A1 | 4/2006 | Beatty et al. | |
| 2006/0089637 A1 | 4/2006 | Werneth et al. | |
| 2006/0095029 A1 | 5/2006 | Young et al. | |
| 2006/0095032 A1 | 5/2006 | Jackson et al. | |
| 2006/0100666 A1 | 5/2006 | Wilkinson et al. | 607/1 |
| 2006/0106361 A1 | 5/2006 | Muni et al. | 604/500 |
| 2006/0111755 A1 | 5/2006 | Stone et al. | 607/42 |
| 2006/0116749 A1 | 6/2006 | Willink et al. | 623/1.11 |
| 2006/0118127 A1 | 6/2006 | Chinn et al. | |
| 2006/0135953 A1 | 6/2006 | Kania et al. | |
| 2006/0135984 A1 | 6/2006 | Kramer et al. | 606/192 |
| 2006/0135998 A1 | 6/2006 | Libbus et al. | 607/2 |
| 2006/0137698 A1 | 6/2006 | Danek et al. | 128/898 |
| 2006/0142801 A1 | 6/2006 | Demarais et al. | 607/2 |
| 2006/0167498 A1 | 7/2006 | DiLorenzo | 607/2 |
| 2006/0178703 A1 | 8/2006 | Huston et al. | 607/2 |
| 2006/0206150 A1 | 9/2006 | Demarais et al. | 607/3 |
| 2006/0212076 A1 | 9/2006 | Demarais et al. | 607/2 |
| 2006/0212078 A1 | 9/2006 | Demarais et al. | 607/3 |
| 2006/0222667 A1 | 10/2006 | Deem et al. | 424/239.1 |
| 2006/0225742 A1 | 10/2006 | Deem et al. | 128/207.14 |
| 2006/0235474 A1 | 10/2006 | Demarais | 607/2 |
| 2006/0241523 A1 | 10/2006 | Sinelnikov et al. | |
| 2006/0247617 A1 | 11/2006 | Danek et al. | 606/41 |
| 2006/0247618 A1 | 11/2006 | Kaplan et al. | 606/41 |
| 2006/0247619 A1 | 11/2006 | Kaplan et al. | 606/41 |
| 2006/0247683 A1 | 11/2006 | Danek et al. | 607/2 |
| 2006/0247726 A1 | 11/2006 | Biggs et al. | 607/42 |
| 2006/0247727 A1 | 11/2006 | Biggs et al. | 607/42 |
| 2006/0247746 A1 | 11/2006 | Danek et al. | 607/115 |
| 2006/0254600 A1 | 11/2006 | Danek et al. | 128/898 |
| 2006/0259028 A1 | 11/2006 | Utley et al. | 606/41 |
| 2006/0259029 A1 | 11/2006 | Utley et al. | 606/41 |
| 2006/0259030 A1 | 11/2006 | Utley et al. | 606/41 |
| 2006/0265014 A1 | 11/2006 | Demarais et al. | 607/2 |
| 2006/0265015 A1 | 11/2006 | Demarais et al. | 607/2 |
| 2006/0271111 A1 | 11/2006 | Demarais et al. | 607/2 |
| 2006/0276807 A1 | 12/2006 | Keast et al. | 606/140 |
| 2006/0276852 A1 | 12/2006 | Demarais et al. | 607/44 |
| 2006/0278243 A1 | 12/2006 | Danek et al. | 128/898 |
| 2006/0278244 A1 | 12/2006 | Danek et al. | 128/898 |
| 2006/0280772 A1 | 12/2006 | Roschak et al. | 424/426 |
| 2006/0280773 A1 | 12/2006 | Roschak et al. | 424/426 |
| 2006/0282071 A1 | 12/2006 | Utley et al. | |
| 2006/0287679 A1 | 12/2006 | Stone | 607/2 |
| 2007/0021803 A1 | 1/2007 | Deem et al. | 607/46 |
| 2007/0025919 A1 | 2/2007 | Deem et al. | |
| 2007/0027496 A1 | 2/2007 | Parnis et al. | 607/42 |
| 2007/0032788 A1 | 2/2007 | Edwards et al. | |
| 2007/0043342 A1 | 2/2007 | Kleinberger | |
| 2007/0043350 A1 | 2/2007 | Soltesz et al. | |
| 2007/0055328 A1 | 3/2007 | Mayse et al. | |
| 2007/0060954 A1 | 3/2007 | Cameron et al. | 607/2 |
| 2007/0060990 A1 | 3/2007 | Satake | 607/101 |
| 2007/0062545 A1 | 3/2007 | Danek et al. | 128/898 |
| 2007/0066957 A1 | 3/2007 | Demarais et al. | 604/500 |
| 2007/0074719 A1 | 4/2007 | Danek et al. | |
| 2007/0083194 A1 | 4/2007 | Kunis et al. | |
| 2007/0083197 A1 | 4/2007 | Danek et al. | 606/47 |
| 2007/0083239 A1 | 4/2007 | Demarais et al. | |
| 2007/0093802 A1 | 4/2007 | Danek et al. | 606/41 |
| 2007/0093809 A1 | 4/2007 | Edwards et al. | 606/41 |
| 2007/0100390 A1 | 5/2007 | Danaek et al. | 607/42 |
| 2007/0102011 A1 | 5/2007 | Danek et al. | 128/898 |
| 2007/0106292 A1 | 5/2007 | Kaplan et al. | 606/41 |
| 2007/0106296 A1 | 5/2007 | Laufer et al. | 606/50 |
| 2007/0106337 A1 | 5/2007 | Errico et al. | 607/40 |
| 2007/0106338 A1 | 5/2007 | Errico | 607/42 |
| 2007/0106339 A1 | 5/2007 | Errico et al. | 607/42 |
| 2007/0106348 A1 | 5/2007 | Laufer | 607/88 |
| 2007/0112349 A1 | 5/2007 | Danek et al. | 606/45 |
| 2007/0118184 A1 | 5/2007 | Danek et al. | 607/42 |
| 2007/0118190 A1 | 5/2007 | Danek et al. | 607/96 |
| 2007/0123922 A1 | 5/2007 | Cooper et al. | 606/191 |
| 2007/0123958 A1 | 5/2007 | Laufer | 607/93 |
| 2007/0123961 A1 | 5/2007 | Danek et al. | 607/101 |
| 2007/0129720 A1 | 6/2007 | Demarais et al. | 606/41 |
| 2007/0129760 A1 | 6/2007 | Demarais et al. | 607/2 |
| 2007/0129761 A1 | 6/2007 | Demarais et al. | 607/3 |
| 2007/0135875 A1 | 6/2007 | Demarais et al. | 607/96 |
| 2007/0173899 A1 | 7/2007 | Levin et al. | 607/40 |
| 2007/0191902 A1 | 8/2007 | Errico et al. | 607/42 |
| 2007/0197896 A1 | 8/2007 | Moll et al. | 600/407 |
| 2007/0203549 A1 | 8/2007 | Demarais et al. | 607/72 |
| 2007/0225768 A1 | 9/2007 | Dobak | 607/2 |
| 2007/0232896 A1 | 10/2007 | Gilboa et al. | |
| 2007/0239256 A1 | 10/2007 | Weber et al. | |
| 2007/0244479 A1 | 10/2007 | Beatty et al. | |
| 2007/0250050 A1 | 10/2007 | Lafontaine | |
| 2007/0255270 A1 | 11/2007 | Carney | |
| 2007/0255304 A1 | 11/2007 | Roschak et al. | 606/185 |
| 2007/0265639 A1 | 11/2007 | Danek et al. | 606/130 |
| 2007/0265687 A1 | 11/2007 | Deem et al. | 607/72 |
| 2007/0267011 A1 | 11/2007 | Deem et al. | 128/200.23 |
| 2007/0270794 A1 | 11/2007 | Anderson et al. | |
| 2008/0004596 A1 | 1/2008 | Yun et al. | |
| 2008/0021274 A1 | 1/2008 | Bayer et al. | |
| 2008/0021369 A1 | 1/2008 | Deem et al. | 604/20 |
| 2008/0051839 A1 | 2/2008 | Libbus et al. | 607/2 |
| 2008/0086107 A1 | 4/2008 | Roschak | 604/506 |
| 2008/0097422 A1 | 4/2008 | Edwards et al. | |
| 2008/0097424 A1 | 4/2008 | Wizeman et al. | 606/41 |
| 2008/0125772 A1 | 5/2008 | Stone et al. | |
| 2008/0147137 A1 | 6/2008 | Cohen et al. | 607/17 |
| 2008/0154258 A1 | 6/2008 | Chang et al. | |
| 2008/0161801 A1 | 7/2008 | Steinke et al. | |
| 2008/0183248 A1 | 7/2008 | Rezai et al. | 607/62 |
| 2008/0188912 A1 | 8/2008 | Stone et al. | |
| 2008/0188913 A1 | 8/2008 | Stone et al. | |
| 2008/0194956 A1 | 8/2008 | Aldrich et al. | 600/439 |
| 2008/0208305 A1 | 8/2008 | Rezai et al. | |
| 2008/0213331 A1 | 9/2008 | Gelfand et al. | 424/422 |
| 2008/0234564 A1 | 9/2008 | Beatty et al. | |
| 2008/0243112 A1 | 10/2008 | De Neve | 606/28 |
| 2008/0255449 A1 | 10/2008 | Warnking et al. | |
| 2008/0255642 A1 | 10/2008 | Zarins et al. | 607/99 |
| 2008/0262489 A1 | 10/2008 | Steinke | 606/33 |
| 2008/0275445 A1 | 11/2008 | Kelly et al. | |
| 2008/0302359 A1 | 12/2008 | Loomas et al. | 128/200.24 |
| 2008/0306570 A1 | 12/2008 | Rezai et al. | 607/42 |
| 2008/0312543 A1 | 12/2008 | Laufer et al. | 600/486 |
| 2008/0312725 A1 | 12/2008 | Penner | 607/119 |
| 2008/0319350 A1 | 12/2008 | Wallace et al. | |
| 2009/0018473 A1 | 1/2009 | Aldrich et al. | 601/2 |
| 2009/0018538 A1 | 1/2009 | Webster et al. | 606/41 |
| 2009/0030477 A1 | 1/2009 | Jarrard | 607/42 |
| 2009/0036948 A1 | 2/2009 | Levin et al. | 607/44 |
| 2009/0043301 A1 | 2/2009 | Jarrard et al. | 606/41 |
| 2009/0043302 A1 | 2/2009 | Ford et al. | 606/41 |
| 2009/0048593 A1 | 2/2009 | Ganz et al. | |
| 2009/0060953 A1 | 3/2009 | Sandars | 424/239.1 |

(56) References Cited

U.S. PATENT DOCUMENTS

| | | | |
|---|---|---|---|
| 2009/0062873 A1 | 3/2009 | Wu et al. | 607/2 |
| 2009/0069797 A1 | 3/2009 | Danek et al. | 606/33 |
| 2009/0076409 A1 | 3/2009 | Wu et al. | 600/547 |
| 2009/0076491 A1 | 3/2009 | Roschak et al. | 606/21 |
| 2009/0112203 A1 | 4/2009 | Danek et al. | 606/33 |
| 2009/0124883 A1 | 5/2009 | Wibowo et al. | 600/407 |
| 2009/0131765 A1 | 5/2009 | Roschak et al. | 600/301 |
| 2009/0131928 A1 | 5/2009 | Edwards et al. | 606/33 |
| 2009/0131930 A1 | 5/2009 | Gelbart et al. | |
| 2009/0143678 A1 | 6/2009 | Keast et al. | 600/439 |
| 2009/0143705 A1 | 6/2009 | Danek et al. | 601/3 |
| 2009/0143776 A1 | 6/2009 | Danek et al. | 606/21 |
| 2009/0143831 A1 | 6/2009 | Huston et al. | 607/2 |
| 2009/0155336 A1 | 6/2009 | Rezai | 424/423 |
| 2009/0177192 A1 | 7/2009 | Rioux et al. | |
| 2009/0192505 A1 | 7/2009 | Askew et al. | |
| 2009/0192508 A1 | 7/2009 | Laufer et al. | 606/41 |
| 2009/0204005 A1 | 8/2009 | Keast et al. | 600/461 |
| 2009/0204119 A1 | 8/2009 | Bleich et al. | 606/79 |
| 2009/0227885 A1 | 9/2009 | Lowery et al. | |
| 2009/0227980 A1 | 9/2009 | Kangas et al. | |
| 2009/0232850 A1 | 9/2009 | Manack et al. | 424/239.1 |
| 2009/0248011 A1 | 10/2009 | Hlavka et al. | 606/41 |
| 2009/0254079 A1 | 10/2009 | Edwards et al. | |
| 2009/0254142 A1 | 10/2009 | Edwards et al. | |
| 2009/0259274 A1 | 10/2009 | Simon et al. | 607/40 |
| 2009/0275840 A1 | 11/2009 | Roschak et al. | 600/467 |
| 2009/0275878 A1 | 11/2009 | Cambier et al. | 604/21 |
| 2009/0281593 A9 | 11/2009 | Errico et al. | 607/42 |
| 2009/0287087 A1 | 11/2009 | Gwerder et al. | 600/463 |
| 2009/0306644 A1 | 12/2009 | Mayse et al. | 606/33 |
| 2009/0318904 A9 | 12/2009 | Cooper et al. | 606/1 |
| 2009/0319002 A1 | 12/2009 | Simon | 607/45 |
| 2010/0003282 A1 | 1/2010 | Deem et al. | 424/238.1 |
| 2010/0004648 A1 | 1/2010 | Edwards et al. | |
| 2010/0010564 A1 | 1/2010 | Simon | 607/45 |
| 2010/0016709 A1 | 1/2010 | Gilboa et al. | |
| 2010/0042089 A1 | 2/2010 | Soltesz et al. | |
| 2010/0049031 A1 | 2/2010 | Fruland et al. | |
| 2010/0049186 A1 | 2/2010 | Ingle et al. | |
| 2010/0049188 A1 | 2/2010 | Nelson et al. | |
| 2010/0057178 A1 | 3/2010 | Simon | 607/117 |
| 2010/0063495 A1 | 3/2010 | Edwards et al. | |
| 2010/0070004 A1 | 3/2010 | Hlavka et al. | 607/62 |
| 2010/0076518 A1 | 3/2010 | Hlavka et al. | 607/42 |
| 2010/0087783 A1 | 4/2010 | Weber et al. | |
| 2010/0087809 A1 | 4/2010 | Edwards et al. | |
| 2010/0094231 A1 | 4/2010 | Bleich et al. | 604/274 |
| 2010/0114087 A1 | 5/2010 | Edwards et al. | |
| 2010/0116279 A9 | 5/2010 | Cooper | 128/898 |
| 2010/0125239 A1 | 5/2010 | Perry et al. | |
| 2010/0130892 A1 | 5/2010 | Warnking | |
| 2010/0137860 A1 | 6/2010 | Demarais et al. | 606/41 |
| 2010/0145427 A1 | 6/2010 | Gliner et al. | |
| 2010/0152835 A1 | 6/2010 | Orr | |
| 2010/0160906 A1 | 6/2010 | Jarrard | 606/33 |
| 2010/0160996 A1 | 6/2010 | Simon et al. | 607/44 |
| 2010/0174340 A1 | 7/2010 | Simon | 607/40 |
| 2010/0179424 A1 | 7/2010 | Warnking et al. | |
| 2010/0185190 A1 | 7/2010 | Danek et al. | 606/29 |
| 2010/0191089 A1 | 7/2010 | Stebler et al. | |
| 2010/0204689 A1 | 8/2010 | Danek et al. | 606/27 |
| 2010/0222851 A1 | 9/2010 | Deem et al. | |
| 2010/0228318 A1 | 9/2010 | Errico et al. | 607/42 |
| 2010/0241188 A1 | 9/2010 | Errico et al. | 607/42 |
| 2010/0249873 A1 | 9/2010 | Errico | 607/40 |
| 2010/0256629 A1 | 10/2010 | Wylie et al. | |
| 2010/0256630 A1 | 10/2010 | Hamilton et al. | |
| 2010/0268222 A1 | 10/2010 | Danek et al. | 606/41 |
| 2010/0298905 A1 | 11/2010 | Simon | 607/40 |
| 2010/0305463 A1 | 12/2010 | Macklem et al. | 600/529 |
| 2010/0318020 A1 | 12/2010 | Atanasoska et al. | |
| 2010/0331776 A1 | 12/2010 | Salahieh et al. | |
| 2011/0004148 A1 | 1/2011 | Ishii | |
| 2011/0015548 A1 | 1/2011 | Aldrich et al. | 601/2 |
| 2011/0028898 A1 | 2/2011 | Clark, III et al. | |
| 2011/0046432 A1 | 2/2011 | Simon et al. | 600/14 |
| 2011/0060380 A1 | 3/2011 | Gelfand et al. | 607/42 |
| 2011/0079230 A1 | 4/2011 | Danek et al. | 128/898 |
| 2011/0093032 A1 | 4/2011 | Boggs, II et al. | 607/42 |
| 2011/0098762 A1 | 4/2011 | Rezai | |
| 2011/0112400 A1 | 5/2011 | Emery et al. | 600/439 |
| 2011/0112521 A1 | 5/2011 | DeLonzor et al. | |
| 2011/0118725 A1 | 5/2011 | Mayse et al. | 606/33 |
| 2011/0125203 A1 | 5/2011 | Simon et al. | 607/2 |
| 2011/0125213 A1 | 5/2011 | Simon et al. | 607/42 |
| 2011/0130708 A1 | 6/2011 | Perry et al. | |
| 2011/0137284 A1 | 6/2011 | Arora et al. | |
| 2011/0144630 A1 | 6/2011 | Loeb | |
| 2011/0146673 A1 | 6/2011 | Keast et al. | 128/200.24 |
| 2011/0146674 A1 | 6/2011 | Roschak | 128/200.24 |
| 2011/0152855 A1* | 6/2011 | Mayse et al. | 606/33 |
| 2011/0152967 A1 | 6/2011 | Simon et al. | 607/45 |
| 2011/0152974 A1 | 6/2011 | Rezai et al. | |
| 2011/0166499 A1 | 7/2011 | Demarais et al. | |
| 2011/0166565 A1 | 7/2011 | Wizeman et al. | 606/33 |
| 2011/0172655 A1 | 7/2011 | Biggs et al. | 606/34 |
| 2011/0172658 A1 | 7/2011 | Gelbart et al. | |
| 2011/0178569 A1 | 7/2011 | Parnis et al. | |
| 2011/0184330 A1 | 7/2011 | Laufer et al. | 604/8 |
| 2011/0190569 A1 | 8/2011 | Simon et al. | 600/26 |
| 2011/0196288 A1 | 8/2011 | Kaplan et al. | 604/28 |
| 2011/0202098 A1 | 8/2011 | Demarais et al. | |
| 2011/0224768 A1 | 9/2011 | Edwards | |
| 2011/0230701 A1 | 9/2011 | Simon et al. | 600/9 |
| 2011/0230938 A1 | 9/2011 | Simon et al. | 607/63 |
| 2011/0245756 A1 | 10/2011 | Arora et al. | |
| 2011/0251592 A1 | 10/2011 | Biggs et al. | 604/514 |
| 2011/0257622 A1 | 10/2011 | Salahieh et al. | |
| 2011/0257647 A1* | 10/2011 | Mayse et al. | 606/33 |
| 2011/0263960 A1 | 10/2011 | Mitchell | |
| 2011/0264086 A1 | 10/2011 | Ingle | |
| 2011/0270249 A1 | 11/2011 | Utley et al. | |
| 2011/0276107 A1 | 11/2011 | Simon et al. | 607/46 |
| 2011/0276112 A1 | 11/2011 | Simon et al. | 607/72 |
| 2011/0282229 A1 | 11/2011 | Danek et al. | 600/538 |
| 2011/0282418 A1 | 11/2011 | Saunders et al. | |
| 2011/0301587 A1* | 12/2011 | Deem et al. | 606/33 |
| 2011/0301664 A1 | 12/2011 | Rezai | 607/42 |
| 2011/0301679 A1 | 12/2011 | Rezai et al. | |
| 2011/0306851 A1 | 12/2011 | Wang | |
| 2011/0306904 A1 | 12/2011 | Jacobson et al. | |
| 2011/0306997 A9 | 12/2011 | Roschak et al. | 606/185 |
| 2011/0319958 A1 | 12/2011 | Simon et al. | 607/42 |
| 2012/0004656 A1 | 1/2012 | Jackson et al. | |
| 2012/0015019 A1 | 1/2012 | Pacetti et al. | |
| 2012/0016256 A1 | 1/2012 | Mabary et al. | |
| 2012/0016358 A1 | 1/2012 | Mayse et al. | 606/33 |
| 2012/0016363 A1 | 1/2012 | Mayse et al. | 606/41 |
| 2012/0016364 A1* | 1/2012 | Mayse et al. | 606/41 |
| 2012/0029261 A1 | 2/2012 | Deem et al. | |
| 2012/0029500 A1 | 2/2012 | Jenson | |
| 2012/0029512 A1 | 2/2012 | Willard et al. | |
| 2012/0029591 A1 | 2/2012 | Simon et al. | 607/42 |
| 2012/0029601 A1 | 2/2012 | Simon et al. | 607/72 |
| 2012/0041412 A1 | 2/2012 | Roth et al. | |
| 2012/0041509 A1 | 2/2012 | Knudson et al. | |
| 2012/0071870 A1 | 3/2012 | Salahieh et al. | |
| 2012/0078096 A1 | 3/2012 | Krolik et al. | |
| 2012/0083734 A1 | 4/2012 | Ayres et al. | |
| 2012/0089078 A1 | 4/2012 | Deem et al. | |
| 2012/0089138 A1 | 4/2012 | Edwards et al. | |
| 2012/0101326 A1 | 4/2012 | Simon et al. | |
| 2012/0101413 A1 | 4/2012 | Beetel et al. | |
| 2012/0109278 A1 | 5/2012 | Sih | |
| 2012/0143132 A1 | 6/2012 | Orlowski | |
| 2012/0143177 A1 | 6/2012 | Avitall | |
| 2012/0143179 A1 | 6/2012 | Avitall | |
| 2012/0143181 A1 | 6/2012 | Demarais et al. | |
| 2012/0157986 A1 | 6/2012 | Stone et al. | |
| 2012/0157987 A1 | 6/2012 | Steinke et al. | |
| 2012/0157988 A1 | 6/2012 | Stone et al. | |
| 2012/0157989 A1 | 6/2012 | Stone et al. | |
| 2012/0158101 A1 | 6/2012 | Stone et al. | |

(56) References Cited

U.S. PATENT DOCUMENTS

| | | |
|---|---|---|
| 2012/0165803 A1 | 6/2012 | Bencini et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking |
| 2012/0245415 A1 | 9/2012 | Emura et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |
| 2013/0289556 A1 | 10/2013 | Mayse et al. |
| 2013/0296647 A1 | 11/2013 | Mayse et al. |
| 2013/0310822 A1 | 11/2013 | Mayse et al. |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |

FOREIGN PATENT DOCUMENTS

| | | |
|---|---|---|
| DE | 19952505 A1 | 3/2001 |
| EP | 189329 A3 | 6/1987 |
| EP | 286145 A2 | 10/1988 |
| EP | 280225 A3 | 3/1989 |
| EP | 286145 A3 | 10/1990 |
| EP | 282225 B1 | 6/1992 |
| EP | 0 643 982 | 3/1995 |
| EP | 908713 A1 | 4/1999 |
| EP | 1 143 864 | 10/2001 |
| EP | 1 271 384 | 1/2003 |
| EP | 1 281 366 | 2/2003 |
| EP | 908150 B1 | 5/2003 |
| EP | 1 326 549 | 7/2003 |
| EP | 768091 B1 | 7/2003 |
| EP | 1326548 | 7/2003 |
| EP | 1 400 204 | 3/2004 |
| EP | 1297795 B1 | 8/2005 |
| EP | 1 588 662 | 10/2005 |
| FR | 2659240 B1 | 7/1997 |
| GB | 2233293 A | 1/1991 |
| GB | 2233293 | 2/1994 |
| RU | 2053814 | 2/1996 |
| RU | 2091054 C1 | 9/1997 |
| WO | 89/11311 | 11/1989 |
| WO | 93/01862 | 2/1993 |
| WO | 93/16632 | 9/1993 |
| WO | 94/07446 | 4/1994 |
| WO | 95/01075 | 1/1995 |
| WO | WO-9502370 A3 | 1/1995 |
| WO | WO-9510322 A1 | 4/1995 |
| WO | WO-9604860 A1 | 2/1996 |
| WO | WO-9610961 A1 | 4/1996 |
| WO | 97/25917 | 7/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | 98/18391 | 5/1998 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO 99/35988 | 7/1999 |
| WO | WO-9932040 A1 | 7/1999 |
| WO | 99/42047 | 8/1999 |
| WO | WO-9964109 A1 | 12/1999 |
| WO | 00/10598 | 3/2000 |
| WO | WO-0051510 A1 | 9/2000 |
| WO | 00/62699 | 10/2000 |
| WO | 00/66017 | 11/2000 |
| WO | WO 99/35986 | 11/2000 |
| WO | 01/00114 | 1/2001 |
| WO | WO-0103642 A1 | 1/2001 |
| WO | 01/70114 | 9/2001 |
| WO | 01/89526 | 11/2001 |
| WO | WO-0205720 A1 | 1/2002 |
| WO | WO-0205868 A2 | 1/2002 |
| WO | WO-0232333 A1 | 4/2002 |
| WO | WO-0232334 A1 | 4/2002 |
| WO | 03/073358 | 9/2003 |
| WO | 03/088820 | 10/2003 |
| WO | 2004/078252 | 9/2004 |
| WO | 2004/082736 | 9/2004 |
| WO | 2004/101028 | 11/2004 |
| WO | 2005/006963 | 1/2005 |
| WO | 2005/006964 | 1/2005 |
| WO | 2006/053308 | 5/2006 |
| WO | 2006/053309 | 5/2006 |
| WO | 2006/116198 | 11/2006 |
| WO | 2007/058780 A9 | 5/2007 |
| WO | 2007/061982 | 5/2007 |
| WO | 2007/092062 A1 | 8/2007 |
| WO | 2007/094828 A3 | 8/2007 |
| WO | 2007/143665 | 12/2007 |
| WO | 2008/005953 | 1/2008 |
| WO | 2008/024220 | 2/2008 |
| WO | 2008/051706 | 5/2008 |
| WO | 2008/063935 | 5/2008 |
| WO | WO 2008/071914 | 6/2008 |
| WO | 2009/009236 | 1/2009 |
| WO | 2009/015278 | 1/2009 |
| WO | WO-2009082433 A2 | 7/2009 |
| WO | 2009/126383 A3 | 10/2009 |
| WO | WO-2009137819 A1 | 11/2009 |
| WO | 2010/110785 A1 | 9/2010 |
| WO | WO-2011060200 A1 | 5/2011 |

OTHER PUBLICATIONS

Ahnert-Hilger et al., "Introduction of Macromolecules into Bovine Adrenal-Medullary Chromaffin Cells and Rat Pheochromocytoma Cells (PC12) by Permeabilization with Streptolysin O: Inhibitory Effect of Tetanus Toxin on Catecholamine Secretion," *J. Neurochem* 52(6):1751-1758, Jun. 1989.

Babichev et al., "Clinico-morphological comparisons in patients with bronchial asthma after denervation of the lungs," *Sov Med.* 12:13-16, 1985.

Babichev et al., "Long-term results of surgical treatment of bronchial asthma based on adaptive response," *Khirurgiia (Mosk)* 4:5-11, 1993.

Babichev et al., "Partial denervation of the lungs in bronchial asthma," *Khirurgiia (Mosk)* 4:31-35, 1985.

Barlaw, "Surgical Treatment of Asthma," *Postgrad Med. Journal* 25:193-196, 1949.

(56) References Cited

OTHER PUBLICATIONS

Bester et al., "Recovery of C-Fiber-Induced Extravasation Following Peripheral Nerve Injury in the Rat," *Experimental Neurology* 154:628-636, 1998.
Bigalke et al., "Clostridial Neurotoxins," *Handbook of Experimental Pharmacology* (Aktories, K., and Just, I., eds) 145:407-443, 2000.
Bittner et al., "Isolated Light Chains of Botulinum Neurotoxins Inhibit Exocytosis," *The Journal of Biological Chemistry* 264(18):10354-10360, 1989.
Blindt et al., "Development of a New Biodegradable Intravascular Polymer Stent with Simultaneous Incorporation of Bioactive Substances," *The International Journal of Artificial Organs* 22(12):843-853, 1999.
Brody et al., "Mucociliary clearance after lung denervation and bronchial transection," *J. Applied Physiology* 32(2):160-164, 1972.
Buzzi, "Diphtheria Toxin Treatment of Human Advanced Cancer," *Cancer Research* 42:2054-2058, 1982.
Canning et al., "Reflex Mechanisms in Gastroesophageal Reflux Disease and Asthma," *The American Journal of Medicine* 115(3A):45S-48S, 2003.
Canning et al., "Reflex Mechanisms in Gastroesophageal Reflux Disease and Asthma," *Am J Med.* 115(Suppl 3A):45S-48S, 2003. (Abstract only.).
Canning, "Reflex regulation of airway smooth muscle tone," *J Appl. Physiol.* (101):971-985, 2006.
Chaddock et al. "Expression and Purification of Catalytically Active, Non-Toxic Endopeptidase Derivatives of *Clostridium Botulinum* Toxin Type A," *Protein Expression and Purification* 25(2):219-228, Jul. 2002.
Chang, "Cell poration and cell fusion using an oscillating electric field," *Biophys. J.* 56:641-652, 1989.
Chernyshova et al., "The Effect of Low-Energy Laser Radiation in the Infrared Spectrum on Bronchial Patency in Children with Bronchial Asthma," *Vopr Kurortol Fizioter Lech Fiz Kult* 2:11-14, 1995. (+ English translation, 6 pages.).
Chumakov et al., "Morphologic Studies of Bronchial Biopsies in Chronic Bronchitis Before and After Treatment," *Arkh. Patol.* 57(6):21-25, 1995. (+ English abstract and translation, 8 pages.).
Crimi et al., "Protective effects of inhaled ipratropium bromide on bronchoconstriction induced by adenosine and methacholine in asthma," *Eur Respir J* 5:560-565, 1992.
De Paiva et al., "Light chain of botulinum neurotoxin is active in mammalian motor nerve terminals when delivered via liposomes," *FEBS Lett.* 17:277(1-2): 171-174, Dec. 1990.
Feshenko et al., "Clinico-morphological comparisons in the laser therapy of chronic bronchitis patients," *Lik Sprava.* (10-12):75-79, 1993. (+ English abstract, 1 Page.).
Gelb et al, "Laser in treatment of lung cancer," *Chest* 86(5):662-666, 1984.
Gerasin et al., "Endobronchial electrosurgery," *Chest* 93:270-274, 1988.
Gibson et al., "Gastroesophageal Reflux Treatment for Asthma in Adults and Children," *Cochrane Database Syst.* Rev. 2:CD001496, 2003. (Abstract only.).
Glanville et al., "Bronchial responsiveness after human heart-lung transplantation," *Chest* 97(6):1360-1366, 1990.
Glanville et al., "Bronchial responsiveness to exercise after human cardiopulmonary transplantation," *Chest* 96(2):81-286, 1989.
Gosens et al., "Muscarinic receptor signaling in the pathophysiology of asthma and COPD," *Respiratory Research* 7(73):1-15, 2006.
Groeben et al. "High Thoracic Epidural Anesthesia Does Not Alter Airway Resistance and Attenuates the Response to an Inhalational Provocation Test in Patients with Bronchial Hyperreactivity," *Anesthesiology* 81(4):868-874, 1994.
Guarini et al., "Efferent Vagal Fibre Stimulation Blunts Nuclear Factor-kB Activation and Protects Against Hypovolemic Hemmorrhagic Shock," *Circulation* 107:1189-1194, 2003.
Guzmán et al., "Bioeffects Caused by Changes in Acoustic Cavitation Bubble Density and Cell Concentration: A Unified Explanation Based on Cell-to-Bubble Ratio and Blast Radius," *Ultrasound in Med. & Biol.* 29(8):1211-1222, 2003.
Hainsworth et al., "Afferent lung denervation by brief inhalation of steam," *Journal of Applied Physiology* (34)5: 708-714, 1972.
Harding, "Recent Clinical Investigations Examining the Association of Asthma and Gastroesophageal Reflux," *Am J Med* 115(Suppl 3A):39S-44S, 2003. (Abstract only.).
Hiraga, "Experimental surgical therapy of bronchial asthma. The effect of denervation in dogs," *Nihon Kyobu Shikkan Gakkai Zasshi* 19(1):46-56, 1981.
Hoffmann et al., "Inhibition of Histamine-Induced Bronchoconstriction in Guinea Pig and Swine by Pulsed Electrical Vagus Nerve Stimulation," *Neuromodulation: Technology at the Neural Interface*:1-9, 2009.
Hooper et al., "Endobronchial electrocautery," *Chest* 87(6):12-714, 1985.
Ivanyuta OM, et al., "Effect of Low-Power Laser Irradiation of Bronchia Mucosa on the State of Systemic and Local Immunity in Patients with Chronic Bronchitis," *Problemy Tuberkuleza* 6:26-29, 1991.
Jammes et al., "Assessment of the Pulmonary Origin of Bronchoconstrictor Vagal Tone," *J. Physiol.* 291: 305-316, 1979.
Jiang et al., "Effects of Antireflux Treatment on Bronchial Hyperresponsiveness and Lung Function in Asthmatic Patients with Gastroesophageal Reflux Disease," *World J Gastroenterol.* 9:1123-1125, 2003. (Abstract only.).
Karashurov et al., "Electrostimulation in the therapy of bronchial asthma," *Klin Med* (*Mosk*) 79(11):38-41, 2001.
Karashurov et al., "Radiofrequency electrostimulation of carotid sinus nerves for the treatment of bronchial asthma," *Khirurgiia* (*Mosk*) 12:2-6, 1999.
Khmel'kova et al., "Does laser irridation affect bronchial obstruction?," *Probl Tuberk* 3:41-42, 1995. (Abstract only.).
Khoshoo et al., "Role of Gastroesophageal Reflux in Older Children with Persistent Asthma," *Chest* 123:1008-1013, 2003. (Abstract only.).
Kiljander, "The Role of Proton Pump Inhibitors in the Management of Gastroesophageal Reflux Disease-Related Asthma and Chronic Cough," *Am J Med.* 115(Suppl 3A):65S-71S, 2003. (Abstract only.).
Kistner et al., "Reductive Cleavage of Tetanus Toxin and Botulinum Neurotoxin a by the Thioredoxin System from Brain," *Naunyn-Schmiedebergs Arch Pharmacol* 345(2):227-234, Feb. 1992.
Kletskin et al., "Value of assessing the autonomic nervous system in bronchial asthma in selecting the surgical treatment method," *Khirurgiia* (*Mosk*) 7:91-95, 1987.
Kliachkin et al., "Bronchoscopy in the treatment of bronchial asthma of infectious allergic origin," *Ter Arkh* 54(4):76-79, 1982.
Korpela et al., "Comparison of Tissue Reactions in the Tracheal Mucosa Surrounding a Bioabsorbable and Silicone Airway Stents," *Annals of Thoracic Surgery* 66:1772-1776, 1998.
Kozaki et al., "New surgical treatment of bronchial asthma—denervation of the hilus pulmonis (2)," *Nippon Kyobu Geka Gakkai Zasshi* 22(5):465-466, 1974.
Kreitman, "Taming ricin toxin," *Nature Biotechnology* 21:372-374, 2003.
Kuntz, "The Autonomic Nervous System in Relation to the Thoracic Viscera," *Chest* 10:1-18, 1944.
Lennerz et al., "Electrophysiological characterization of vagal afferents relevant to mucosal nociception in the rat upper oesophagus," *J. Physiol.* 582(1):229-242, 2007.
Levin, "The Treatment of Bronchial Asthma by Dorsal Sympathectomy," *Annals of Surgery* 102(2):161-170, 1935.
Liou et al., "Causative and Contributive Factors to Asthmas Severity and Patterns of Medication Use in Patients Seeking Specialized Asthma Care," *Chest* 124:1781-1788, 2003. (Abstract only.).
Magnussen et al., "Effect of Inhaled Ipratropium Bromide on the Airway Response to Methacholine, Histamine, and Exercise in Patients with Mild Bronchial Asthma," *Respiration* 59:42-47, 1992.
Mathew et al., "Gastro-oesophageal reflux and bronchial asthma: current status and future directions," *Postgrad Med. J.* 80:701-705, 2004.
McKay et al., "Autocrine regulation of asthmatic airway inflammation: role of airway smooth muscle," *Respir Res* 3(11):1-13, 2002.

(56) References Cited

OTHER PUBLICATIONS

Mehta et al., "Effect of endobronchial radiation therapy on malignant bronchial obstruction," *Chest* 97(3):662-665, 1990.

Meshalkin et al., "Partial denervation of the pulmonary hilus as one of the methods of surgical treatment of bronchial asthma," *Grudn Khir* 1:109-111, 1975.

Moore, Keith L., *Clinically Oriented Anatomy*, 2nd ed., Williams & Wilkins, Baltimore, 1985, pp. 85 and 87. (Abstract only.).

Netter, Frank H., *The Ciba Collection of Medical Illustrations*: vol. 7, Respiratory System, CIBA-GEIGY Corporation, West Caldwell, 1979, p. 23, section 1. (Abstract only.).

Ochs, Matthias et al., Fisherman, Alfred P., et al. (eds), *Functional Design of the Human Lung for Gas Exchange*, 4th ed., McGraw Hill Medical, New York, 2008, Chap. 2, "Fisherman's Pulmonary Diseases and Disorders." (Abstract only.).

Ovcharenko et al., "Endobronchial use of low-frequency ultrasound and ultraviolet laser radiation in the complex treatment of patients with suppurative bronchial diseases," *Probl Tuberk* 3:40-42, 1997. (Abstract only.).

Overholt, "Glomectomy for Asthma," *Dis Chest* 40:605-610, 1961.

Petrou, et al., "Bronchoscopic Diathermy Resection and Stent Insertion: a Cost Effective Treatment for Tracheobronchial Obstruction," *Thorax* 48:1156-1159, 1993.

Polosukhin, "Dynamics of the ultrastructural changes in blood and lymphatic capillaries of bronchi in inflammation and following endobronchial laser therapy," *Virchows Arch.* 431:283-290, 1997.

Polosukhin, "Regeneration of Bronchial Epithelium on Chronic Inflammatory Changes Under Laser Treatment," *Path. Res. Pract.* 192:909-918, 1996.

Polosukhin, "Ultrastructural study of the destructive and repair processes in pulmonary inflammation and following endobronchial laser therapy," *Virchows Arch.* 435:13-19, 1999.

Polosukhin, "Ultrastructure of the Blood and Lymphatic Capillaries of the Respiratory Tissue During Inflammation and Endobronchial Laser Therapy," *Ultrastructural Pathology* 24:183-189, 2000.

Provotorov VM, et al., "Clinical Efficacy of Treatment of Patients with Non-Specific Pulmonary Diseases by Using Low-Power Laser Irradiation and Performing Intrapulmonary Drug Administration," *Terapevichesky Arkhiv* 62:18-23, 1991.

Raj, "Editorial," *Pain Practice* 4(1S):S1-S3, 2004.

Ramirez et al., "Sympathetomy in Bronchial Asthma," *J. A. M. A.* 84(26):2002-2003, 1925.

Rienhoff et al., "Treatment of Intractable Bronchial Asthma by Bilateral Resection of the Posterior Pulmonary Plexus," *Arch Surg* 37(3):456-469, 1938.

Savchenko et al., "Adaptation of regulatory physiological systems in surgical treatment of patients with bronchial asthma," *Klin Med (Mosk)* 74(7):38-39, 1996.

Sengupta, "Part 1 Oral cavity, pharynx and esophagus—Esophageal sensory physiology,"*GI Motility online*:17 pages, 2006.

Sepulveda et al., "Treatment of Asthmatic Bronchoconstriction by Percutaneous Low Voltage Vagal Nerve Stimulation: Case Report," *Internet Journal of Asthma, Allergy, and Immunology* 7(2):3 pages, 2009.

Shaari et al., "Rhinorrhea is Decreased in Dogs After Nasal Application of Botulinum Toxin," *Otolaryngol Head Neck Surg* 112(14):566-571, 1992.

Sheski FD, et al., "Cryotherapy, Electrocautery, and Brachytherapy," *Clinics in Chest Medicine* 20(1):123-138, Mar. 1999.

Sil'vestrov et al., "The Clinico-Pathogenetic Validation and Efficacy of the Use of Low-Energy Laser Irradiation and Glucocorticoids in the Treatment of Bronchial Asthma Patients," *Ter Arkh* 63(11), 87-92, 1991.

Simonsson et al., "Role of Autonomic Nervous System and the Cough Reflex in the Increased Responsiveness of Airways in Patients with Obstructive Airway Disease," *The Journal of Clinical Investigation* 46(11): 1812-1818, 1967.

Simpson et al., "Isolation and Characterization of the *Botulinum* Neurotoxins," *Methods Enzymol* 165:76-85, 1988.

Smakov, "Denervation of the lung in the treatment of bronchial asthma," *Khirurgiia (Mosk)* 9:117-120, 1982.
Smakov, "Pathogenetic substantiation of lung denervation in bronchial asthma and it's indications," *Khirurgiia (Mosk)* 2:67-69, 1999.
Smakov, "Prognostication of the effect of therapeutic bronchoscopy in patients with bronchial asthma according to the state of local immunity," *Klin Med (Mosk)* 73(5):76-77, 1995.
Sontag et al., "Asthmatics with Gastroesophageal Reflux: Long-term Results of a Randomized Trial of Medical and Surgical Antireflux Therapies," *Am J Gastroenterol*. 98:987-999, 2003. (Abstract only.).
Stein, "Possible Mechanisms of Influence of Esophageal Acid on Airway Hyperresponsiveness," *Am J Med*. 115(Suppl 3A):55S-59S, 2003. (Abstract only.).
Sundaram et al., "An Experimental and Theoretical Analysis of Ultrasound-Induced Permeabilization of Cell Membranes," *Biophysical Journal* 84:3087-3101, 2003.
Takino et al., "Surgical Removal of the Carotid Body and its Relation to the Carotid Chemoreceptor and Baroreceptor Reflex in Asthmatics," *Dis Chest* 47:129-138, 1965.
Tsugeno et al., "A Proton-Pump Inhibitor, Rabeprazole, Improves Ventilatory Function in Patients with Asthma Associated with Gastroesophageal Reflux," *Scand J Gastroenterol*. 38:456-461, 2003. (Abstract only.).
Tsuji et al., "Biodegradable Stents as a Platform to Drug Loading," *International Journal of Cardiovascular Interventions* 5:13-16, 2003.
Unal et al., "Effect of Botulinum Toxin Type A on Nasal Symptoms in Patients with Allergic Rhinitis: A Double-blind, Placebo-controlled Clinical Trial," *Acta Oto-Laryngologica* 123(9):1060-0163, Dec. 2003.
Van Boxem TJM, et al., "Tissue Effects of Bronchoscopic Electrocautery," *Chest* 117(3):887-891, Mar. 1999.
van der Velden et al., "Autonomic Innervation of Human Airways: Structure, Function, and Pathophysiology in Asthma," *Neuroimmunomodulation* 6:145-159, 1999.
Verhein et al., "Neural Control of Airway Inflammation," *Current Allergy and Asthma Reports* 9:484-490, 2009.
Vorotnev et al., "Treatment of Patients with Chronic Obstructive Bronchitis Using Low Energy Laser at a General Rehabilitation Center," *Therapeutic Archive* 3:17-19, 1997. (+English translation, 4 pages.).
Wahidi et al., "State of the Art: Interventional Pulmonology," *Chest* 131:261-274, 2007.
Weaver, "Electroporation: A General Phenomenon for Manipulating Cells and Tissues," *Journal of Cellular Biochemistry* 51(4):426-435, Apr. 1993.
Wirtz et al., "Bilateral Lung Transplantation for Severe Persistent and Difficult Asthma," *The Journal of Heart and Lung Transplantation* 24(10):1700-1703, 2005.
Laufer, "Method and Apparatus for Treating Smooth Muscles in the Walls of Body Conduits," U.S. Appl. No. 09/095,323, filed Jun. 10, 1998, 25 pages.
Bradley et al., "Effect of vagotomy on the breathing pattern and exercise ability in emphysematous patients," *Clinical Science* 62:311-319, 1982.
Breekveldt-Postma et al., "Enhanced persistence with tiotropium compared with other respiratory drugs in COPD," *Respiratory Medicine* 101:1398-1405, 2007.
Chernyshova et al., "The Effect of Low-Energy Laser Radiation in the Infrared Spectrum on Bronchial Patency in Children With Bronchial Asthma," *Vopr Kurortol, Fizioter Lech Fiz Kult* 2:11-14, 1995.
Chumakov et al., "Morphologic studies of bronchial biopsies in chronic bronchitis before and after treatment," *Arkh Patol* 57(6):21-25, 1995. (See English Abstract on last page.).
Dimitrov-Szokodi et al., "Lung Denervation in the Therapy of Intractable Bronchial Asthma," *J. Thoracic Surg*. 33(2):166-184, Feb. 1957.
Donohue et al., "A 6-Month, Placebo-Controlled Study Comparing Lung Function and Health Status Changes in COPD Patients Treated With Tiotropium or Salmeterol," *Chest* 122:47-55, 2002.
Friedman et al., "Healthcare Costs with Tiotropium Plus Usual Care versus Usual Care Alone Following 1 Year of Treatment in Patients

(56) References Cited

OTHER PUBLICATIONS with Chronic Obstructive Pulmonary Disorder (COPD)," *Pharmacoeconomics* 22(11):741-749, 2004.
George et al., "Factors Associated With Medication Nonadherence in Patients With COPD," *Chest* 128:3198-3204, 2005.
Korochkin et al., "Use of a Helium—Neon Laser in Combined Treatment of Bronchial Asthma," *New Developments in Diagnostics and Treatment*, 1990, 9 pgs.
Løkke et al., "Developing COPD: a 25 year follow up study of the general population," *Thorax* 61:935-939, 2006.
Maesen et al., "Tiotropium bromide, a new long-acting antimuscarinic bronchodilator: a pharmacodynamic study in patients with chronic obstructive pulmonary disease (COPD)," *Eur. Respi. J.* 8:1506-1513, 1995.
Maltais et al., "Improvements in Symptom-Limited Exercise Performance Over 8 h With Once-Daily Tiotropium in Patients With COPD," *Chest* 128:1168-1178, 2005.
O'Connor et al., "Prolonged Effect of Tiotropium Bromide on Methacholine-induced Bronchoconstriction in Asthma," *Am. J. Respir. Crit. Care Med.* 154:876-880, 1996.
Peters et al., "Tiotropium Bromide Step-Up Therapy for Adults with Uncontrolled Asthma," *New England Journal of Medicine* 363(18):1715-1726, Oct. 28, 2010.
Polosukhin, "Dynamics of the ultrastructural changes in blood and lymphatic capillaries of bronchi in inflammation and following endobronchial laser therapy," *Virchows Arch* 431:283-390, 1997.
Polosukhin, "Regeneration of bronchial epithelium on chronic inflammatory changes under laser treatment," *Path. Res. Pract.* 192(9):909-918, 1996.
Polosukhin, "Ultrastructural study of the destructive and repair processes in pulmonary inflammation and following endobronchial laser therapy," *Virchows Arch* 435:13-19, 1999.
Tashkin et al., "Long-term Treatment Benefits With Tiotropium in COPD Patients With and Without Short-term Bronchodilator Responses," *Chest* 123: 1441-1449, 2003.
Vincken et al., "Improved health outcomes in patients with COPD during 1 yr's treatment with tiotropium," *Eur. Respir. J.* 19: 209-216, 2002.
Wagner et al., "Methacholine causes reflex bronchoconstriction," *J. Appl. Physiol.* 86:294-297, 1999.
Montaudon, M., et al., "Assessment of bronchial wall thickness and lumen diameter in human adults using multi-detector computed tomography: comparison with theoretical models," *J. Anat.* 211:579-588, 2007.
Urologix, Inc., "CTC *Advance*™ Instructions for Use," Targis® System Manual, 2010, 8 pages.
Urologix, Inc., "Cooled ThermoTherapy™," 2012, retrieved on Mar. 3, 2005 from URL=http://www.urologix.com/cllinicians/cooled-thermotherapy.php, 2 pages.
Global Strategy for Asthma Management and Prevention, 2002, 192 Pages Total.
James, et al., "The Mechanics of Airway Narrowing in Asthma," *Am. Rev. Respir. Dis.*, 1989, 139, 242-246.
Janssen L. J., "Asthma therapy: how far have we come, why did we fail and where should we go next?," Eur Respir J, 2009, 33, pp. 11-20.
Kitamura S., "Color Atlas of Clinical Application of Fiberoptic Bronchoscopy," 1990, Year Book Medical Publishers, 17.
Kraft M., "The distal airways: are they Important in asthma?," European Respiratory, 1999, 1403-1417.
Notice of final Rejection, Japanese Patent Application No. 2000-553172, dated Sep. 2, 2008, 5 pages.
PCT International search report for application No. PCT/US00/05412 mailed on Jun. 20, 2000, 2 pages.
PCT International search report for application No. PCT/US00/18197 mailed on Oct. 3, 2000, 1 page.
PCT International search report for application No. PCT/US00/28745 mailed on Mar. 28, 2001, 6 pages.
PCT International search report for application No. PCT/US01/32321 mailed on Jan. 18, 2002, 2 pages.
PCT International search report for application No. PCT/US98/03759 mailed on Jul. 30, 1998, 1 page.
PCT International search report for application No. PCT/US98/26227 mailed on Mar. 25, 1999, 1 page.
PCT International search report for application No. PCT/US99/00232 mailed on Mar. 4, 1999, 1 page.
PCT International search report for application No. PCT/US99/12986 mailed on Sep. 29, 1999, 1 page.
Peter K. Jeffery, "Remodeling in Asthma and Chronic Obstructive Lung Disease," American Journal of Respiratory and Critical Care Medicine, 2001, 164 (10), 13516.
Seow C. Y., et al. "Signal Transduction in Smooth Muscle Historical perspective on airway smooth muscle: the saga of a frustrated cell," J Appl Physiol, 2001, 91, 938-952.
Stephanie A.Shore, "Airway Smooth Muscle in Asthma—Not Just More of the Same." N Engl J Med, 2004, 351 (6), 531-532.
UNSW Embryo—Respiratory System [online] Embryology, 2007, [retrieved on Dec. 10, 2007]. Retrieved from the internet: (URL: http://embryology.med.unsw.edu.au/Refer/respire/select.htm).
Wayne Mitzner, "Airway Smooth Muscle Rhe appendix of the Lung," American Journal of Respiratory and Critical Care Medicine, 2004, 169, 787-790.
Wayne Mitzner, "Bronchial Thermoplasty in Asthma," Allergology International, 2006, 55, 225-234.
Non-Final Office Action for U.S. Appl. No. 11/398,353; Mailed on Aug. 31, 2009; 7 pages.
Non-Final Office Action for U.S. Appl. No. 11/398,353; Mailed on Apr. 27, 2010; 8 pages.
Co-pending U.S. Appl. No. 09/244,173.
Co-pending U.S. Appl. No. 09/095,323.
Simon R. Johnson et al., Synthetic Functions of Airway Smooth Muscle in Asthma, Trends Pharmacol. Sci., Aug. 1997, 18(8), 288-292.
MacKlem P.T., Mechanical Factors Determining Maximum Bronchoconstriction, European Respiratory Journal, Jun. 1989, 6, 516s-519s.
James C. Hogg, The Pathology of Asthma, APMIS, Oct. 1997, 105(10), 735-745.
Dierkesmann et al., Indication and Results of Endobronchial Laser Therapy, Lung, 1990, 168, 1095-1102.
Netter F.H., Respiratory System: A Compilation of Paintings Depicting Anatomy and Embryology, Physiology, Pathology, Pathophysiology, and Clinical Features and Treatment of Diseases, In The CIBA Collection of Medical Illustrations M.B. Divertie, ed., Summit: New Jersey, 1979, vol. 7, 119-135.
Provotorov et al.; The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 63 (12), 18-23.
Wiggs B.R. et al., On the Mechanism of Mucosal Folding in Normal and Asthmatic Airways, J. Appl. Physiol., Dec. 1997, 83(6), 1814-1821.
An, S. S. et al., Airway smooth muscle dynamics; a common pathway of airway obstruction in asthma, European Respiratory Journal, 2007, vol. 29, No. 5, pp. 834-860.
Bel, E, H., Hot Stuff: Bronchial Thermoplasty for Asthma, American Journal of Respiratory and Critical Care Medicine, 2006, vol. 173, pp. 941-942.
Brown, R. H. et al., In vivo evaluation of the effectiveness of bronchial thermoplasty with computed tomography. Journal of Applied Physiology, 2005, vol. 98, pp. 1603-1606.
Chhajed, P., Will There be a Role for Bronchoscopic Radiofrequency Ablation?, 2005, J Bronchol, vol. 12, No. 3, p. 184.
Cox, G., et al, . Early Clinical Experience With Bronchial Thermoplasty for the Treatment of Asthma, 2002, p. 1068.
Cox, G. et al., Asthma Control During the Year After Bronchial Thermoplasty, The New England Journal of Medicine, Mar. 29, 2007, vol. 356, No. 13, pp. 1327-1337.
Cox. G. et al., Bronchial Thermoplasty: One-Year Update, American Thoracic Society Annual Meeting, 2004, p. 1.
Cox, G., et al., Development of a Novel Bronchoscope Therapy for Asthma, Journal of Allergy and Clinical Immunology, 2003, p. 1.

(56) References Cited

OTHER PUBLICATIONS

Cox, G., et al., Bronchial Thermoplasty for Asthma, American Journal of Respiratory and Critical Care Medicine, 2006, vol. 173, pp. 965-969.
Cox, G., et al., Bronchial Thermoplasty: Long-Term Follow-up and Patient Satisfaction, 2004, p. 1.
Cox, G., et al., Radiofrequency ablation of airway smooth muscle for sustained treatment of asthma: preliminary investigations, European Respiratory Journal, 2004, 24, pp. 659-663.
Cox, G., et al., Clinical Experience with Bronchial Thermoplasty for the Treatment of Asthma, 2003, Chest 124, p. 106S.
Cox, G., et al., Impact of bronchial thermoplasty on asthma status: interim results from the AIR trial, 2006, European Respiratory Society Annual. Meeting, Munich, Germany, p. 1.
Danek, C. J., et al., Bronchial thermoplasty reduces canine airway responsiveness to local methacholine challenge, 2002, American Thoracic Society Annual Meeting, p. 1.
Danek, C. J., et al., Asthma Intervention Research (AIR) Trial Evaluating Bronchial Thermoplasty™; Early Results, 2002, American Thoracic Society Annual Meeting, p. 1.
Danek, C. J., et al., Reduction in airway hyperresponsiveness to methacholine by the application of RF energy in dogs, J Appl Physiol, 2004, vol. 97, pp. 1946-1933.
Solway, J. et al., Airway Smooth Muscle as a Target for Asthma Therapy, The New England Journal of Medicine, Mar. 29, 2007, 356(13), pp. 1367-1369.
Lavioletts, et al. Asthma Intervention Research (AIR) Trial: Early Safety Assessment of Bronchial Thermoplasty, 2004, p. 1.
Leff et al., Bronchial Thermoplasty Alters Airway Smooth Muscle and Reduces Responsiveness in Dogs; A Possible Procedure for the Treatment of Asthma, American Thoracic Society Annual Meeting, 2002, p. 1.
Lim, E.E. et al., Botulinum Toxin: A Novel Therapeutic Option for Bronchial Asthma?, Medical Hypotheses, 2006, vol. 66, pp. 915-919.
Lombard, et al, Histologic Effects of Bronchial Thermoplasty of Canine and Human Airways, American Thoracic Society Annual Meeting, 2002, p. 1.
Mayse, M. et al., Clinical Pearls for Bronchial Thermoplasty, J Bronchol, Apr. 2007, vol. 14, No. 2, pp. 115-123.
Miller. J. D. et al., A Prospective Feasibility Study of Bronchial Thermoplasty in the Human Airway. 2005. vol. 127, No. 6 pp. 1999-2006.
Miller, J. D. et al., Bronchial Thermoplasty is Well Tolerated by Non-Asthmatic Patients Requiring Lobectomy, 2002, American Thoracic Society Annual Meeting, p. 1.
Rubin, et al., Bronchial Thermoplasty improves Asthma Status of Moderate to Severe Persistent Asthmatics Over and Above Current Standard-of-Care, 2006, American College of Chest Physicians, 2 pages.
Sterk, P. J., Heterogeneity of Airway Hyperresponsiveness: Time for Unconventional, but Traditional Studies, 2004, The American Pshychoiogical Society, pp. 2017-2018.
Wilson, S. R. et al., Global assessment after bronchial thermoplasty: the patient's perspective, Journal of Outcomes Research, 2006, vol. 10, pp. 37-46.
Toma, T. P., Brave New World for Interventional Bronchoscopy, 2005, Thorax, vol. 60, pp. 180-181.
Trow, T., Clinical Year in Review I, proceedings of the American Thoracic Society, 2006, vol. 3, pp. 553-556.
Wizeman, et al., A Computer Model of Thermal Treatment of Airways by Radiofrequency (RF) Energy Delivery, 2007, American Thoracic Society Annual Meeting, p. 1.
Shesterina. M. V. et al., Effect of laser therapy on immunity in patients with bronchial asthma and pulmonary tuberculosis, 1993, pp. 23-26.
Evis Exera Bronchovideoscope Brochure, Olympus BF-XT160, Olympus, Jun. 15, 2007, 2 pages.
Accad, M., "Single-Step Renal Denervation With the OneShot™ Ablation System," presentation at the Leipzig Interventional Course 2012 in Leipzig, Germany, Jan. 26, 2012, 11 pages.
Bertog, S., "Covidien-Maya: OneShot™," presentation at the 2012 Congenital & Structural Interventions Congress in Frankfurt, Germany, Jun. 28, 2012, 25 pages.
Rocha-Singh, K.J., "Renal Artery Denervation: A Brave New Frontier," Endovascular Today, Feb. 2012, pp. 45-53.
Wilson, K.C., et al., "Flexible Bronchoscopy: Indications and Contraindications," UpToDate, Nov. 12, 2010 <www.uptodate.com> [retrieved Sep. 30, 2012], 15 pages.
Gaude, G.S., "Pulmonary Manifestations of Gastroesophageal Reflux Disease," *Annals of Thoracic Medicine* 4(3):115-123, Jul.-Sep. 2009.
Awadh, N., et al. "Airway Wall Thickness in Patients With Near Fatal Asthma and Control Groups: Assessment With High Resolution Computed Tomographic Scanning," *Thorax* 53:248-253, 1998.
Castro, M., et al., "Effectiveness and Safety of Bronchial Thermoplasty in the Treatment of Severe Asthma: A Multicenter, Randomized, Double-Blind, Sham-Controlled Clinical Trial," *American Journal of Respiratory and Critical Care Medicine* 181: 116-124, 2010.
Martin, N., et al., "Bronchial Thermoplasty for the Treatment of Asthma," *Current Allergy and Asthma Reports* 9(1):88-95, Jan. 2009.
McEvoy, C.E., et al., "Changing the Landscape: Bronchial Thermoplasty Offers a Novel Approach to Asthma Treatment," *Advance for Managers of Respiratory Care*, pp. 22, Oct. 24-25, 2007.
Michaud, G., et al., "Positioned for Success: Interest in Diagnostic and Therapeutic Bronchoscopy is Growing," *Advance for Managers of Respiratory Care*, pp. 40, 42-43, Jul./Aug. 2008.
O'Sullivan, M.P., et al., "Apoptosis in the Airways: Another Balancing Act in the Epithelial Program," *American Journal of Respiratory Cell and Molecular Biology* 29:3-7, 2003.
Pavord, I.D., et al., "Safety and Efficacy of Bronchial Thermoplasty in Symptomatic, Severe Asthma," *American Journal of Respiratory and Critical Care Medicine* 176:1185-1191, 2007.
Tschumperlin, D.J., et al., "Chronic Effects of Mechanical Force on Airways," *Annual Review of Physiology* 68: 563-83, 2006.
Tschumperlin, D.J., et al., "Mechanical Stimuli to Airway Remodeling," *American Journal of Respiratory and Critical Care Medicine* 164:S90-S94, 2001.
Wechsler, M.E., "Bronchial Thermoplasty for Asthma: A Critical Review of a New Therapy," *Allergy and Asthma Proceedings* 29(4):1-6, Jul.-Aug. 2008.
Co-Pending U.S. Appl. No. 13/523,223, filed Jun. 14, 2012, Edwin J. Hlavka et al.
Preliminary Amendment and Response to Restriction Requirement filed Oct. 22, 2012, in co-pending U.S. Appl. No. 13/523,223, filed Jun. 14, 2012, Edwin J. Hlavka et al.
Co-Pending U.S. Appl. No. 12/372,607, filed Feb. 17, 2009, Edwin J. Hlavka et al.
Amendment After Allowance filed Sep. 17, 2012, in co-pending U.S. Appl. No. 12/372,607, filed Feb. 17, 2009, Edwin J. Hlavka et al.
Application and File History for U.S. Appl. No. 12/463,304, filed May 8, 2009, inventors Mayse et al.
Application and File History for U.S. Appl. No. 13/245,522, filed Sep. 26, 2011, inventors Mayse et al.
Application and File History for U.S. Appl. No. 13/452,664, filed Apr. 20, 2012, inventors Mayse et al
Application and File History for U.S. Appl. No. 13/592,075, filed Aug. 22, 2012, inventors Mayse et al.
Application and File History for U.S. Appl. No. 13/452,648, filed Apr. 20, 2012, inventors Mayse et al.
Application and File History for U.S. Appl. No. 13/452,655, filed Apr. 20, 2012, inventors Mayse et al.
Application and File History for U.S. Appl. No. 12/913,702, filed Oct. 27, 2010, inventors Mayse et al.
Application and File History for U.S. Appl. No. 13/931,208, filed Jun. 28, 2013, inventors Mayse et al.
Application and File History for U.S. Appl. No. 13/509,581, filed Aug. 14, 2012, inventors Dimmer et al.
Application and File History for U.S. Appl. No. 13/245,537, filed Sep. 26, 2011, inventors Mayse et al.
Application and File History for U.S. Appl. No. 13/452,660, filed Apr. 20, 2012, inventors Mayse et al.

(56) References Cited

OTHER PUBLICATIONS

Application and File History for U.S. Appl. No. 13/930,825, filed Jun. 28, 2013, inventors Mayse et al.

Application and File History for U.S. Appl. No. 13/931,246, filed Jun. 28, 2013 inventors Mayse et al.

Application and File History for U.S. Appl. No. 13/894,920, filed May 15, 2013, inventors Mayse et al.

Third party submission filed on Apr. 2, 2014, in U.S. Appl. No. 14/024,371, inventors Kaplan et al.

Brown, R.H. et al., Effect of bronchial thermoplasty on airway distensibility, European Respiratory Journal, vol. 26, No. 2, pp. 277-282; Aug. 2005.

Vasilotta, P.I. et al., "I-R Laser: A new Therapy in Rhino-Sino-Nasal Bronchial Syndrome with Asthmatic Component," American Society for Laser medicine and Surgery abstracts; 1 page, facsimile copy dated Feb. 8, 2007.

Office Action for Chinese Application No. 201080048938.0, dated Jun. 27, 2014 (11 pages).

Office Action for Japanese Application No. 2012-537018, known to applicant at least as of Jul. 11, 2014 (3 pages.).

Application and File History for European Patent Application No. 09 743 805.5 filed May 8, 2009; inventors Dimmer et al., as available on EPO Register at https://register.epo.org.

Application and File History for European Patent Application No. 12 005 299.8 filed Jul. 18, 2012; inventors Dimmer et al., as available on EPO Register at https://register.epo.org.

Application and File History for European Patent Application No. 13 003 665.0 filed Jul. 22, 2013; inventors Dimmer et al., as available on EPO Register at https://register.epo.org.

Application and File History for European Patent Application No. 13 003 667.6 filed Jul. 22, 2013; inventors Dimmer et al., as available on EPO Register at https://register.epo.org.

Application and File History for European Patent Application No. 13 003 666.8 filed Jul. 22, 2013; inventors Dimmer et al., as available on EPO Register at https://register.epo.org.

Application and File History for European Patent Application No. 10 774 097.9 filed Oct. 27, 2010; inventors Mayse et al., as available on EPO Register at https://register.epo.org.

Application and File History for European Patent Application No. 10 779 422.4 filed Nov. 11, 2010; inventors Dimmer et al., as available on EPO Register at https://register.epo.org.

\* cited by examiner

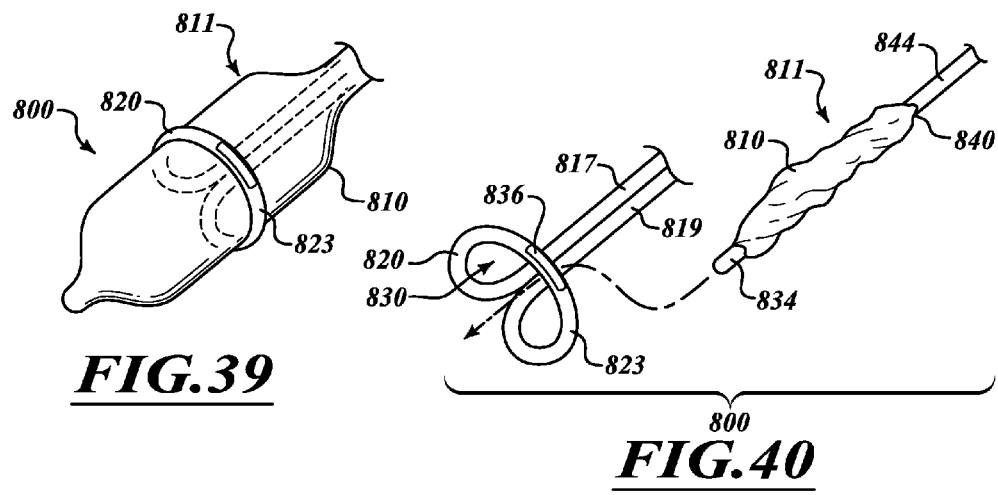
FIG.39
FIG.40
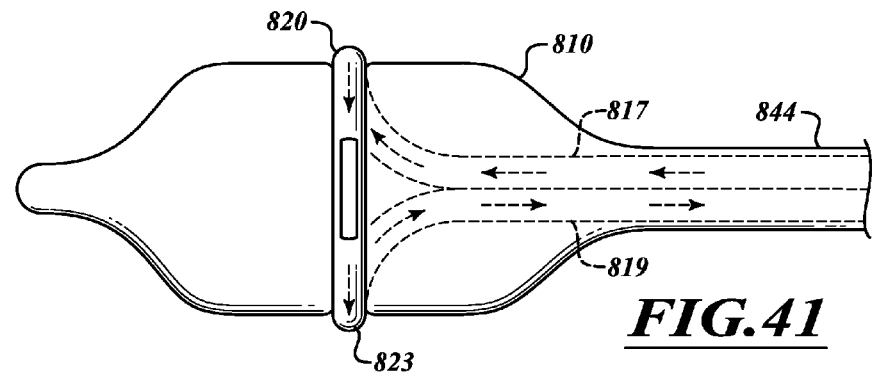
FIG.41
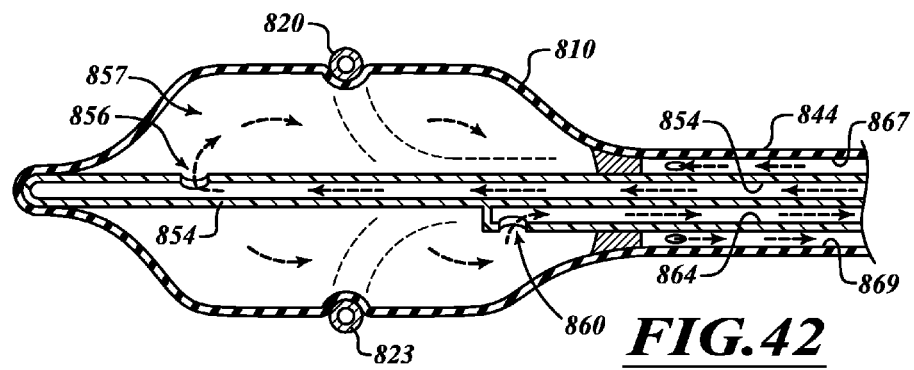
FIG.42

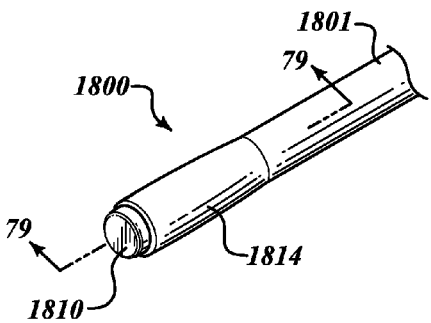
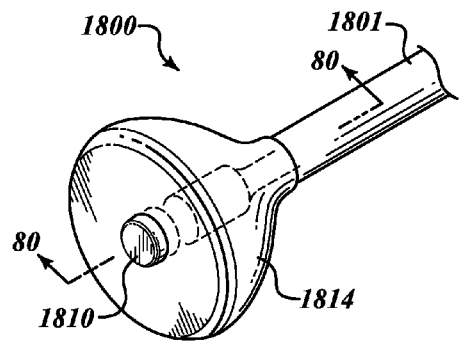
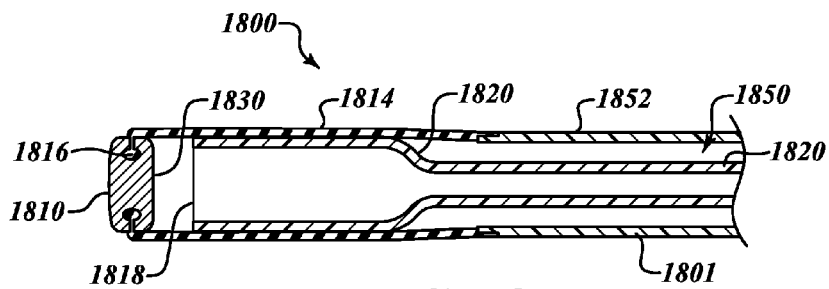
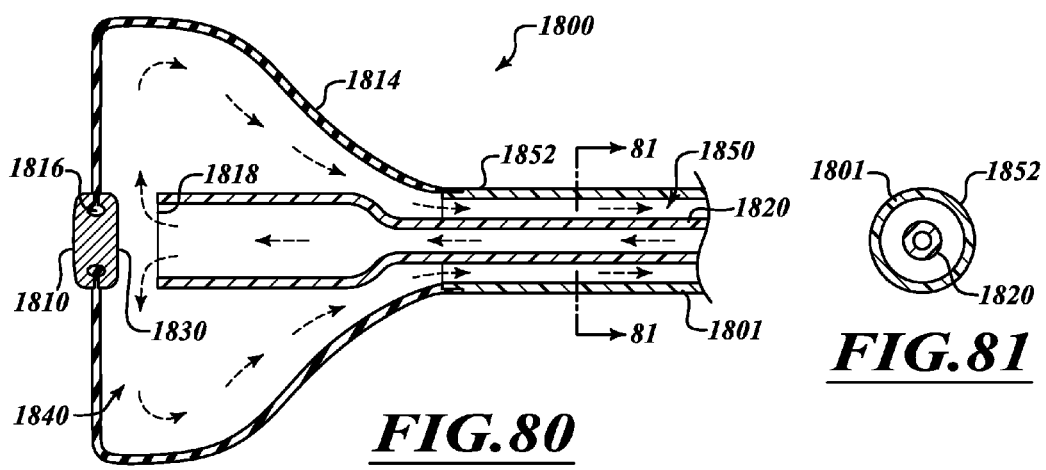

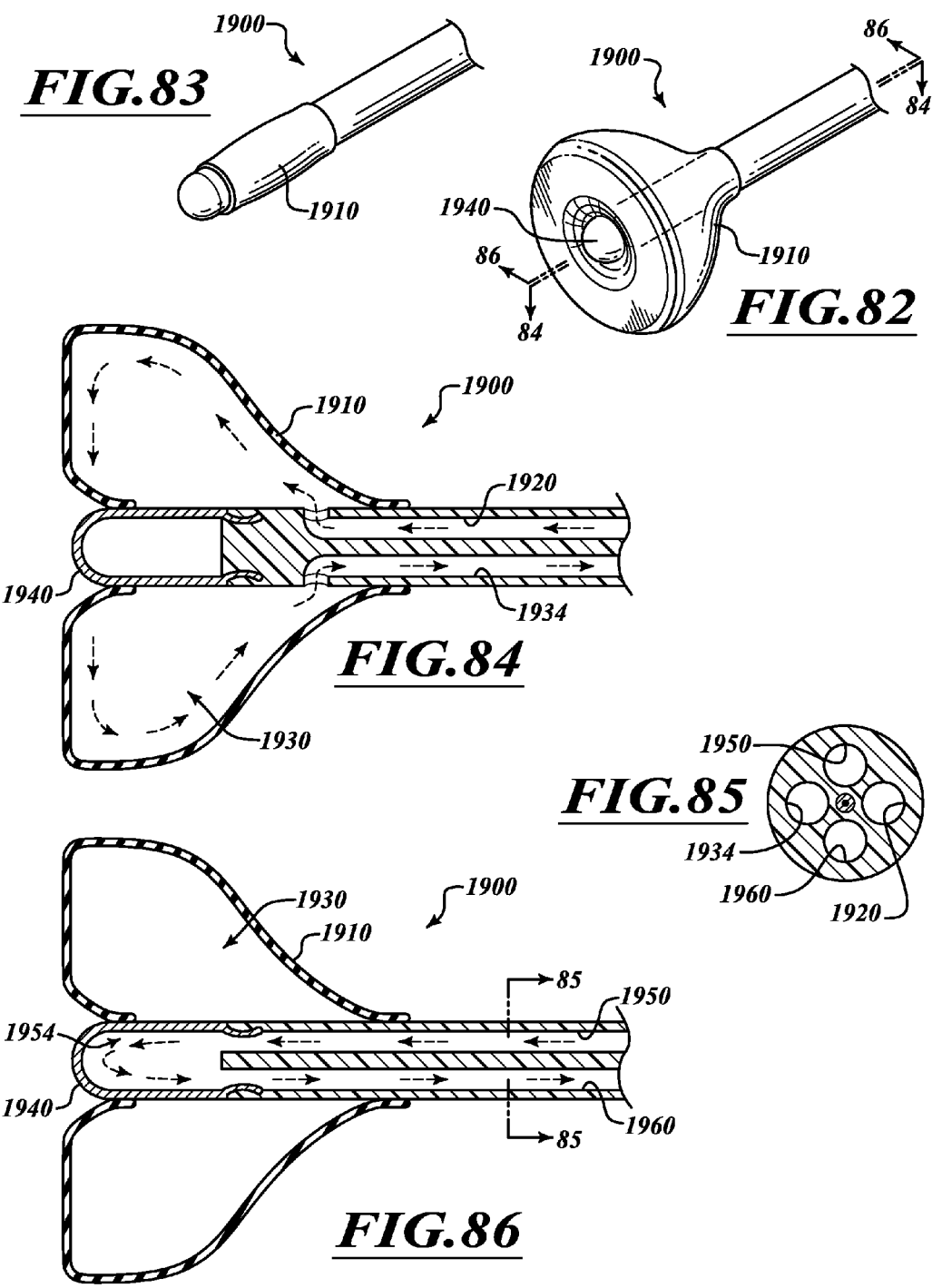

DELIVERY DEVICES WITH COOLABLE ENERGY EMITTING ASSEMBLIES

CROSS-REFERENCES TO RELATED APPLICATIONS

This application is a continuation of U.S. patent application Ser. No. 12/913,702 filed Oct. 27, 2010, which claims the benefit under 35 U.S.C. §119(e) of U.S. Provisional Patent Application No. 61/255,367 filed Oct. 27, 2009 and U.S. Provisional Patent Application No. 61/260,348 filed Nov. 11, 2009. Each of these applications is incorporated herein by reference in its entirety.

BACKGROUND

1. Technical Field

The present invention generally relates to systems, apparatuses, and methods for treating tissue, and more particularly, the invention relates to systems or treatment systems with delivery devices having coolable energy emitting assemblies for eliciting a desired response.

2. Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands), and the central nervous system input (nervous system signals from the brain to smooth muscle cells and mucous glands carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable to deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Different techniques can be used to assess the severity and progression of pulmonary diseases. For example, pulmonary function tests, exercise capacity, and quality of life questionnaires are often used to evaluate subjects. Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation during the first second. A FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway would be defined as the ratio of the pressure gradient across the given airway to the flow through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six minute walk test (6 MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer. The patient can breathe 30 percent oxygen and the work load can increase by 5-10 watts every 3 minutes.

Quality of life questionnaires assess a patient's overall health and well being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

Treatments, such as bronchial thermoplasty, involve destroying smooth muscle tone by ablating the airway wall in a multitude of bronchial branches within the lung thereby eliminating both smooth muscles and nerves in the airway walls of the lung. The treated airways are unable to respond favorably to inhaled irritants, systemic hormones, and both local and central nervous system input. Unfortunately, this destruction of smooth muscle tone and nerves in the airway wall may therefore adversely affect lung performance. For example, inhaled irritants, such as smoke or other noxious substances, normally stimulate lung irritant receptors to produce coughing and contracting of airway smooth muscle. Elimination of nerves in the airway walls removes both local nerve function and central nervous system input, thereby eliminating the lung's ability to expel noxious substances with a forceful cough. Elimination of airway smooth muscle tone may eliminate the airways' ability to constrict, thereby allowing deeper penetration of unwanted substances, such as noxious substances, into the lung.

Both asthma and COPD are serious diseases with growing numbers of sufferers. Current management techniques, which include prescription drugs, are neither completely successful nor free from side effects. Additionally, many patients do not comply with their drug prescription dosage regiment. Accordingly, it would be desirable to provide a treatment which improves resistance to airflow without the need for patient compliance.

BRIEF SUMMARY

In some embodiments, a treatment system can be navigated through airways, such as the right and left main bronchi of the lung root, as well as more distal airways within the lungs, to treat a wide range of pulmonary symptoms, conditions, and/or diseases, including, without limitation, asthma, COPD, obstructive lung diseases, or other diseases that lead to an increased resistance to airflow in the lungs. A collapsible ablation assembly can be conveniently passed through airways. An energy emitter assembly of the ablation assembly can treat one or more target sites without treating non-targeted sites. Even if targeted anatomical features (e.g., nerves, glands, membranes, and the like) of main bronchi, lobar bronchi, segmental bronchi or subsegmental bronchi are treated, non-targeted anatomical features can be substantially unaltered. For example, the treatment system can destroy nerve tissue at target sites without destroying to any significant extent non-targeted tissue that can remain functional after performing treatment. The energy emitter assembly is coolable to avoid or limit destruction of non-targeted tissue.

In some embodiments, a system for treating a subject includes a delivery device configured to move along a lumen of an airway of a bronchial tree. The delivery device can form lesions to attenuate signals transmitted by nerve tissue, such as nerve tissue of nerve trunks, while not irreversibly damaging to any significant extent non-targeted features, such as an inner surface or smooth muscle of the airway. The delivery device can include a distal tip with at least one ablation assembly.

The ablation assembly, in some embodiments, can be moved from a low-profile configuration for delivery to a deployed configuration for treating tissue at a target region. Ablation elements can be activated to ablate tissue. Each ablation element can include one or more electrodes operable to output ultrasound, electrical energy, and/or radiofrequency (RF) energy. In certain embodiments, each electrode is a fluid coolable electrode.

In other embodiments, a delivery device is a catheter with a collapsible energy emitter assembly. An expandable element, or other biasing feature, presses the energy emitter assembly against an airway wall. The energy emitter assembly delivers energy to targeted tissue. In certain embodiments, the energy emitter assembly and the expandable element are expanded simultaneously. In other embodiments, the expandable element is expanded before or after the energy emitter assembly is deployed.

In some embodiments, a method comprises damaging nerve tissue of a first main bronchus to substantially prevent nervous system signals from traveling to substantially all distal bronchial branches connected to the first main bronchus. In some embodiments, most or all of the bronchial branches distal to the first main bronchus are treated. The damaged nerve tissue, in certain embodiments, is positioned between a trachea and the lung through which the bronchial branches extend. The method can further include damaging nerve tissue of a second main bronchus to substantially prevent nervous system signals from traveling to substantially all distal bronchial branches connected to the second main bronchus.

At least some embodiments can denervate the lung bronchus by creating lesions using radiofrequency ablation. Ablating nerve trunks which traverse along the outside of both the right and left main bronchi effectively disconnects airway smooth muscle which lines the inside of the lung airways and mucus producing glands located with the airways from the vagus nerve and central nervous system. When this occurs, airway smooth muscle relaxes and mucus production is decreased. These changes reduce airway obstruction under states of disease, such as COPD and asthma. Reduced airway obstruction makes breathing easier which can improve patient quality of life and health status.

The lesions can be shaped or modified using differential temperature control. Differential temperature control can involve independent cooling of different features of a delivery device, such as an ablation assembly, an expandable element, or an energy emitter assembly. Differential cooling is used to increase or maximize lesion depth. In some procedures, nerve tissue and other structures (e.g., adjacent tissue structures, organs or diseased tissue such as cancerous or non-cancerous tumors, etc.) are part of the target region. Additionally or alternatively, differential cooling can be used to control (e.g., limit or minimize) or eliminate shallow or surface tissue damage.

Lesions can be formed at target regions. Target regions can include, without limitation, nerve tissue (e.g., tissue of the vagus nerves, nerve trunks, etc.), fibrous tissue, diseased or abnormal tissues (e.g., cancerous tissue, inflamed tissue, and the like), cardiac tissue, muscle tissue, blood, blood vessels, anatomical features (e.g., membranes, glands, cilia, and the like), or other sites of interest. In RF ablation, heat is generated due to the tissue resistance as RF electrical current travels through the tissue. The tissue resistance results in power dissipation that is equal to the current flow squared times the tissue resistance. To ablate deep tissues, tissue between an RF electrode and the deep tissue can become heated if active cooling is not employed. Electrode cooling can be used to keep tissue near the electrode below a temperature that results in cell death or damage, thereby protecting tissue. For example, cooling can prevent or limit overheating at the electrode-tissue interface. Overheating (e.g., tissue at temperatures above 95° C. to about 110° C.) can lead to the formation of coagulum, tissue desiccation, tissue charring, and explosive outgassing of steam. These effects can result in increased tissue resistance and reduced RF energy transfer into the tissue, thereby limiting the effective RF ablation lesion depth. Active cooling can be used to produce significantly deeper tissue lesions. The temperature of coolant for active cooling can be about 0° C. to about 24° C. In some embodiments, the coolant and electrode produce a lesion at a therapeutic depth of at least about 3 mm. In some embodiments, the lesions can be formed at a depth of about 3 mm to about 5 mm to damage nerve tissue.

Sensors, in some embodiments, are used to monitor temperatures, inflation pressures, coolant flow rates, tissue impedance, or other parameters of interest. Feedback from the sensors can be used to modulate the power delivered to electrode(s). Outputted energy can be adjusted to account for local variations in tissue that alters the local impedance, thus avoiding excess heating which can lead to unwanted hot spots. Lesions can also be formed independent of regional tissue characteristics.

In some embodiments, a delivery device comprises an ablation assembly and a deployable element including a deployable element movable from a collapsed state to an expanded state to bring the tissue-contacting portion of the energy emitter assembly ablation assembly into contact with tissue, such as an airway wall, cardiac tissue or the like.

The energy emitter assembly, in some embodiments, is configured to output energy to ablate targeted tissue of a bronchial tree and through which a coolant is capable of flowing so as to cool a tissue-contacting portion of the energy emitter assembly. A cooling section is configured to contain the coolant and is movable into contact with the airway wall so as to cool tissue adjacent to the tissue-contacting portion of the energy emitter assembly when energy is being outputted therefrom. The deployable element is configured to contain the coolant such that the coolant cools the energy emitter assembly and the deployable element when the deployable element is in the expanded state and the ablation assembly is in contact with the airway wall to limit or prevent damage to tissue between the ablation assembly and the targeted tissue. An elongate shaft is coupled to the ablation assembly and provides coolant flow to the ablation assembly and receives coolant from the ablation assembly.

A controller can be communicatively coupled to a fluid delivery system and communicatively coupled to a sensor of the ablation assembly. The controller is configured to command the fluid delivery system based on at least one signal from the sensor. The controller is configured to execute at least one differential cooling program to deliver the first fluid at a significantly different temperature from the temperature of the second fluid. The temperature difference can be at least about 5, 10, 20, or 30 degrees C.

In certain embodiments, a delivery device includes an ablation assembly including an energy emitter assembly configured to output energy to ablate targeted tissue of a bronchial tree and through which a coolant is capable of flowing so as to cool a tissue-contacting portion of the energy emitter assembly and a deployable element movable from a collapsed state to an expanded state to bring the tissue-contacting portion of the energy emitter assembly into contact with an airway wall of the bronchial tree. A cooling section is configured to contain the coolant and movable into contact with the airway wall so as to cool tissue adjacent to the tissue-contacting portion of the energy emitter assembly when energy is being outputted therefrom. An elongate shaft is coupled to the ablation assembly. Coolant can flow through the shaft to the ablation assembly.

In some embodiments, a delivery device includes an ablation assembly including an electrode configured to output energy to ablate targeted tissue of an airway. The electrode is movable between a first orientation in which the electrode extends axially along the airway and a second orientation in which the entire electrode is disposed in a space between adjacent cartilage rings of the airway.

A delivery device, in some embodiments, includes a deployable element movable between a collapsed state and an expanded state. An intercartilaginous energy emitter assembly surrounds at least a portion of the deployable element. At least a portion of the energy emitter assembly is moveable with respect to the deployable element in the expanded state to urge an electrode of the energy emitter assembly between adjacent cartilage rings of an airway wall of a bronchial tree.

In yet other embodiments, a delivery device includes an ablation assembly including an energy emitter assembly and an inflatable cooling balloon. The energy emitter assembly includes a cooling channel. The inflatable cooling balloon includes a cooling chamber. An elongate shaft is configured to independently deliver a first fluid to the cooling channel and a second fluid to the cooling chamber.

A delivery device includes an elongate shaft and ablation assembly coupled to the elongate shaft. The ablation assembly, in some embodiments, includes an electrode capable of emitting ablation energy and having a first end, a second end, and a main body between the first end and the second end. At least one of the first end and the second end is covered by an ablation energy insulator, which can be a shield.

A treatment system includes a delivery device configured to deliver energy to a first tissue surface proximate the delivery device to damage a target region of tissue such that a portion of the target region defining a maximum cross-sectional width of the target region is separated from the first tissue surface.

A method of treating a subject including moves a cooling element of a delivery device through a receiving-opening of an energy emitter assembly located in an airway of the subject. The cooling element is expanded to position at least a portion of the energy emitter assembly between the cooling element and a wall of the airway. Energy is delivered from the energy emitter assembly to ablate tissue in the wall of the airway while coolant flows through the expanded cooling element and the energy emitter assembly.

A method of treating a subject includes moving an ablation assembly into an airway of a bronchial tree. The ablation assembly includes a cooling element and an energy emitter assembly. The cooling element is expanded to contact a wall of the airway with the cooling element. Energy is delivered from the energy emitter assembly to damage nerve tissue of a nerve trunk extending along the airway. Coolant flows into contact with at least a portion of the energy emitter assembly while delivering the energy to cool a wall of the airway to limit or prevent cell death in tissue located between the damaged nerve tissue and the ablation assembly.

A method of treating a subject includes positioning an ablation assembly of a delivery device within an airway. Energy is from an electrode of the ablation assembly to damage nerve tissue of a nerve trunk such that nervous system signals transmitted to a portion of the bronchial tree are attenuated. Coolant is delivered through a channel of the electrode of the ablation assembly.

A method of treating tissue includes delivering energy to the tissue from a delivery device positioned near a first surface of the tissue. The energy damages a target region such that a portion of the target region defining a maximum cross-sectional width of the target region is separated from the first surface.

A method of delivering energy includes delivering energy from an electrode with a substantially uniform voltage across the electrode surface in contact with the tissue without contacting the tissue with edges of the electrode. The electrode can comprise a plurality of sub-electrodes that can be independently operated in a desired sequence.

BRIEF DESCRIPTION OF THE DRAWINGS

In the Figures, identical reference numbers identify similar elements or acts.

FIG. 39 is an isometric view of a multi-component ablation assembly.

FIG. 40 is an isometric view of an expandable element ready to be inserted through a loop of an energy emitter assembly.

FIG. 41 is a side elevational view of the ablation assembly of FIG. 39.

FIG. 42 is a longitudinal cross-sectional view of the ablation assembly of FIG. 39.

FIG. 77 is an isometric view of a delivery device with a distally distensible, expandable element carrying an electrode.

FIG. 78 is an isometric view of the expandable element in an inflated state.

FIG. 79 is a cross-sectional view of the ablation assembly taken along a line 79-79 of FIG. 77.

FIG. 80 is a cross-sectional view of the delivery device taken along a line 80-80 of FIG. 78.

FIG. 81 is a cross-sectional view of an elongate body taken along a line 81-81 of FIG. 80.

FIG. 82 is an isometric view of a delivery device with an independently cooled distally distensible, expandable element and electrode.

FIG. 83 is an isometric view of the distally distensible, expandable element in a delivery configuration.

FIG. 84 is a cross-sectional view of the delivery device taken along a line 84-84 of FIG. 82.

FIG. 85 is a cross-sectional view of an elongate body of FIG. 86 taken along a line 85-85.

FIG. 86 is a cross-sectional view of the delivery device taken along a line 86-86 of FIG. 82.

DETAILED DESCRIPTION

Figure 1:
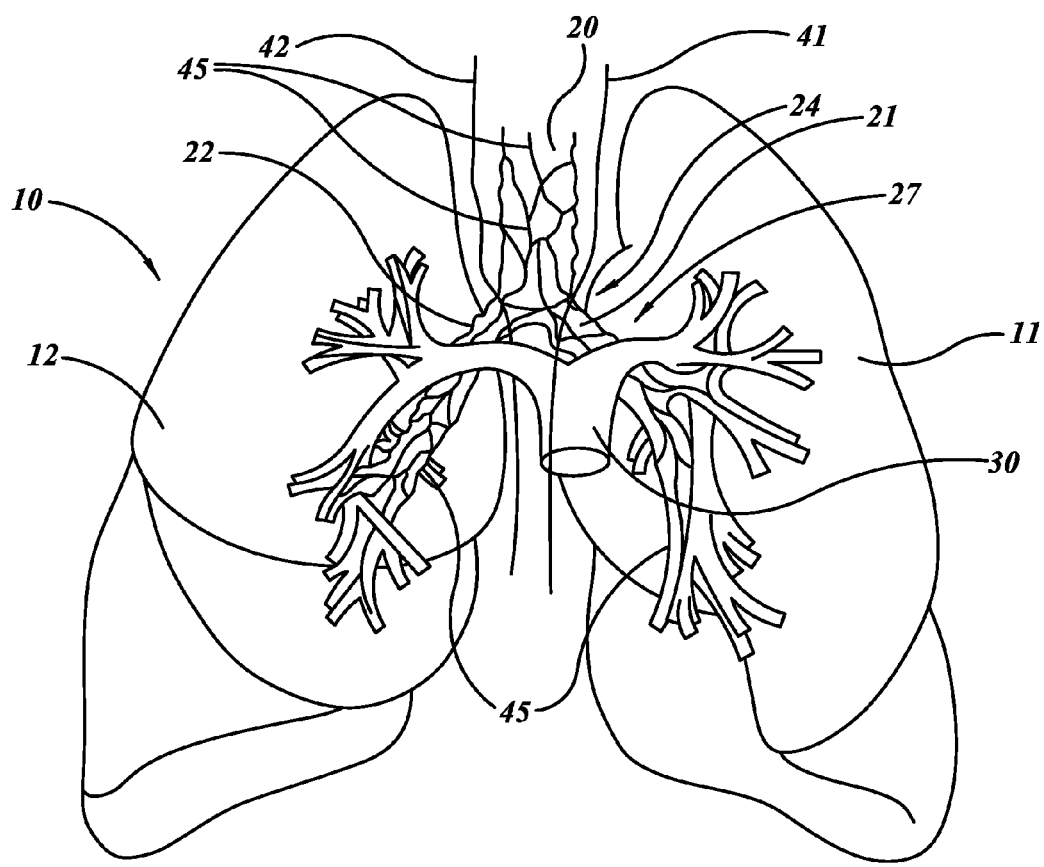
FIG. 1 is an illustration of lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen enriched blood then flows from the alveolar capillaries through the branching blood vessels of the pulmonary venous system to the heart. The heart pumps the oxygen rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

Figure 2:
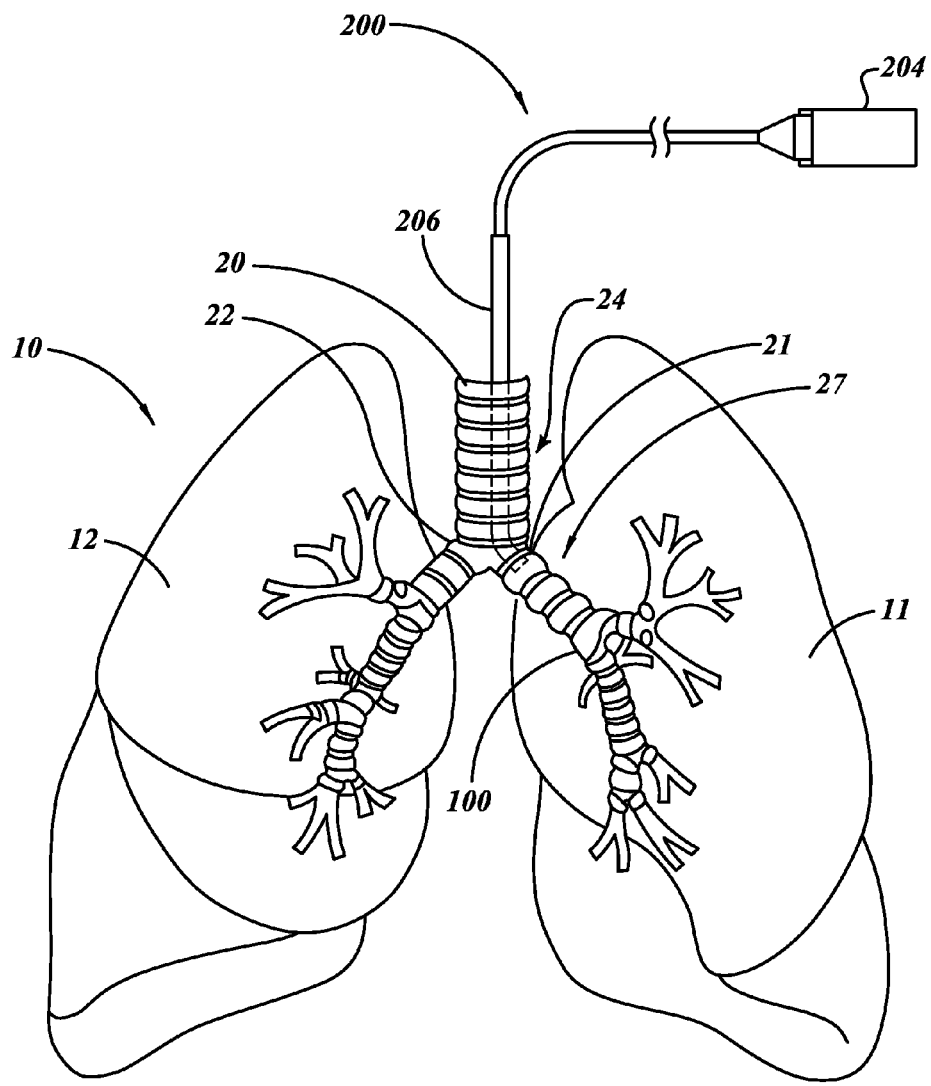
FIG. 2 is an illustration of an intraluminal treatment system positioned within a left main bronchus according to one embodiment.

FIG. 2 shows a treatment system 200 capable of performing treatments to adjust air flow during expiration or inhalation, or both. To decrease air flow resistance to increase gas exchange, the treatment system 200 can be used to enlarge (e.g., dilate) airways. In some procedures, nerve tissue, such as nerve tissue of a nerve trunk inside or outside of the lungs, can be affected to dilate airways. The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

Any number of procedures can be performed on one or more of these nerve trunks 45 to affect the portion of the lung associated with those nerve trunks. Because some of the nerve tissue in the network of nerve trunks 45 coalesce into other nerves (e.g., nerves connected to the esophagus, nerves though the chest and into the abdomen, and the like), the treatment system 200 can treat specific sites to minimize, limit, or substantially eliminate unwanted damage of those other nerves. Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 4 and 5. Various procedures that may be performed with at least some of the devices and methods of the present invention are described in copending application Ser. No. 12/463,304 filed on May 8, 2009, which is incorporated herein by reference in its entirety.

The treatment system 200 can affect specific nerve tissue, such as vagus nerve tissue, associated with particular sites of interest. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion. The treatment system 200 can affect the efferent and/or the afferent tissues to control airway smooth muscle (e.g., innervate smooth muscle), mucous secretion, nervous mediated inflammation, and tissue fluid content (e.g., edema). The contraction of airway smooth muscle, excess mucous secretion, inflammation, and airway wall edema associated with pulmonary diseases often results in relatively high air flow resistance causing reduced gas exchange and decreased lung performance.

In certain procedures, the treatment system 200 can be used to attenuate the transmission of signals traveling along the vagus nerves 41, 42 that cause or mediate muscle contractions, mucus production, inflammation, edema, and the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. Decreasing or stopping sensory input from the airways and lungs to local effector cells or to the central nervous system can also decrease reflex bronchoconstriction, reflex mucous production, release of inflammatory mediators, and nervous system input to other cells in the lungs or organs in the body that may cause airway wall edema. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. In some embodiments, the airway inflammation can be decreased a sufficient amount to cause a substantial decrease in airflow resistance and ongoing inflammatory injury to the airway wall. Signal attenuation may allow the smooth muscles to relax, prevent, limit, or substantially eliminate mucus production by mucous producing cells, and decrease inflammation. In this manner, healthy and/or diseased airways can be altered to adjust lung function. After treatment, various types of questionnaires or tests can be used to assess the subject's response to the treatment. If needed or desired, additional procedures can be performed to reduce the frequency of coughing, decrease breathlessness, decrease wheezing, and the like.

Main bronchi 21, 22 (i.e., airway generation 1) of FIGS. 1 and 2 can be treated to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness. Because the bronchial arteries in the main bronchi 21, 22 have relatively large diameters and high heat sinking capacities, the bronchial arteries may be protected from unintended damage due to the treatment.

Figure 3:
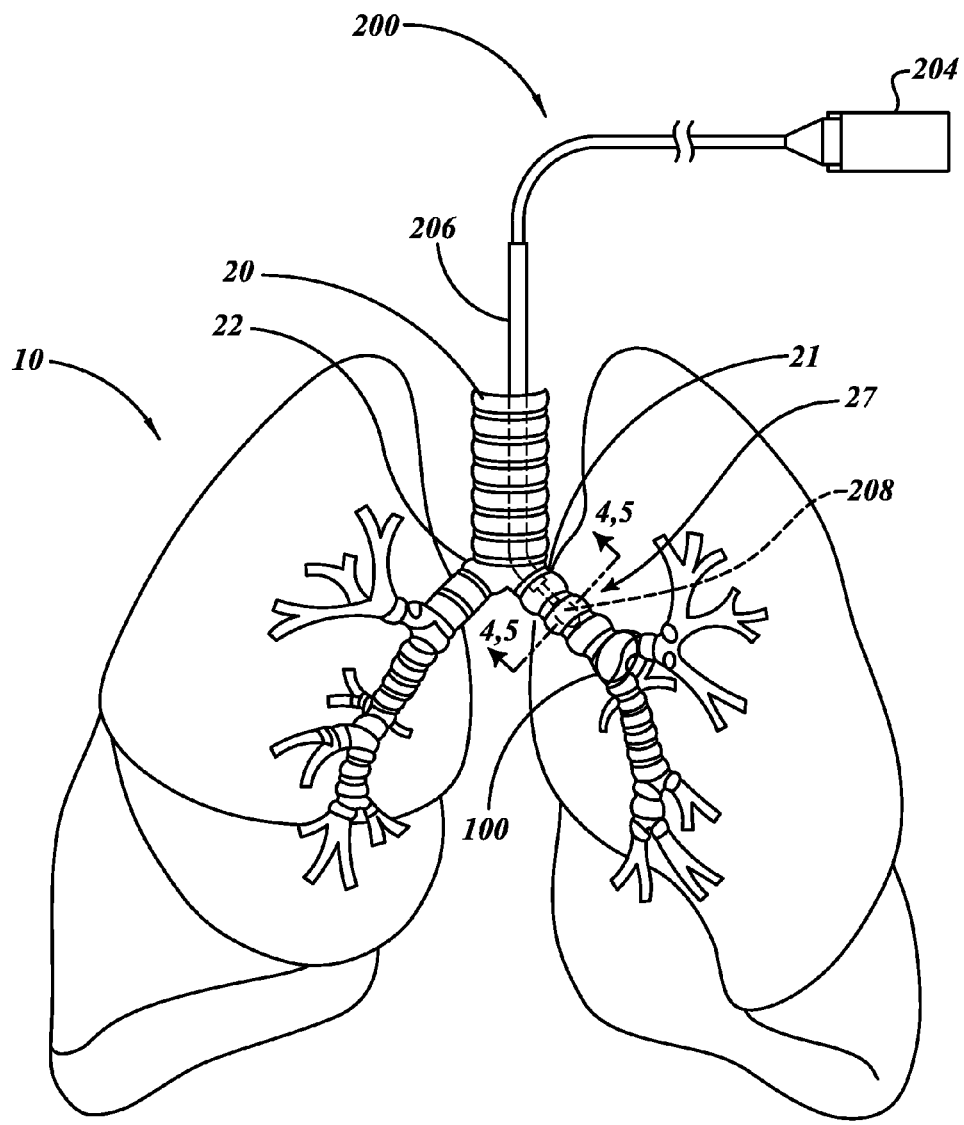
FIG. 3 is an illustration of a delivery device extending from a delivery apparatus positioned in the left main bronchus.

FIG. 3 shows a delivery device in the form of a catheter system 204 extending through a delivery apparatus 206. The catheter system 204 can treat airways of the main bronchi 21, 22, as well as airways that are distal to the main bronchi 21, 22. An ablation assembly 208 can be positioned outside the lung which is within the right or left main bronchi, the lobar bronchii, and bronchus intermedius. The intermediate bronchus is the portion of the right main bronchus and the origin of the middle and lower lobar bronchii. The ablation assembly 208 can be positioned in higher generation airways (e.g., airway generations >2) to affect remote distal portions of the bronchial tree 27. The catheter system 204 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

Each segmental bronchus may be treated by delivering energy to a single treatment site along each segmental bronchus. For example, the catheter system 204 can deliver energy to each segmental bronchus of the right lung. In some procedures, ten applications of energy can treat most of or substantially all of the right lung. In some procedures, most or substantially all of both lungs are treated using less than thirty-six different applications of energy. Depending on the anatomical structure of the bronchial tree, segmental bronchi can often be denervated using one or two applications of energy.

Function of other tissue or anatomical features, such as the mucous glands, cilia, smooth muscle, body vessels (e.g., blood vessels), and the like can be maintained when nerve tissue is ablated. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, a portion of an airway of the bronchial tree 27 can be denervated to attenuate one or more nervous system signals transmitted by nerve tissue. Denervating can include damaging all of the nerve tissue of a section of a nerve trunk along an airway to stop substantially all the signals from traveling through the damaged section of the nerve trunk to more distal locations along the bronchial tree or from the bronchial tree more proximally to the central nervous system. Additionally, signals that travel along nerve fibers that go directly from sensory receptors (e.g., cough and irritant receptors) in the airway to nearby effector cells (e.g., postganglionic nerve cells, smooth muscle cells, mucous cells, inflammatory cells, and vascular cells) will also be stopped. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation, mucous cells decrease mucous production, or inflammatory cells stop producing airway wall swelling and edema. These changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In some embodiments, one of the left and right main bronchi 21, 22 is treated to treat one side of the bronchial tree 27. The other main bronchus 21, 22 can be treated based on the effectiveness of the first treatment. For example, the left main bronchus 21 can be treated to treat the left lung 11. The right main bronchus 22 can be treated to treat the right lung 12. In some embodiments, a single treatment system can damage the nerve tissue of one of the bronchi 21, 22 and can damage the nerve tissue of the other main bronchus 21, 22 without removing the treatment system from the trachea 20. Nerve tissue positioned along the main bronchi 21, 22 can thus be damaged without removing the treatment system from the trachea 20. In some embodiments, a single procedure can be performed to conveniently treat substantially all, or at least a significant portion (e.g., at least 50%, 70%, 80%, 90% of the bronchial airways), of the patient's bronchial tree. In other procedures, the treatment system can be removed from the patient after treating one of the lungs 11, 12. If needed, the other lung 11, 12 can be treated in a subsequent procedure.

Figure 4:
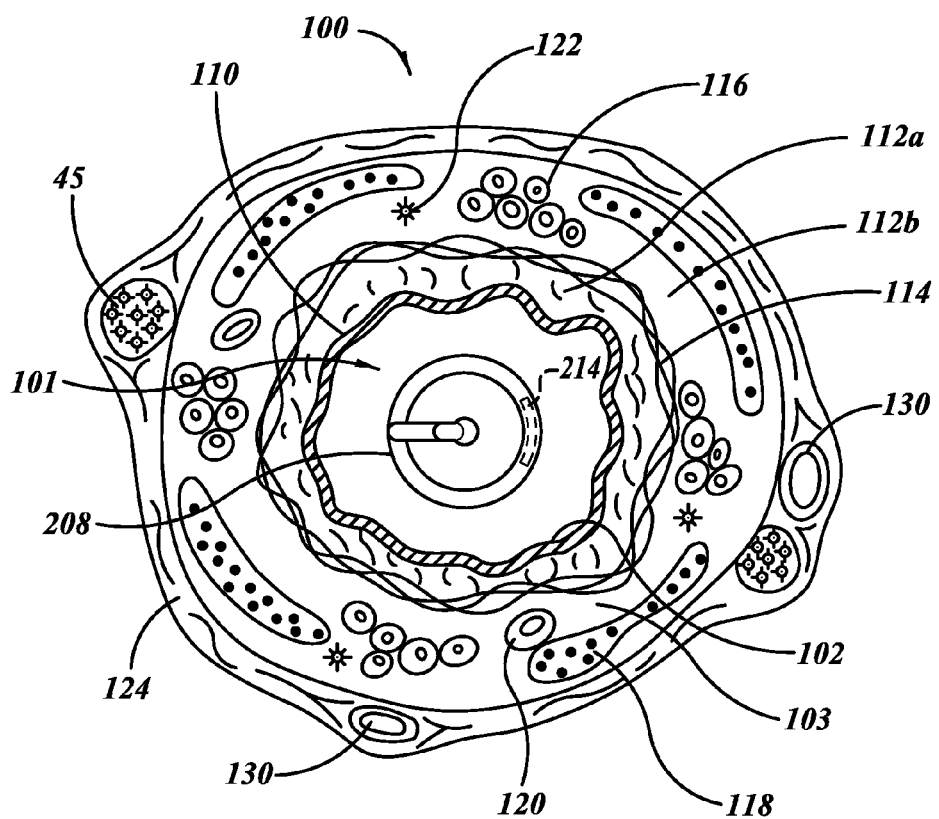
FIG. 4 is a cross-sectional view of an airway of a bronchial tree and a partially expanded ablation assembly positioned along an airway lumen.

FIG. 4 is a transverse cross-sectional view of a healthy airway 100, illustrated as a bronchial tube. The ablation assembly 208 is in a partially expanded state and positioned along the lumen 101 defined by an inner surface 102 of the airway 100. The illustrated inner surface 102 is defined by a folded layer of epithelium 110 surrounded by stroma 112a. A layer of smooth muscle tissue 114 surrounds the stroma 112a. A layer of stroma 112b is between the muscle tissue 114 and connective tissue 124. Mucous glands 116, cartilage plates 118, blood vessels 120, and nerve fibers 122 are within the stroma layer 112b. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Cilia can be damaged, excited, or otherwise altered to elicit a desired response along the epithelium 110 in order to control (e.g., increase or decrease) mucociliary transport. Many particles are inhaled as a person breathes, and the airways function as a filter to remove the particles from the air. The mucociliary transport system functions as a self-cleaning mechanism for all the airways throughout the lungs 10. The mucociliary transport is a primary method for mucus clearance from distal portions of the lungs 10, thereby serving as a primary immune barrier for the lungs 10. For example, the inner surface 102 of FIG. 4 can be covered with cilia and coated with mucus. As part of the mucociliary transport system, the mucus entraps many inhaled particles (e.g., unwanted contaminates such as tobacco smoke) and moves these particles towards the larynx. The ciliary beat of cilia moves a continuous carpet of mucus and entrapped particles from the distal portions of the lungs 10 past the larynx and to the pharynx for expulsion from the respiratory system. The ablation assembly 208 can damage the cilia to decrease mucociliary transport or excite the cilia to increase mucociliary transport.

The ablation assembly 208 can selectively treat target regions inside of the airway wall 103 (e.g., anatomical features in the stromas 112a, 112b). For example, the mucous glands 116 can be damaged to reduce mucus production a sufficient amount to prevent the accumulation of mucus that causes increased air flow resistance while preserving enough mucus production to maintain effective mucociliary transport, if needed or desired. Nerve branches/fibers passing through the airway wall 103 or other anatomical features in the airway wall 103 can also be destroyed.

If an ablation element is an RF electrode 214, the electrode 214 can be brought into contact with or proximate to the inner surface 102. The RF electrode 214 can output RF energy which travels through the tissue and is converted into heat. The heat causes formation of a lesion. The RF energy can be directed radially outward towards the nerve truck 45 and between the cartilage plates 118. The nerve trunk 45 can be damaged without causing appreciable damage to the adjacent cartilage plates 118. Damage to other non-targeted regions (e.g., the epithelium) can also be kept at or below an acceptable level.

Natural body functions can help prevent, reduce, or limit damage to tissue. Blood within the blood vessels 130 can absorb thermal energy and can then carry the thermal energy away from the heated section of the branches 130. In this manner, blood can mitigate or avoid damage to the blood vessels 130. After the treatment is performed, the bronchial artery branches 130 can continue to maintain the health of lung tissue. In some embodiments, a sufficient amount of RF energy is delivered to the nerve trunk 45 to destroy an entire longitudinal section of the nerve trunk 45 while keeping the amount of energy that reaches the blood vessels 130 below an amount that causes tissue destruction of the vessel 130. Thus, therapies can be performed without damaging to any significant extent other regions of the airway 100, even regions that are adjacent to the treatment site.

Treatment efficacy can be evaluated based at least in part on one or more airway attributes, pulmonary function tests, exercise capacity tests, and/or questionnaires. Patients can be evaluated to track and monitor their progress. If needed or desired, additional procedures can be performed until desired responses are achieved. Different types of instruments for evaluating airway attributes may be used. During ablation, feedback from an instrument can indicate whether the targeted tissue has been ablated. Once targeted tissue is ablated, therapy can be discontinued to minimize or limit collateral damage, if any, to healthy untargeted tissue.

Different attributes of airways can be evaluated to determine procedures to be performed. Such airway attributes include, without limitation, physical properties of airways (e.g., airway compliance, contractile properties, etc.), airway resistance, dimensions of airway lumens (e.g., shapes of airways, diameters of airways, etc.), responsiveness of airways (e.g., responsiveness to stimulation), muscle characteristics (e.g., muscle tone, muscle tension, etc.), inflammatory cells, inflammatory cytokines, or the like. In some embodiments, changes of airway muscle characteristics can be monitored by measuring pressure changes in the ablation assembly 208, which is inflated to a known pressure. Based on pressure changes, a physician determines the effects, if any, of the treatment, including, without limitation, whether targeted tissue has been stimulated, ablated, or the like.

Figure 5:
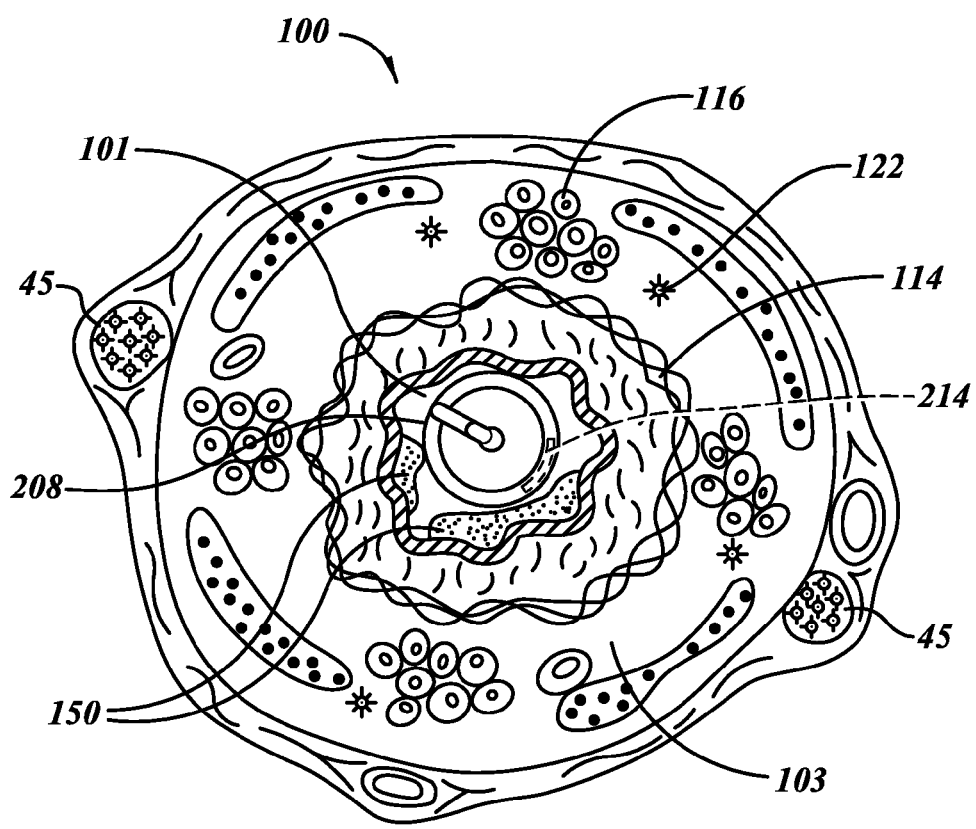
FIG. 5 is a cross-sectional view of an airway surrounding the partially expanded ablation assembly when smooth muscle of the airway is constricted and mucus is in an airway lumen.

FIG. 5 is a transverse cross-sectional view of a portion of the airway 100 that has smooth muscle tissue 114 in a contracted state, mucus 150 from hypertrophied mucous glands 116, and inflammatory swelling and edema fluid thickening the airway wall 103. The contracted muscle tissue 114, the mucus 150, and thickened airway wall 103 cooperate to partially obstruct the lumen 101 resulting in a relatively high air flow resistance. The nerve tissue 45 is damaged to relax the muscle tissue 114 to dilate the airway 100 to reduce air flow resistance, thereby allowing more air to reach the alveolar sacs for the gas exchange process. Decreases in airway resistance may indicate that passageways of airways are opening, for example in response to attenuation of nervous system input to those airways. The decrease of airway resistance associated with treating low generation airways (e.g., main bronchi, lobar bronchi, segmental bronchi) may be greater than the amount of decrease of airway resistance associated with treating high generation airways (e.g., subsegmental bronchioles). A physician can select appropriate airways for treatment to achieve a desired decrease in airway resistance and can be measured at a patient's mouth, a bronchial branch that is proximate to the treatment site, a trachea, or any other suitable location. The airway resistance can be measured before performing the therapy, during the therapy, and/or after the therapy. In some embodiments, airway resistance is measured at a location within the bronchial tree by, for example, using a vented treatment system that allows for respiration from areas that are more distal to the treatment site.

Energy can be used to damage target regions. As used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), and combinations thereof, as well as other types of energy suitable for treating tissue. In some embodiments, the catheter system 204 delivers energy and one or more substances (e.g., radioactive seeds, radioactive materials, etc.), treatment agents, and the like. Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, or combinations thereof. For example, long acting or short acting nerve blocking drugs (e.g., anticholinergics) can be delivered to the nerve tissue to temporarily or permanently attenuate signal transmission. Substances can also be delivered directly to the nerves 122 or the nerve trunks 45, or both, to chemically damage the nerve tissue.

Figure 6:
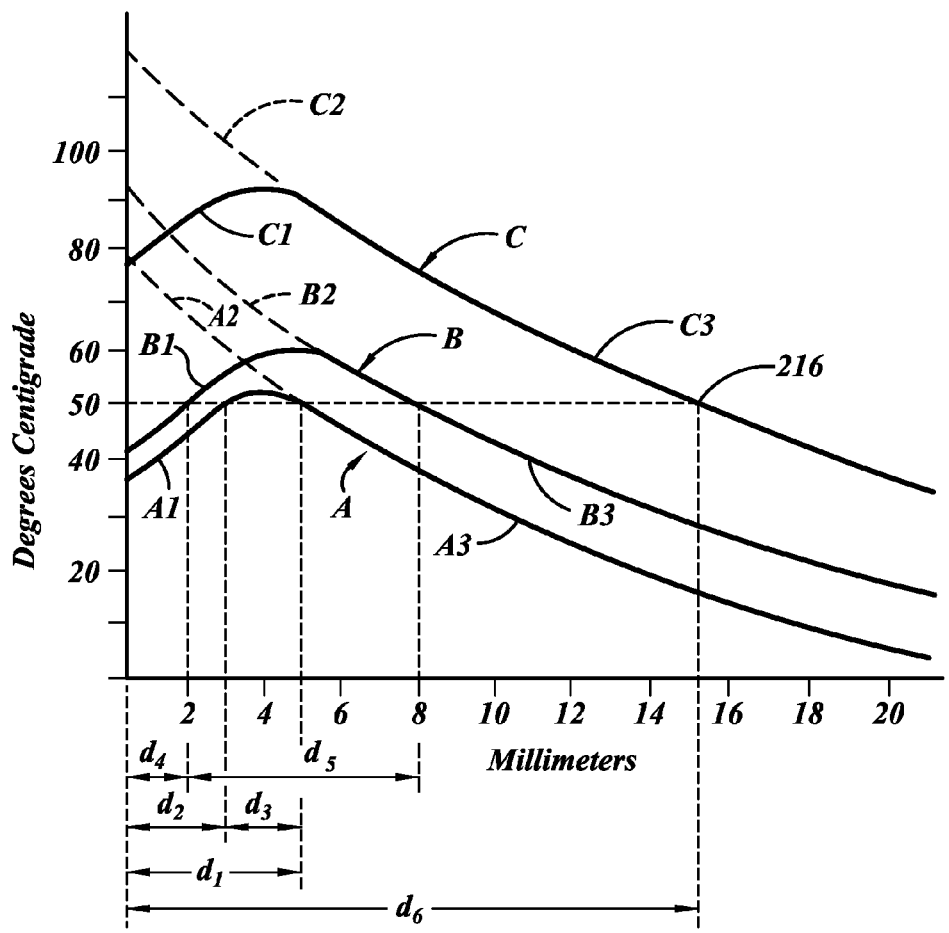
FIG. 6 is a graph of the depth of tissue versus the temperature of the tissue.
Figure 7:
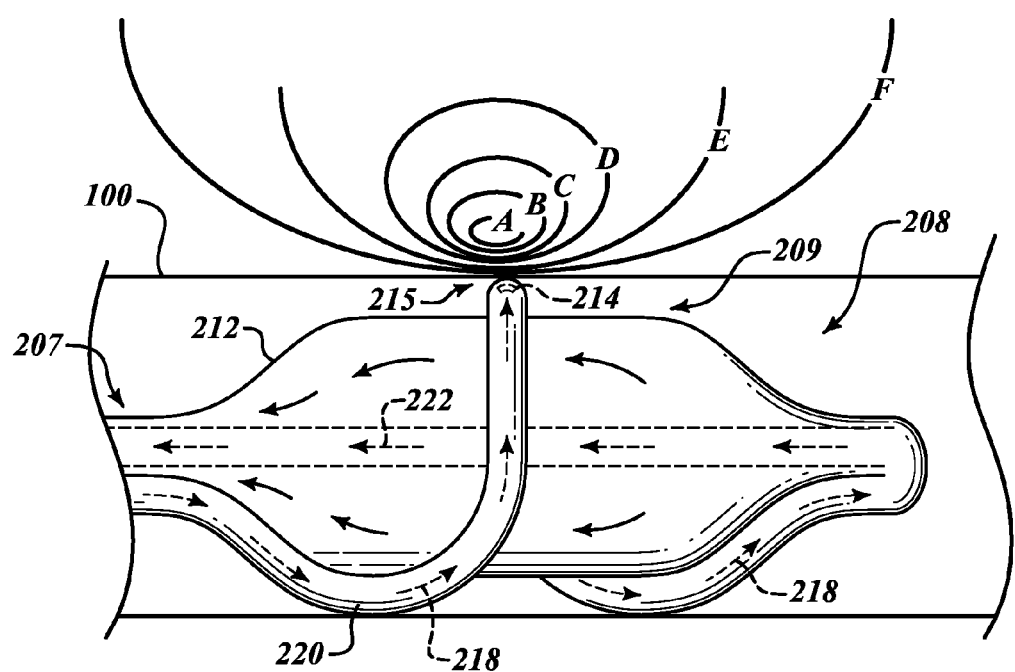
FIG. 7 is a side elevational view of an ablation assembly in an airway.

FIGS. 6 and 7 show the effect produced by superficial and deep heating by RF energy and superficial cooling by circulating coolant in the ablation assembly 208. A cooling section 209 of the ablation assembly 208 contains coolant to cool tissue adjacent to a tissue-contacting portion 215 of the energy emitter assembly 220 when energy is outputted. The cooling section 209 can absorb a sufficient amount of thermal energy from the airway wall 100 to limit or prevent damage to the tissue between the energy emitter assembly 220 and the nerve tissue or other targeted tissue.

FIG. 7 shows a cross-sectional temperature profile in a section of the airway wall through which the RF energy is delivered to ablate tissue. The terms "ablate" or "ablation," including derivatives thereof, include, without limitation, substantial altering of electrical properties, mechanical properties, chemical properties, or other properties of tissue. As used herein, the term "ablate," including variations thereof, refers, without limitation, to destroying or to permanently damaging, injuring, or traumatizing tissue. For example, ablation may include localized tissue destruction, cell lysis, cell size reduction, necrosis, or combinations thereof. In the context of pulmonary ablation applications, the term "ablation" includes sufficiently altering nerve tissue properties to substantially block transmission of electrical signals through the ablated nerve tissue.

FIG. 6 is a graph with a horizontal axis corresponding to the depth into the tissue of the airway wall from the point of contact with or proximate to the electrode 214 in millimeters with a vertical axis corresponding to the temperature of the tissue in degrees Centigrade. Temperatures in the figures are in degrees Centigrade, unless indicated otherwise. The point "0" on the graph corresponds to the point or area of contact between the electrode 214 and the tissue of the airway wall. Three curves A, B, and C are shown in the graph and correspond to three different power levels of radio frequency energy being delivered into the tissue. The temperature on the graph is up to about 100° C. The temperature of about 100° C., or slightly less, has been shown because it is considered to be an upper limit for tissue temperature during RF ablation. At approximately 90° C., tissue fluids begin to boil and tissue coagulates and chars, thereby greatly increasing its impedance and compromising its ability to transfer RF energy into the tissue of the airway wall. Thus, it may be desirable to have tissue temperatures remain below about 90° C. At about 50° C., a line 216 represents the temperature above which tissue cell death occurs and below which tissues suffer no substantial long term effects (or any long term effects).

Curve A shown in FIG. 6 represents what occurs with and without cooling of the electrode 214 at a relatively low power level, for example, about 10 watts of RF energy. Curve A is divided into three segments A1, A2, and A3. The broken line segment A2 represents a continuation of the exponential curve A3 when no cooling applied. As can be seen by curve A, the temperature of the electrode-tissue interface without cooling reaches 80° C. and decreases exponentially as the distance into the tissue of the airway 100 increases. As shown, the curve A3 crosses the 50° C. tissue cell death boundary represented by the line 216 at a depth of about 5 millimeters. Thus, without electrode cooling, the depth of cell death that would occur would be approximately 5 millimeters as represented by the distance d1. Further cell death would stop at this power level.

If active cooling is employed, the temperature drops to a much lower level, for example, about 35° C. as represented by the curve A1 at the electrode-tissue interface at 0 millimeters in distance. Since this temperature is below 50° C., cell death will not begin to occur until a distance of d2 at the point where the curve A2 crosses the cell death line at 50° C., for example, a depth of 3 millimeters from the surface. Cell death will occur at depths from 3 millimeters to 5 millimeters as represented by the distance d3. Such a cooled ablation procedure is advantageous because it permits cell death and tissue destruction to occur at a distance (or a range of distances) from the electrode-tissue interface without destroying the epithelium and the tissue immediately underlying the same. In some embodiments, the nerve tissues running along the outside of the airway can be ablated without damaging the epithelium or underlying structures, such as the stroma and smooth muscle cells.

The curve B represents what occurs with and without cooling of the electrode at a higher power level, for example, 20 watts of RF energy. Segment B2 of curve B represents a continuation of the exponential curve of the segment B3 without cooling. As can be seen, the temperature at the electrode-tissue interface approaches 100° C. which may be undesirable because that is a temperature at which boiling of tissue fluid and coagulation and charring of tissue at the tissue-electrode interface will occur, thus making significantly increasing the tissue impedance and compromising the ability to deliver additional RF energy into the airway wall. By providing active cooling, the curve B1 shows that the temperature at the electrode-tissue interface drops to approximately 40° C. and that cell death occurs at depths of two millimeters as represented by d4 to a depth of approximately 8 millimeters where the curve B3 crosses the 50° C. tissue cell death boundary. Thus, it can be seen that it is possible to provide a much deeper and larger region of cell death using the higher power level without reaching an undesirable high temperature (e.g., a temperature that would result in coagulation and charring of tissue at the electrode-tissue interface). The systems can be used to achieve cell death below the epithelial surface of the airway so that the surface need not be destroyed, thus facilitating early recovery by the patient from a treatment.

The curve C represents a still higher power level, for example, 40 watts of RF energy. The curve C includes segments C1, C2, and C3. The broken line segment C2 is a continuation of the exponential curve C3. Segment C2 shows that the temperature at the electrode-tissue interface far exceeds 100° C. and would be unsuitable without active cooling. With active cooling, the temperature at the electrode-tissue interface approaches 80° C. and gradually increases and approaches 95° C. and then drops off exponentially to cross the 50° C. cell death line 216 at a distance of about 15 millimeters from the electrode-tissue interface at the epithelial surface of the airway represented by the distance d6. Because the starting temperature is above the 50° C. cell death line 216, tissue cell death will occur from the epithelial surface to a depth of about 15 millimeters to provide large and deep regions of tissue destruction.

In FIG. 7, arrows 218 represent movement of the coolant through the energy emitter assembly 220. Arrows 222 represent movement of the coolant through a deployable element, illustrated as a distensible and thermally conductive balloon 212. Isothermal curves show the temperatures that are reached at the electrode 214 and at different depths into the airway wall 100 from the electrode-tissue interface when power is applied to the electrode 214 and coolant (e.g., a room temperature saline solution or iced saline) is delivered to the balloon 212. The term "element" in the context of "expandable element" includes a discrete element or a plurality of discrete elements. By way of example, an expandable element can be a single balloon or a plurality of balloons in fluid communication with one another.

By adjusting the rate of power delivery to the electrode 214, the rate at which coolant (e.g., saline solution) is passed into the balloon 212, the temperature of the saline solution, and the size of the balloon 212, and the exact contour and temperature of the individual isotherms can be modified. For example, by selecting the proper temperature and flow rate of saline and the rate of power delivery to the electrode, it is possible to achieve temperatures in which isotherm A=60° C., B=55° C., C=50° C., D=45° C., E=40° C., and F=37° C. Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. In some procedures, tissue at a depth of about 2 mm to about 8 mm in the airway wall can be ablated while other non-targeted tissues at a depth less than 2 mm in the airway wall are kept at a temperature below at temperature that would cause cell death. The coolant 218 can absorb energy to cool the tissue-contacting portion 215 of the energy emitter assembly 220 while the balloon 212 holds the energy emitter assembly 220 against the airway 100.

Figure 8:
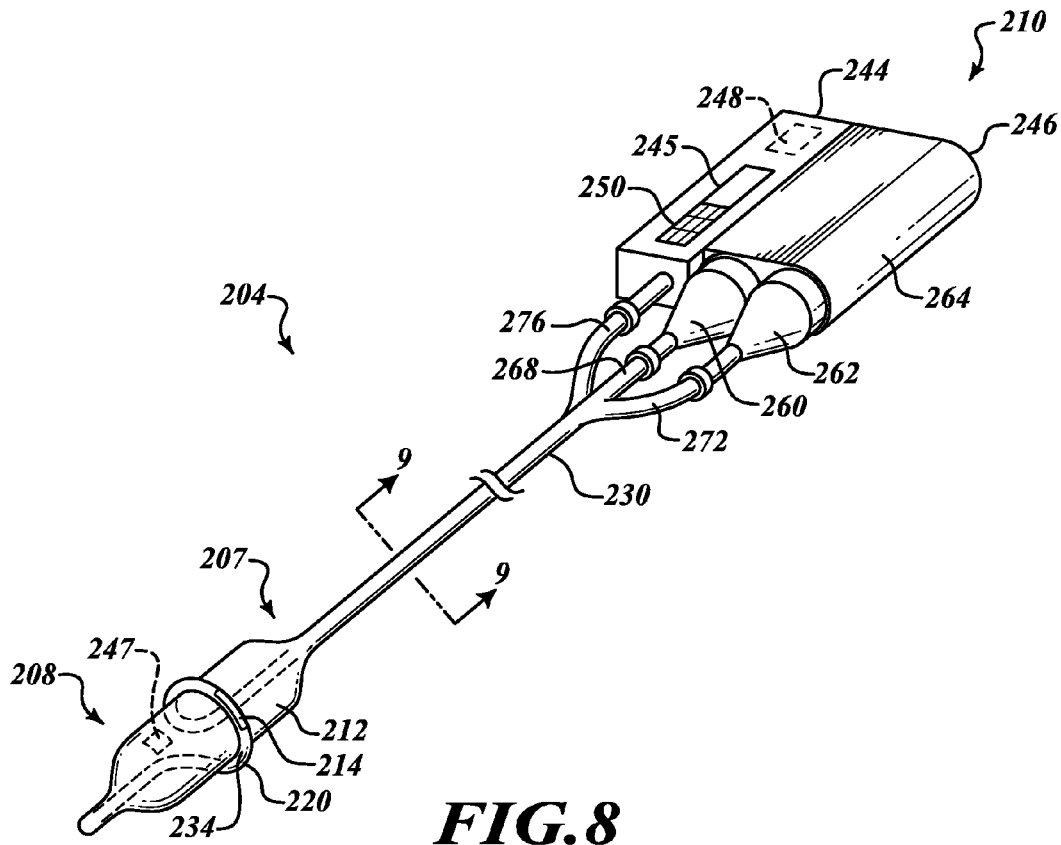
FIG. 8 is an isometric view of a delivery device according to one embodiment.

Referring to FIG. 8, the catheter system 204 includes a control module 210 coupled to a catheter 207 having an elongate body in the form of a shaft 230 and the ablation assembly 208 coupled to the distal end of the shaft 230. Ablation assembly 208 comprises an energy emitter assembly 220 extending from the elongate shaft 230 and wrapping around the balloon 212. The balloon 212 can be inflated from a collapsed state to the illustrated expanded state. As the balloon 212 inflates, the electrode 214 can be moved towards the airway wall. The inflated balloon 212 can help hold the electrode 214 near (e.g., proximate or in contact with) tissue through which energy is delivered. The coolant can absorb thermal energy to cool the balloon 212 or the energy emitter assembly 220, or both. This in turn cools the outer surface of the airway wall.

The control module 210 generally includes a controller 244 and a fluid delivery system 246. The controller 244 includes, without limitation, one or more processors, microprocessors, digital signal processors (DSPs), field programmable gate arrays (FPGA), and/or application-specific integrated circuits (ASICs), memory devices, buses, power sources, and the like. For example, the controller 244 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 244 may also include a display 245, such as a screen, and an input device 250. The input device 250 can include a keyboard, touchpad, or the like and can be operated by a user to control the catheter 207.

The controller 244 can store different programs. A user can select a program that accounts for the characteristics of the tissue and desired target region. For example, an air-filled lung can have relatively high impedance, lymph nodes have medium impedance, and blood vessels have relatively low impedance. The controller 244 can determine an appropriate program based on the impedance. A differential cooling program can be executed to deliver different temperature coolants through the balloon 212 and the energy emitter assembly 220. The temperature difference can be at least 10° C. Performance can be optimized based on feedback from sensors that detect temperatures, tissue impedance, or the like. For example, the controller 244 can control operation of the ablation assembly 208 based on a surface temperature of the tissue to which energy is delivered. If the surface temperature becomes excessively hot, cooling can be increased and/or electrode power decreased in order to produce deep lesions while protecting surface tissues.

An internal power supply 248 (illustrated in dashed line in FIG. 8) can supply energy to the electrode 214 and can be an energy generator, such as a radiofrequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 120 seconds. In some embodiments, the RF generator 248 has a single channel and delivers approximately 1 to 25 watts of RF energy and possesses continuous flow capability. Other ranges of frequencies, time intervals, and power outputs can also be used. Alternatively, the internal power supply 248 can be an energy storage device, such as one or more batteries. Electrical energy can be delivered to the energy emitter assembly 220, which converts the electrical energy to RF energy or another suitable form of energy. Other forms of energy that may be delivered include microwave, ultrasound, direct current, or laser energy. Alternatively, cryogenic ablation may be utilized wherein a fluid at cryogenic temperatures is delivered through the shaft 230 to cool a cryogenic heat exchanger on the ablation assembly 208.

The fluid delivery system 246 includes a fluid source 260 coupled to a supply line 268 and a fluid receptacle 262 coupled to a return line 272. The fluid source 260 can include a container (e.g., a bottle, a canister, a tank, or other type of vessel for holding fluid) held in a housing unit 264. In pressurizable embodiments, the fluid source 260 includes one or more pressurization devices (e.g., one or more pumps, compressors, or the like) that pressurize coolant. Temperature control devices (e.g., Peltier devices, heat exchangers, or the like) can cool or recondition the fluid. The fluid can be a coolant comprising saline, de-ionized water, refrigerant, cryogenic fluid, gas, or the like. In other embodiments, the fluid source 260 can be an insulated container that holds and delivers a chilled coolant to the supply line 268. The coolant flows distally through the elongate shaft 230 into the ablation assembly 208. Coolant in the ablation assembly 208 flows proximally through the elongate shaft 230 to the return line 272. The coolant proceeds along the return line 272 and ultimately flows into the fluid receptacle 262.

The balloon 212 optionally has a sensor 247 (illustrated in dashed line) that is communicatively coupled to the controller 244. The controller 244 can command the catheter 207 based on signals from the sensor 247 (e.g., a pressure sensor, a temperature sensor, a thermocouple, a pressure sensor, a contact sensor, or the like). Sensors can also be positioned on energy emitter assembly 220, along the elongate shaft 230 or at any other location. The controller 244 can be a closed loop system or an open loop system. For example, in a closed loop system, the electrical energy is delivered to the electrode 214 based upon feedback signals from one or more sensors configured to transmit (or send) one or more signals indicative of one or more tissue characteristics, energy distribution, tissue temperatures, or any other measurable parameters of interest. Based on those readings, the controller 244 adjusts operation of the electrode 214. Alternatively, in an open loop system, the operation of the electrode 214 is set by user input. For example, the user can observe tissue temperature or impedance readings and manually adjust the power level delivered to the electrode 214. Alternatively, the power can be set to a fixed power mode. In yet other embodiments, a user can repeatedly switch between a closed loop system and an open loop system.

To effectively cool the electrode 214, a conduit 234 coupled to the electrode 214 is fluidly coupled to a coolant delivery lumen within the shaft 230 to receive coolant therefrom. Alternatively, flow diverters within the balloon 212 can direct some or all of the coolant in the balloon 212 towards the electrode 214 or a balloon sidewall and may provide a separate cooling channel for the electrode 214. In some embodiments, one or more cooling channels extend through the electrode 214 (e.g., electrode 214 may be tubular so that coolant can flow through it). In other embodiments, the coolant flows around or adjacent the electrode 214. For example, an outer member, illustrated as a conduit 234 in FIG. 8, can surround the electrode 214 such that fluid can flow between the electrode 214 and the conduit 234. Additionally or alternatively, the ablation assembly 208 can be actively cooled or heated using one or more thermal devices (e.g., Peltier devices), cooling/heating channels, or the like.

Figure 9:
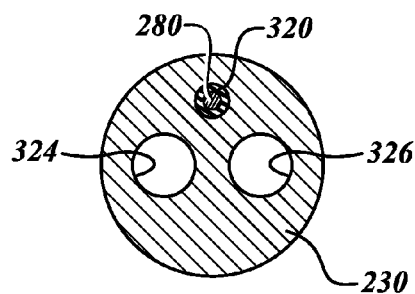
FIG. 9 is a cross-sectional view of an elongate body taken along a line 9-9 of FIG. 8.

Referring to FIGS. 8 and 9, the elongate shaft 230 extends from the control module 210 to the ablation assembly 208 and includes a power line lumen 320, a delivery lumen 324, and a return lumen 326. A power line 280 extends through the power line lumen 320 and couples the controller 244 to the electrode 214. The delivery lumen 324 provides fluid communication between the fluid source 260 and the energy emitter assembly 220 and balloon 212. The return lumen 326 provides fluid communication between the balloon 212 and/or electrode 214 and the fluid receptacle 262. The elongate shaft 230 can be made, in whole or in part, of one or more metals, alloys (e.g., steel alloys such as stainless steel), plastics, polymers, and combinations thereof, as well as other biocompatible materials, and can be flexible to pass conveniently along highly branched airways. Sensors can be embedded in the elongate shaft 230 to detect the temperature of the fluids flowing therethrough.

Figure 10:
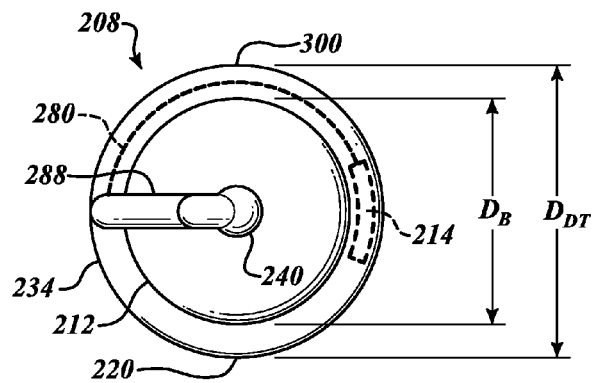
FIG. 10 is a front elevational view of the delivery device of FIG. 9.
Figure 11:
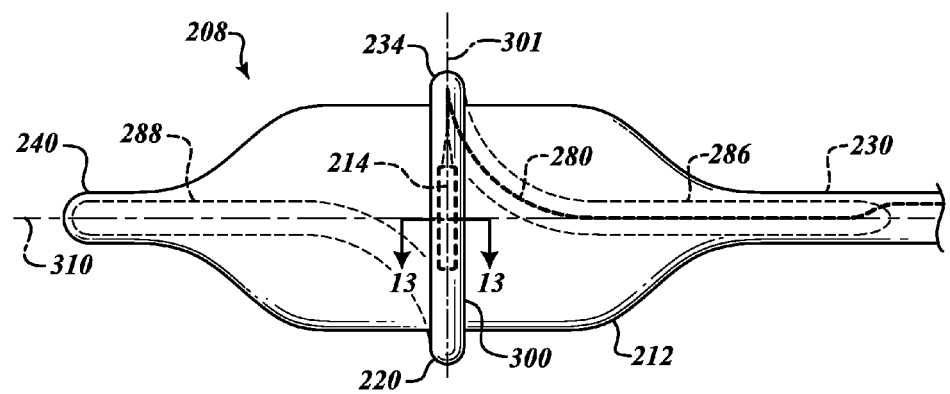
FIG. 11 is an elevational view of a left side of an ablation assembly.
Figure 12:
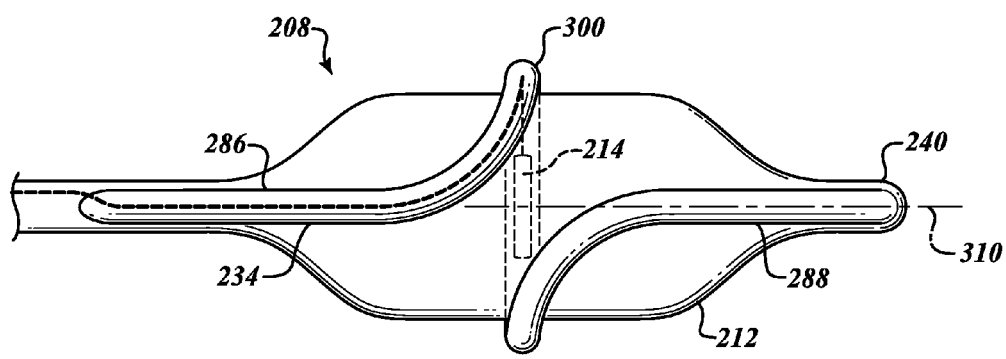
FIG. 12 is an elevational view of a right side of the ablation assembly of FIG. 11.

Referring to FIGS. 10-12 in which the ablation assembly 208 is in an expanded configuration, the conduit 234 surrounds and protects the electrode 214 and the power line 280 from the external environment and from external forces which could cause connection failure. The electrical connections are also not exposed to bodily fluids. The power line 380 can be routed along other fluid paths, if needed or desired. Alternatively, electrode 214 may be a metallic tubular member with conduit 234 being coupled to each of its ends in order to deliver coolant through the electrode 214. In this case, electrode 214 has an exposed external surface which is used to contact the airway wall during energy delivery.

The conduit 234 includes a proximal section 286, a distal section 288, and a non-linear section 300. The proximal section 286 functions as an inlet and extends distally from the elongate shaft 230. The non-linear section 300 extends circumferentially about the balloon 212 and has an arc length in a range of about 180 degrees to 450 degrees. As shown in FIG. 11, in the expanded configuration of ablation assembly 208, at least a portion of the non-linear section 300 can be positioned along an imaginary plane 301 that is approximately perpendicular to a longitudinal axis 310 of the inflated balloon 212 (and catheter shaft 230). The distal section 288 is aligned with the proximal section 286 and functions as an outlet and extends distally to the atraumatic tip 240.

When deflated (i.e., when not pressurized with coolant), the conduit 234 can be highly flexible to conform about the elongate shaft 230 and can be made, in whole or in part, of a material that assumes a preset shape when pressurized or activated. Such materials include, without limitation, thermoformed polymers (e.g., polyethylene terephthalate, polyethylene, or polyurethanes), shape memory materials, or combinations thereof. When the conduit 234 is inflated, it assumes a preset shape configured to position electrode 214 in the desired transverse orientation with respect to longitudinal axis 310.

The balloon 212 can be made, in whole or in part, of polymers, plastics, silicon, rubber, polyethylene, polyvinyl chloride, chemically inert materials, non-toxic materials, electrically insulating materials, combinations thereof, or the like. To enhance heat transfer, the balloon sidewall can comprise one or more conductive materials with a high thermal conductivity. For example, conductive strips (e.g., metal strips) can extend along the balloon 212 to help conduct thermal energy away from hot spots, if any. The balloon 212 can conform to irregularities on the airway surface (e.g., cartilaginous rings, side branches, etc.) and can be made, in whole or in part, of a distensible material, such as polyurethane (e.g., low durometer polyurethane) or other type of highly conformable material that may be transparent, semi-transparent, or opaque. The balloon 212 can have different inflated shapes, including a hot dog shape, an ovoid shape, a cylindrical shape, or the like.

Figure 13:
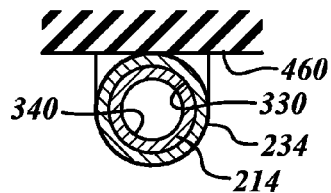
FIG. 13 is a cross-sectional view taken along a line 13-13 of FIG. 11.

FIG. 13 shows the electrode 214 positioned in a channel 330 of the conduit 234 and includes a coolant channel 340. The electrode main body 350 can be a rigid tube made, in whole or in part, of metal (e.g., titanium 304, stainless steel, or the like) or other suitable metal. In some embodiments, conduit 234 does not extend over the entire electrode 214, leaving a central portion of the tubular electrode exposed for direct contact with the airway wall. In other embodiments, the electrode main body 350 is made, in whole or in part, of a shape memory material. Shape memory materials include, for example, shape memory metals or alloys (e.g., Nitinol), shape memory polymers, ferromagnetic materials, combinations thereof, and the like. These materials can assume predefined shapes when released from a constrained condition or different configurations when activated with heat. In some embodiments, the shape memory material can be transformed from a first preset configuration to a second preset configuration when activated (e.g., thermally activated).

Figure 14:
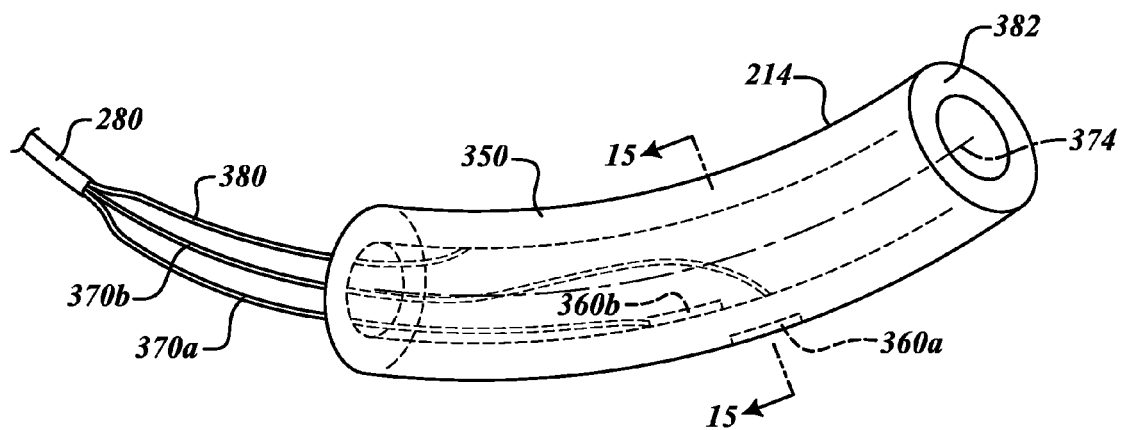
FIG. 14 is an isometric view of an electrode assembly.
Figure 15:
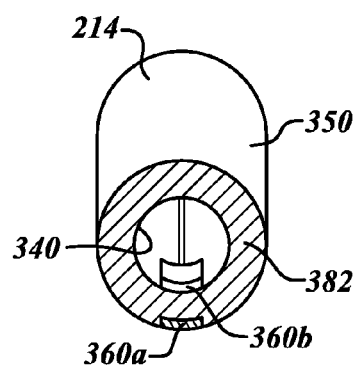
FIG. 15 is a cross-sectional view of the electrode assembly of FIG. 14 taken along a line 15-15.

As shown in FIGS. 14 and 15, sensors 360a, 360b (collectively "360") are coupled to the electrode main body 350. A pair of lines 370a, 370b (collectively "370") pass through the channel 340 and are coupled to the sensors 360a, 360b, respectively. In some embodiments, the sensor 360a is a contact sensor, and the sensor 360b is a temperature sensor and/or a pressure sensor. The number, positions, and types of sensors can be selected based on the treatment to be performed.

In multilayer embodiments, the electrode main body 350 can include at least one tube (e.g., a non-metal tube, a plastic tube, etc.) with one or more films or coatings. The films or coatings can be made of metal, conductive polymers, or other suitable materials formed by a deposition process (e.g., a metal deposition process), coating process, etc., and can comprise, in whole or in part, silver ink, silver epoxy, combinations thereof, or the like.

Radio-opaque markers or other types of visualization features can be used to position the main body 350. To increase visibility of the electrode 214 itself, the electrode 214 may be made, in whole or in part, of radiographically opaque material.

Figure 16:
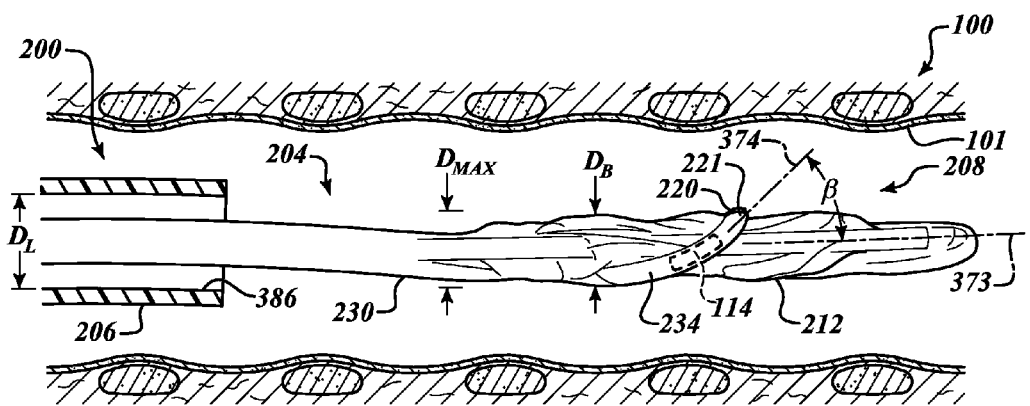
FIG. 16 is a partial cross-sectional view of a treatment system with a delivery device extending out of a delivery apparatus.
Figure 17:
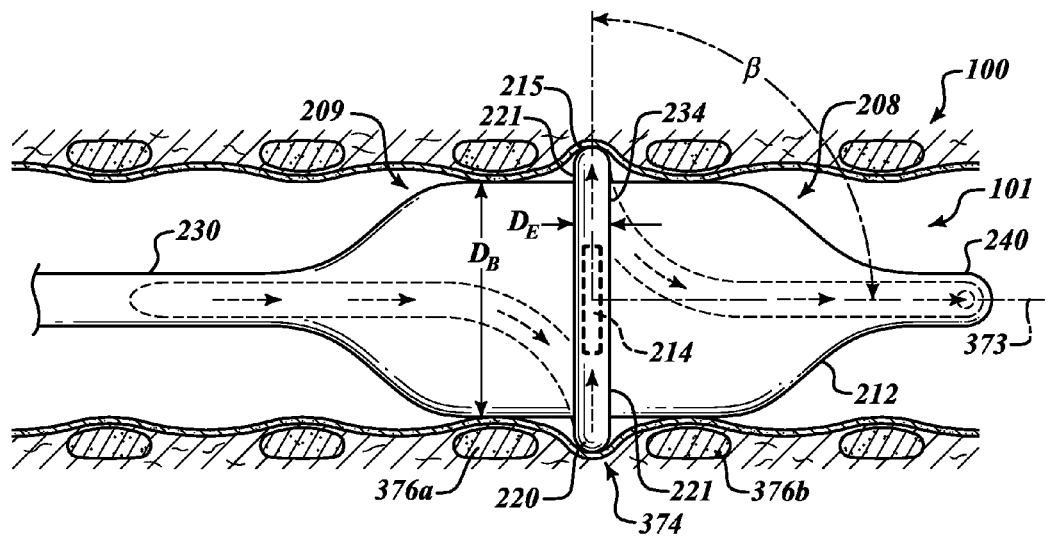
FIG. 17 is a side elevational view of a deployed ablation assembly with fluid flowing through an energy emitter assembly.
Figure 18:
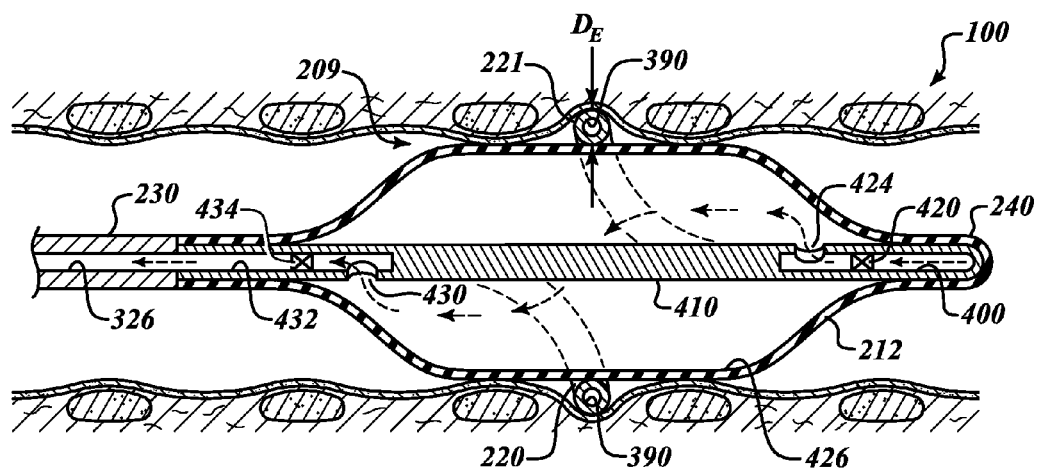
FIG. 18 is a cross-sectional view of the deployed ablation assembly with fluid flowing through an expandable member.

FIGS. 16-18 show one exemplary method of using the treatment system 200. A physician can visually inspect the airway 100 using the delivery apparatus 206 to locate and evaluate the treatment site(s) and non-targeted tissues before, during, and/or after performing a therapy. The delivery apparatus 206 can be a guide tube, a delivery sheath, a bronchoscope, or an endoscope and can include one or more viewing devices, such as optical viewing devices (e.g., cameras), optical trains (e.g., a set of lens), and the like. For example, the delivery apparatus 206 can be a bronchoscope having one or more lights for illumination and optical fibers for transmitting images. The catheter 207 may be adapted to be delivered over a guidewire (not shown) that passes between the balloon 212 and the energy emitter assembly 220. This provides for rapid exchange capabilities.

When the delivery apparatus 206 of FIG. 16 is moved along a body lumen 101 (e.g., airway), the collapsed ablation assembly 208 is held within a working channel 386 of the delivery apparatus 206. The conduit 234 can form a loop 221 such that the electrode 214 is almost parallel to a long axis 373 when the catheter 207 is in a substantially straight configuration. In the illustrated embodiment of FIG. 16, an angle $\beta$ is defined between the direction of the long axis 373 of the catheter 207 and a long axis 374 of the electrode 214. The angle $\beta$ can be in a range of about 0 degrees to about 30 degrees. In some embodiment, the angle $\beta$ is in a range of about 0 degrees to about 20 degrees. The electrode 214, being curved, can also nest with and partially encircle the elongate shaft 230. In certain embodiments, at least a portion of the elongate shaft 230 is disposed within an arc of the electrode 214 for a further reduced profile. As such, the shaft 230 can be positioned between the ends of the electrode 214. Electrode 214 may have various lengths, depending on the desired length of the lesion to be created in each electrode position. In preferred embodiments, electrode 214 has a length of at least about 2 mm up to about 3 mm. The electrode can have a width (or diameter if cylindrical) no larger than the width of the spaces between the cartilage rings, preferably in some embodiments being 0.1 to about 3 mm.

With continued reference to FIG. 16, the diameter $D_L$ of the working channel 386 can be less than about 8 mm. The diameter $D_B$ of the deflated balloon 212 can be relatively small. For example, a minimum diameter $D_{B\ min}$ can be in a range of about 2 mm to about 3 mm, and a maximum diameter $D_{B\ max}$ in a range of about 5 mm to about 6 mm when the balloon 212 is fully collapsed. If the electrode 214 is collapsible, the diameter $D_{max}$ of the ablation assembly 208 can be less than about 3 mm. In ultra low-profile configurations, the maximum diameter $D_{max}$ can be less than about 2.8 mm.

The balloon 212 can be inflated to move the energy emitter assembly 220 near (e.g., proximate to or in contact with) the airway 100. The angle $\beta$ can be increased between 70 degrees and about 110 degrees when the balloon 212 is fully inflated. FIG. 17 shows the ablation assembly 208 deployed, wherein the electrode 214 can be about perpendicular to the long axis 373. There can be play between the energy emitter assembly 220 and the balloon 212 such that the angle $\beta$ is in a range of about 60 degrees to about 120 degrees in order to accommodate variations of anatomical structures, mis-alignment (e.g., mis-alignment of the catheter shaft 230), or the like. In some embodiments, the electrode 214 moves towards a circumferentially extending orientation as it moves from a delivery orientation to the deployed orientation. The electrode 214 in the deployed orientation extends substantially circumferentially along the wall of the airway 100. In certain embodiments, the electrode 214 will be configured to be positioned entirely within the spaces 374 between cartilage rings 376 along the airway wall when the ablation assembly 208 is in the fully deployed configuration.

FIGS. 17 and 18 show the energy emitter assembly 220 fluidically coupled to both the elongate shaft 230 and the balloon 212. Generally, coolant cools the tissue-contacting portion 215 of the energy emitter assembly 220. The cooling section 209 of the ablation assembly 208 contacts the airway wall 100 so as to cool tissue adjacent to the tissue-contacting portion 215 while energy is outputted by the electrode 214. The cooling section 209 can be formed by the portions of the energy emitting assembly 220 and the balloon 212 that contact the airway wall 100.

As the balloon 212 inflates, the electrode 214 moves (e.g., pivots, rotates, displaces, etc.) from a first orientation of FIG. 16 in which the electrode 214 extends axially along the airway 100 and a second orientation of FIG. 17 in which the entire electrode 214 is disposed in a space 374 between adjacent cartilage rings 376a, 376b. The balloon 212 can both cool the airway 100 and cause the electrode 114 to seat in the space 374.

FIG. 17 shows the energy emitter assembly 220 positioned to locate the electrode 214 in the space 374. In certain embodiments, the electrode 214, in the first orientation, extends a distance with respect to a longitudinal axis 373 (see FIG. 16) can be greater than the distance the electrode 214, in the second orientation, extends with respect to the longitudinal axis 373.

To deploy the energy emitting assembly 208, coolant from the elongate shaft 230 flows through the energy emitter assembly 220 and into the balloon 212. The electrode 214 can output a sufficient amount of energy to ablate a target region. The coolant absorbs thermal energy from electrode 214 and the airway wall 100.

The diameter $D_E$ of the electrode 214 and conduit 234 can be in a range of about 1.5 mm to about 2.5 mm when pressurized with coolant. Such embodiments are well suited to treat tissue outside the lung along the main bronchi. In certain embodiments, the diameter $D_E$ is about 2 mm. In yet other embodiments, the diameter $D_E$ can be in a range of about 0.1 mm to about 3 mm. The diameter $D_E$ of the deflated conduit 234 and electrode 214 can be about 0.1 mm to about 1 mm.

To treat a bronchial tree of a human, the diameter of the inflated balloon 212 can be in a range of about 12 mm to about 18 mm. For enhanced treatment flexibility, the inflated balloon diameter may be in a range of about 7 mm to about 25 mm. Of course, the balloon 212 can be other sizes to treat other organs or tissue of other animals.

The ablation assembly 208 provides differential cooling because the coolant in the energy emitter assembly 220 is at a lower temperature and higher velocity than the coolant in the balloon 212. Coolant, represented by arrows, flows out of the elongate shaft 230 and into the energy emitter assembly 220. The coolant proceeds through the energy emitter assembly 220 and the coolant channel 340 (FIG. 15) of the electrode 214. The coolant absorbs thermal energy from the electrode 214. The heated coolant flows into the tip 240 and proceeds proximally through a lumen 400, as shown in FIG. 18. The coolant flows through a valve 420 (e.g., a throttle) and passes through a port 424. The valve 420 is disposed along a fluid path connecting the energy emitting assembly 220 and the portion of the balloon 212 defining the cooling section 209. The coolant circulates in a chamber 426 and absorbs heat from the tissue. This helps keep shallow tissue below a temperature that would cause cell death or tissue damage.

The coolant flows through a port 430, a lumen 432, and a throttle 434. The throttles 420, 434 can cooperate to maintain a desired pressure. The throttle 420 is configured to maintain a first flow rate of the coolant through the energy emitting assembly 220 and a second flow rate of the coolant through the cooling section 209. The first flow rate can be significantly different from the second flow rate.

The conduit 234 can assume a preset shape when pressurized. The valves 420, 434 can cooperate to maintain the desired pressure within the balloon 212 within a range of about 5 psig to about 15 psig. Such pressures are well suited to help push the electrode 214 between cartilaginous rings. Other pressures can be selected based on the treatment to be performed. The valves 420, 434 can be throttle valves, butterfly valves, check valves, duck bill valves, one-way valves, or other suitable valves.

When RF energy is transmitted to the electrode 214, the electrode 214 outputs RF energy that travels through tissue. The RF energy can heat tissue (e.g., superficial and deep tissue) of the airway wall while the coolant cools the tissue (e.g., superficial tissues). The net effect of this superficial and deep heating by RF energy and superficial cooling by the circulating coolant is the concentration of heat in the outer layers of the airway wall 100, as discussed in connection with FIGS. 6 and 7. The temperature of the connective tissue can be higher than the temperatures of the epithelium, stroma, and/or smooth muscle. By example, the temperature of the connective tissue can be sufficiently high to cause damage to the nerve trunk tissue or other deep tissue while other non-targeted tissues of the airway are kept at a lower temperature to prevent or limit damage to the non-targeted tissues.

Heat can be concentrated in one or more of the internal layers (e.g., the stroma) of the airway wall or in the inner lining (e.g., the epithelium) of the airway wall. Furthermore, one or more of the vessels of the bronchial artery branches may be within the lesion. The heat generated using the electrode 214 can be controlled such that blood flowing through the bronchial artery branches protects those branches from thermal injury while nerve trunk tissue is damaged, even if the nerve tissue is next to the artery branches. The catheter 207 can produce relatively small regions of cell death. For example, a 2 mm to 3 mm section of tissue in the middle of the airway wall 100 or along the outer surface of the airway wall 100 can be destroyed. By the appropriate application of power and the appropriate cooling, lesions can be created at any desired depth.

A circumferential lesion can be formed around all or most of the circumference of the airway wall 100 by ablating tissue while slowly rotating the ablation assembly 208 or by positioning the ablation assembly 208 in a series of rotational positions at each of which energy is delivered for a desired time period. Some procedures form adjacent lesions that become contiguous and form a circumferential band all the way around the airway wall 100. In some embodiments, the entire loop 221 (FIG. 17) can be an electrode. The loop 221 can be coated with a conductive material and can carry the electrode. A single procedure can produce a circumferential lesion. After forming the lesion, coolant flowing into the balloon 212 can be stopped. The balloon 212 is deflated causing the energy emitter assembly 220 to recoil away from the airway wall 100. The catheter 207 may be repositioned to treat other locations or removed from the subject entirely.

Figure 19:
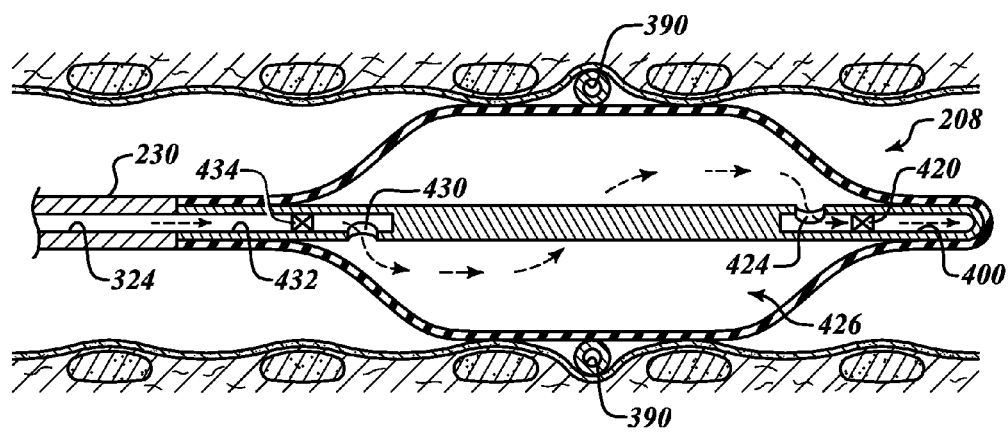
FIG. 19 is a cross-sectional view of the ablation assembly with fluid flowing into the expandable member.
Figure 20:
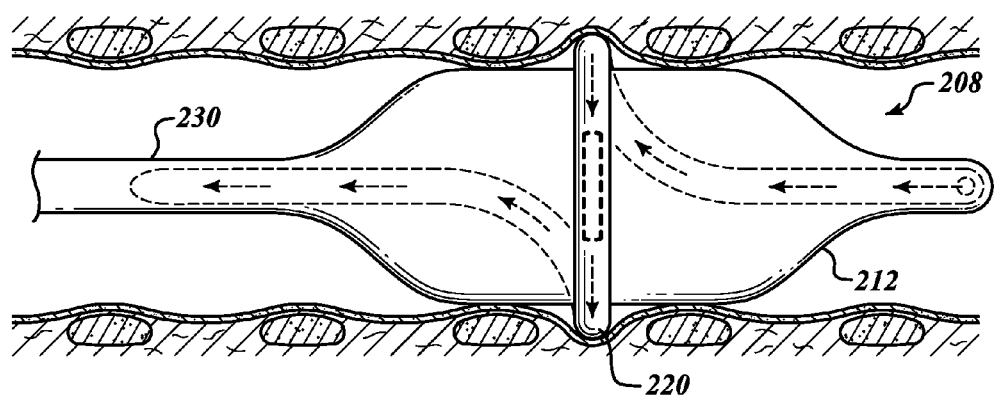
FIG. 20 is an elevational view of the ablation assembly with fluid flowing through the energy emitter assembly.

If the user wants the coolant in the balloon 212 to be at a lower temperature than the coolant in the energy emitter assembly 220, chilled coolant can be delivered into the balloon 212 and then into the energy emitter assembly 220. FIGS. 19 and 20 show such a coolant flow. Low temperature coolant flowing through the elongate body 230 passes through the valve 434 and the port 430. The coolant circulates in the chamber 426 and absorbs heat. The heated coolant flows through the valve 420 and proceeds through the energy emitter assembly 220 to cool the electrode 214.

Airway cartilage rings or cartilage layers typically have a significantly larger electrical resistance than airway soft tissue (e.g., smooth muscle or connective tissue). Airway cartilage impedes energy flow (e.g., electrical radiofrequency current flow) and makes the formation of therapeutic lesions with radiofrequency electrical energy to affect airway nerve trunk(s) challenging when the electrode is next to cartilage.

Figure 21:
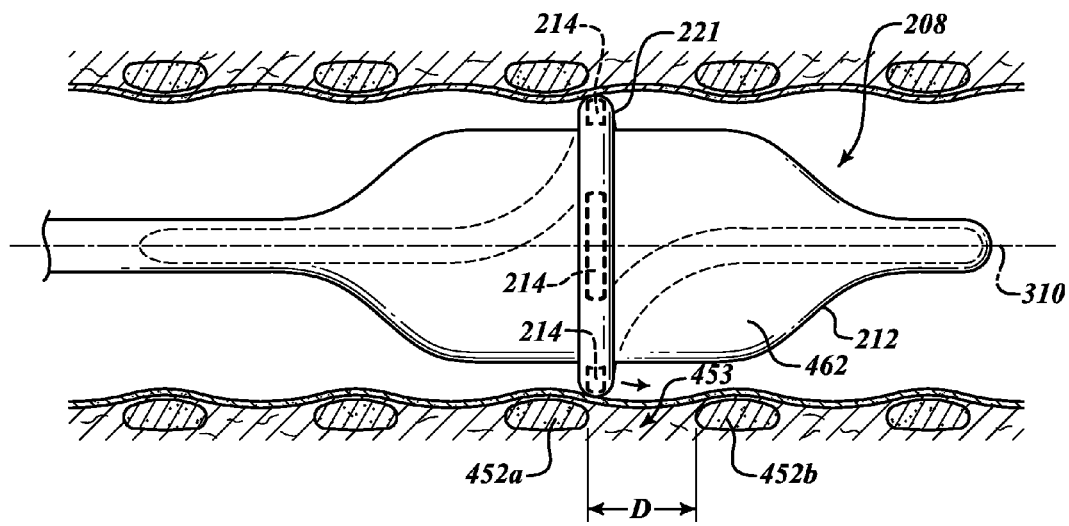
FIG. 21 is a side elevational view of an electrode adjacent a cartilaginous ring.
Figure 22:
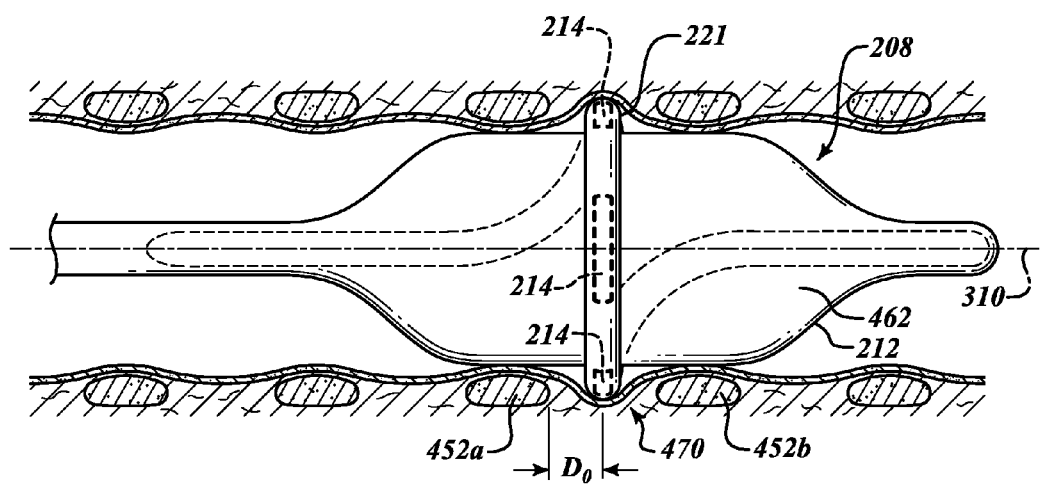
FIG. 22 is a side elevational view of electrodes positioned between cartilaginous rings.

Positioners can facilitate positioning of the electrodes. Such positioners can include, without limitation, bumps, bulges, protrusions, ribs or other features that help preferentially seat the electrode 214 at a desired location, thus making it easy to perform the treatment or to verify correct positioning. FIGS. 21 and 22 show the energy emitter assembly capable of serving as an intercartilaginous positioner. When the balloon 212 presses against the airway 100, the loop 221 moves along the balloon 212 to preferentially position the electrodes 214 between cartilage rings 452a, 452b. The loop 221 protrudes outwardly from the balloon 212 a sufficient distance to ensure that the ablation assembly 208 applies sufficient pressure to the airway wall to cause self-seating. The catheter can be moved back and forth to help position the electrodes 214 next to soft compliant tissue 453 in the space 453. The energy emitter assembly 220 can be configured to displace a distance $D_o$ (e.g., measured along a long axis 310), which is at least half of the distance D between the cartilage rings 452a, 452b. This ensures that the electrodes 214 can be positioned generally midway between the cartilage rings 452a, 452b.

The plurality of electrodes 214 can reduce both treatment time and procedure complexity as compared to a catheter with a single electrode. This is because the multi-electrode catheter may have to be positioned a smaller number of times within a bronchial tree (or other hollow organ) as compared to single electrode catheters to produce a number of lesions of a desired therapeutic size. Multi-electrode catheters can thus precisely and accurately treat a user's respiratory system.

Figure 23:
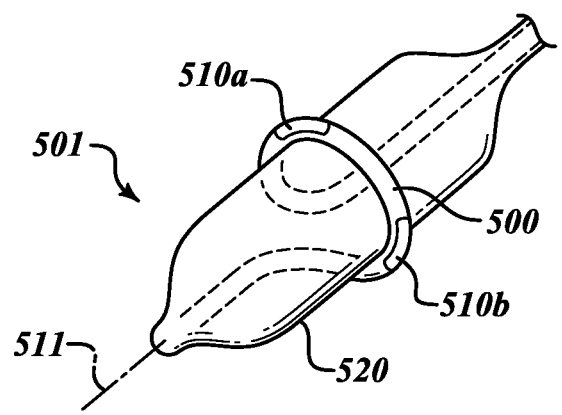
FIG. 23 is an isometric view of an ablation assembly with a pair of electrodes.
Figure 24:
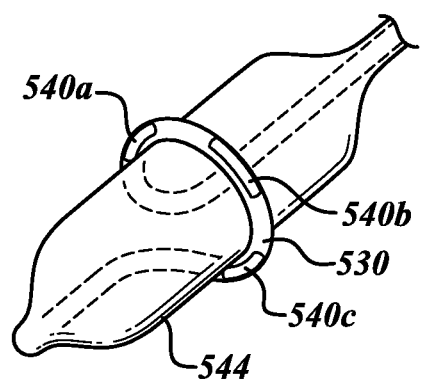
FIG. 24 is an isometric view of an ablation assembly with three electrodes.

FIG. 23 shows an energy emitter assembly 500 that includes two electrodes 510a, 510b (collectively "510") spaced apart from one another about a circumference of a balloon 520. The electrodes 510a, 510b can be about 45 degrees to 210 degrees from another with respect to a long axis 511 of an ablation assembly 501. Other electrode positions are possible. FIG. 24 shows an energy emitter assembly 530 with three electrodes 540a, 540b, 540c (collectively "540") positioned about 60 degrees from one another. In these embodiments, each electrode may be coupled to separate power lines to allow for independent control of each, or all electrodes may be coupled to the same power line so as to be operated together. Further, a pair of electrodes may be operated in a bipolar manner, wherein one electrode is positive and the other negative, with RF power being transmitted from one to the other through the tissue.

Figure 25:
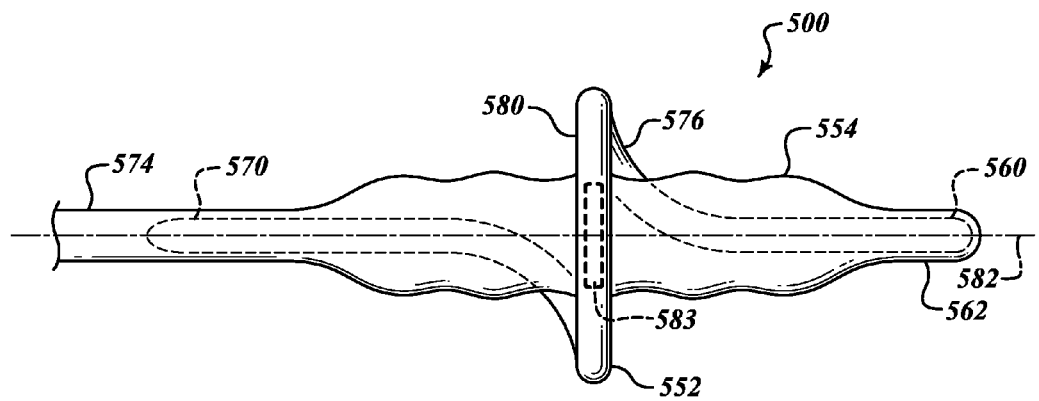
FIG. 25 is a side elevational view of an ablation assembly with a deployed energy emitter assembly and a collapsed expandable element.
Figure 26:
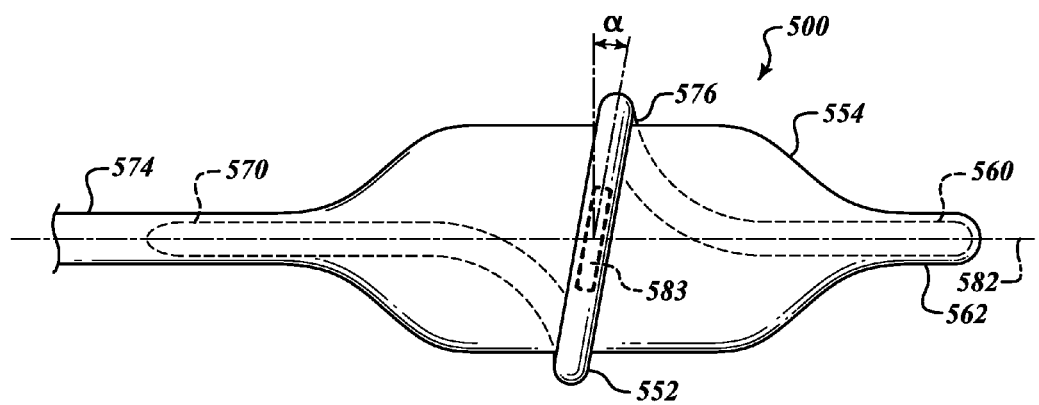
FIG. 26 is a side elevational view of the ablation assembly of FIG. 25 with the expandable element in an inflated state.

Referring to FIGS. 25 and 26, a distal end 560 of an energy emitter assembly 552 is coupled to a tip 562. A proximal end 570 of the energy emitter assembly 552 is coupled to an elongate body 574. A central section, illustrated as a curved section 576, is not directly connected to a balloon 554. This allows for a significant amount of movement of an electrode 583 and convenient alignment with gaps between cartilage or other features.

When the balloon 554 is partially inflated (shown in FIG. 25), an arcuate section 580 of the central section 576 can be generally perpendicular to a longitudinal axis 582 of the balloon 554. When the balloon 554 is fully expanded (shown in FIG. 26), there can be sufficient clearance to allow movement of the electrode 583 without significant deformation of the balloon 554. For example, the electrode 583 can be moved an angle α in a range of about −30 degrees to about 30 degrees. Other angles are also possible.

Figure 27:
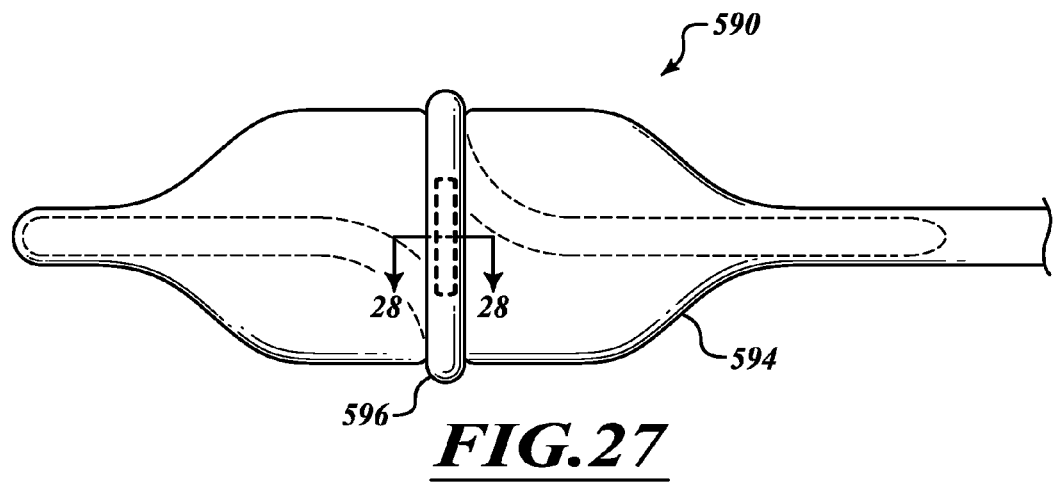
FIG. 27 is a side elevational view of an ablation assembly with a compliant expandable element.
Figure 28:
FIG. 28 is a cross-sectional view of the ablation assembly of FIG. 27 taken along a line 28-28.
Figure 29:
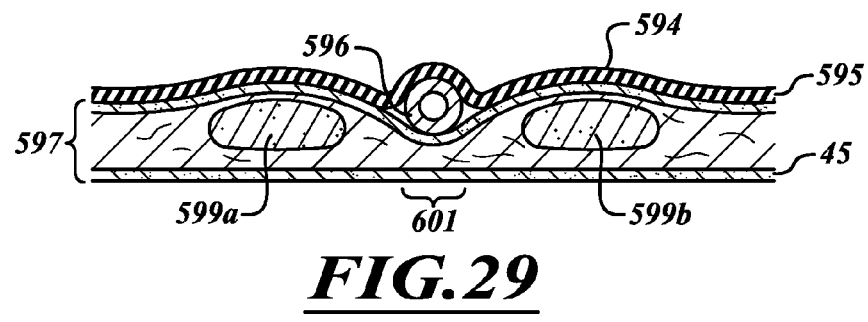
FIG. 29 is a cross-sectional view of the ablation assembly of FIG. 27 contacting an airway wall.

FIGS. 27 and 28 show a conformable balloon 594 that can be made, in whole or in part, of a highly compliant material. Highly compliant materials include, without limitation, silicon, rubber, polyethylene, polyvinyl chloride, or other materials capable of undergoing large deformation. FIG. 29 shows a sidewall 595 of the balloon 594 contacting an airway wall 597 and providing a relatively high amount of surface contact. This provides rapid and effective cooling of tissue on and near the airway wall surface while a deeper target region 601, illustrated as a section of nerve tissue, is damaged.

Figure 30:
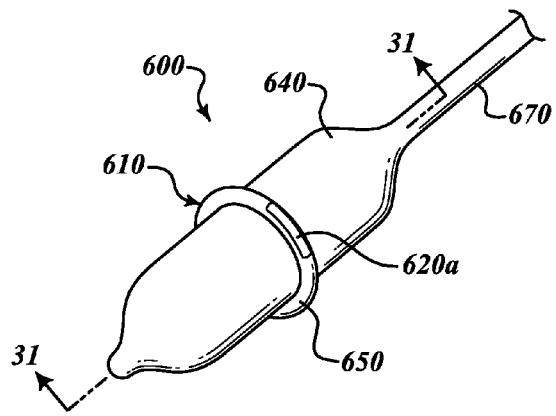
FIG. 30 is an isometric view of an ablation assembly with an integral energy emitter assembly.
Figure 31:
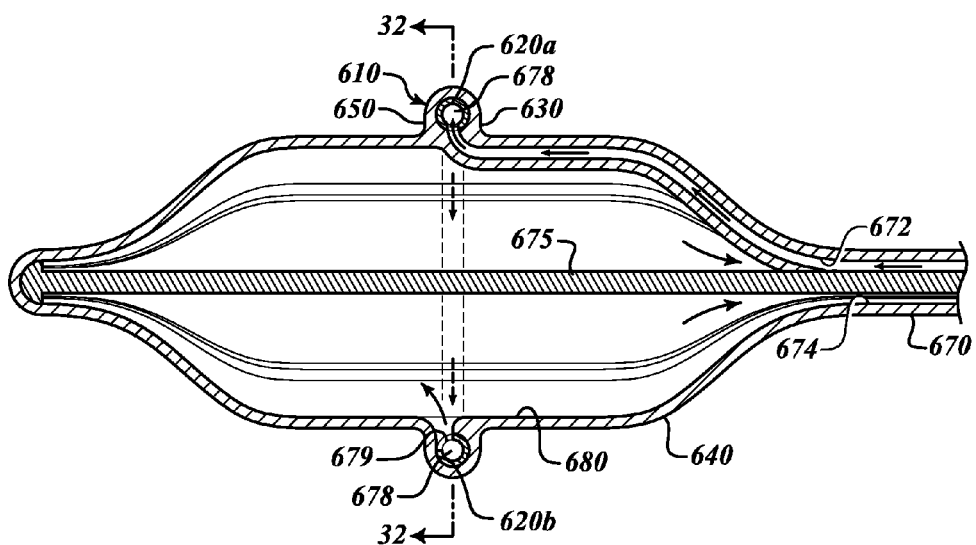
FIG. 31 is a cross-sectional view of the ablation assembly taken along a line 31-31.
Figure 32:
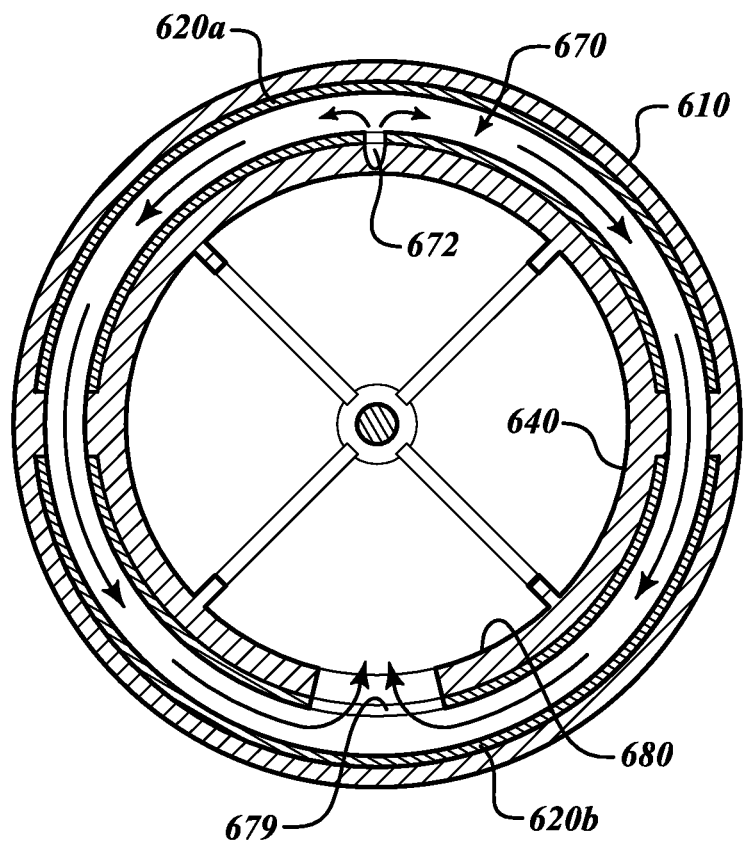
FIG. 32 is a cross-sectional view of the ablation assembly taken along a line 32-32 of FIG. 31.

FIGS. 30-32 show an ablation assembly 600 including an integral energy emitter assembly 610 with internal electrodes 620a, 620b. A generally outwardly protruding U-shaped portion 650 of a sidewall 630 can help position the electrodes 620a, 620b. An elongate body 670 extends proximally from a balloon 640 and includes a delivery lumen 672, a return lumen 674, and an interior support shaft 675. A port 679 provides fluid communication between a cooling channel 678 and a chamber 680. The coolant exits the balloon 640 via the return line 674. The sidewall 630 forms a section of the delivery lumen 672. In some embodiments, conduits (e.g., fluid lines or hoses) provide fluid communication between the elongate body 670 and the energy emitter assembly 610.

Figure 33:
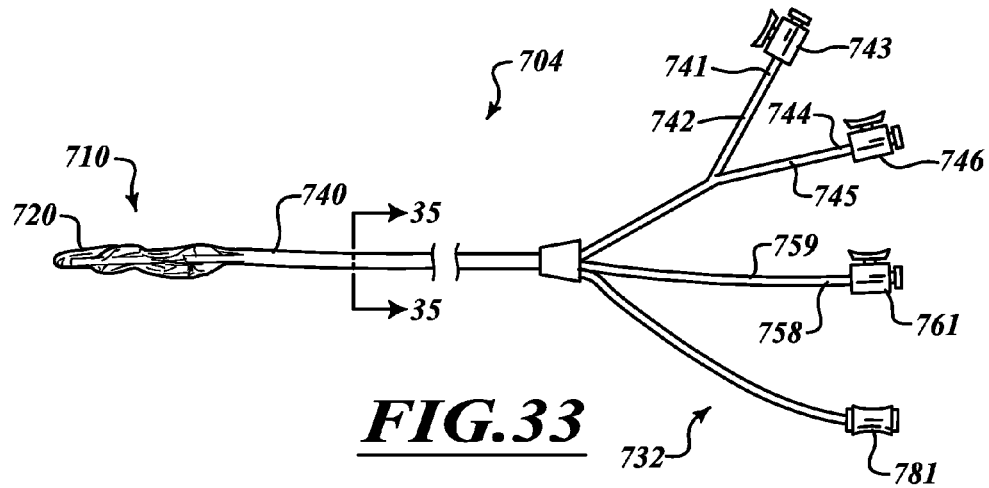
FIG. 33 is a side elevational view of a delivery device.
Figure 34:
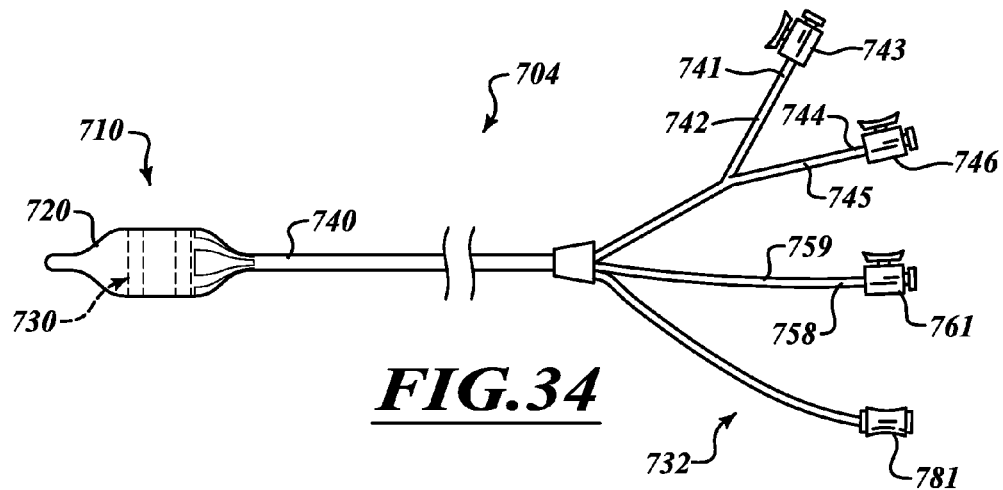
FIG. 34 is a side elevational view of the delivery device of FIG. 33 with a deployed expandable element.

FIGS. 33 and 34 show an ablation assembly 710 including an inflatable balloon 720 and an energy emitter assembly 730 (shown in dashed line in FIG. 34). Separate channels provide separate fluid paths to independently adjust the pressure in the balloon 720 and energy emitter assembly 730. Both the balloon 720 and the energy emitter assembly 730 can be made of a compliant material (e.g., urethane or other compliant biocompatible material) to fit in differently sized bronchial lumens. Advantageously, fewer catheter stock keeping units (SKUs) can be required compared to catheter balloons made from non-compliant materials, which are not optimally adjustable for fitting in different sized lumens.

The catheter 704 has a proximal section 732 configured for differential cooling. A proximal end 741 of an inflow line 742 has an inline valve 743 and is in fluid communication with an inflow lumen 750 of FIG. 35. A feed conduit 816 of FIGS. 37 and 38 delivers coolant from the inflow lumen 750 to a chamber 811 of the inflation assembly 780a.

Figure 35:
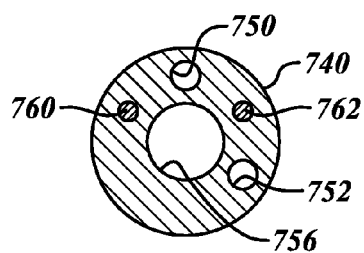
FIG. 35 is a cross-sectional view of an elongate body taken along a line 35-35 of FIG. 33.

A proximal end 744 of an inflow line 745 of FIG. 33 has an inline valve 746 and is in fluid communication with an inflow lumen 752 of FIG. 35. The inline valves 743, 746 can be connected to fluid supplies. A proximal end 758 of an outflow line 759 has an outline valve 761 and is in fluid communication with an outflow lumen 756 of FIG. 35. Power lines 760, 762 separately couple electrodes 790a, 790b respectively to a power source connector 781.

Figure 36:
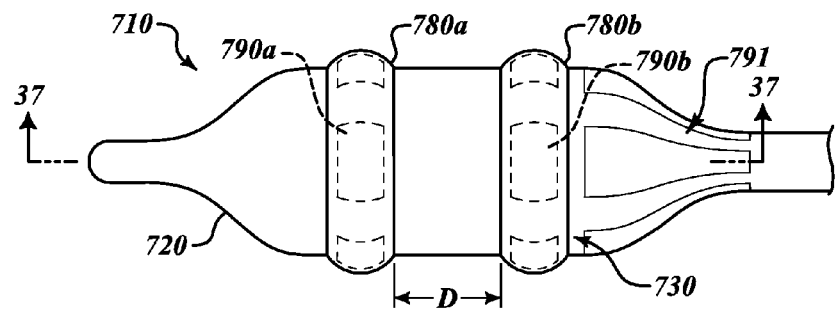
FIG. 36 is a side elevational view of an ablation assembly with inflated electrode assemblies.
Figure 37:
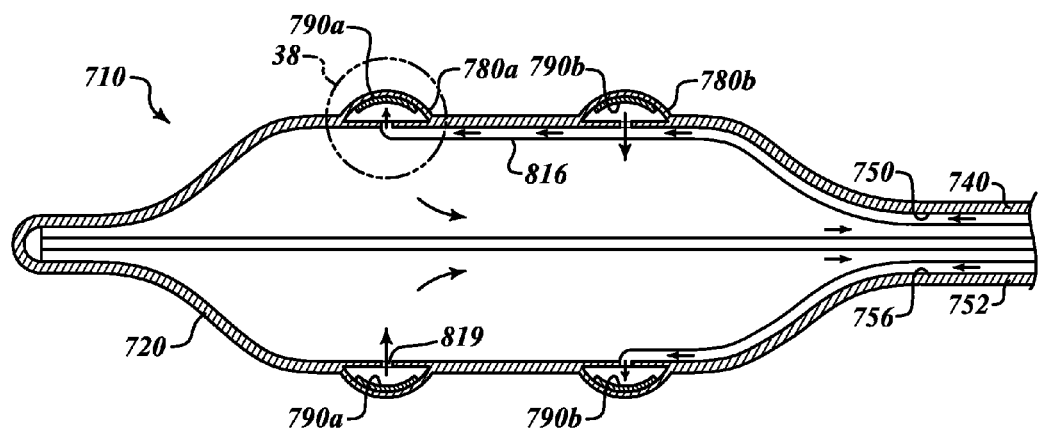
FIG. 37 is a cross-sectional view of the ablation assemblies of FIG. 36 taken along a line 37-37.
Figure 38:
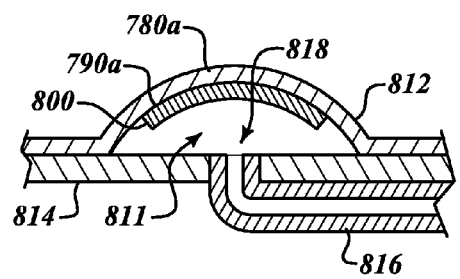
FIG. 38 is a detailed view of an electrode assembly of FIG. 37.

FIGS. 36 and 37 show inflatable ablation assemblies 780a, 780b (collectively "780") in an expanded state. The assemblies 780 can be independently inflated to help position electrodes 790a, 790b. Different coolants (e.g., saline, water, or the like) at different coolant temperatures (e.g., iced, warmed, room temperature, etc.) can flow through the ablation assemblies 780. The inflation pressure can be increased to increase the force applied to an airway wall and to help seat the ablation assemblies 780.

The ablation assemblies 780 may be spaced apart to allow each of the ablation assemblies 780 to be positioned between cartilaginous rings. For example, the distance D in FIG. 36 can be in a range of about 1 mm to about 5 mm. A physician can determine the distance D by inspecting an airway and can then select an appropriately sized catheter. In addition to being axially spaced apart, electrodes 790a, 790b may be disposed in circumferentially offset positions so as to deliver energy to different facets of the airway wall. For example, electrode 790a may be offset by 45 degrees, 90 degrees, or 180 degrees relative to electrode 790b. Further, each ablation assembly 780a, 780b may have multiple electrodes spaced circumferentially around balloon 720.

Fluids at different temperatures can be delivered to the ablation assemblies 780 and the balloon 720. In some embodiments, the coolant is delivered through cooling channels of the energy emitting assemblies 780 and then into the balloon 720 if the therapeutic goal is to produce lesions with the maximum depth. The balloon 720 and the energy emitting assemblies 780 can also be coupled to a common source (or sink) path. This allows for unique coolant flow in each path. This also may reduce the overall diameter of the expanded ablation assembly 710 as compared to using completely separate coolant paths. Electrodes 790a, 790b may be independently controlled so that energy may be delivered simultaneously or separately, and at the same or different power levels.

FIGS. 39 and 40 show an ablation assembly 800 with a deployment catheter 811 having a balloon 810 and an energy emitter assembly 820 removably positionable over the balloon 810. Energy emitter assembly 820 comprises a pair of tubular shafts 817, 819 connected by a distal loop 823. Distal loop 823 may be pre-formed around an axis parallel to the longitudinal axes of the shafts 817, 819. Alternatively the distal loop 823 can be configured to assume the deployed orientation when pressurized by the introduction of coolant in shafts 817, 819.

One of shafts 817, 819 is adapted to deliver coolant through loop 823 while the other received coolant from the loop and returns it to the proximal end of the device. In FIG. 41, the shaft 817 delivers coolant to the balloon 810. The coolant exits the balloon 810 via the shaft 819. As shown in FIG. 40, a distal tip 834 of deployment catheter 811 can be inserted and passed through a receiving opening 830 of the energy emitter assembly 820. Once an electrode, illustrated as a surface mounted electrode 836, is positioned between the distal tip 834 and a proximal end 840 of the balloon 810, the balloon 810 is inflated to snugly hold the energy emitter assembly 820.

The energy emitter assembly 820 can be moveable between a straightened and collapsed configuration for delivery and the illustrated deployed configuration. For example, in the preshaped embodiment described above, the distal loop 823 on energy emitter assembly 820 can be straightened and collapsed inwardly so as to be positionable in a constraining sheath during introduction. Upon removal from the sheath, distal loop 823 will return to its unbiased deployed orientation, lying in a plane generally perpendicular to the longitudinal axes of shafts 817, 819. In alternative embodiments, the distal loop 823 may be flaccid and collapsible when unpressurized, and will assume the desired deployed shape when coolant is introduced through shafts 817, 819. To manufacture distal loop 823, a polymer tube may be heat treated to assume a desired shape when pressurized.

By decoupling the energy emitter apparatus 820 from the deployment catheter 811 they may be introduced separately from each other, allowing the apparatus to be introduced through very small-diameter passageways. This is particularly useful to allow the ablation assembly to be inserted through a working channel of a bronchoscope. First, the energy emitter assembly 820 may be collapsed and introduced through the working channel (with or without a sheath), then the deployment catheter 811 may be introduced. The combined apparatus may then be assembled within the airway.

As shown in FIGS. 41 and 42, fluids can be independently delivered through the energy emitter assembly 820 and the balloon 810. FIG. 41 shows arrows representing coolant flowing through the energy emitter assembly 820. FIG. 42 shows arrows representing coolant flowing through the balloon 810. The coolant can flow through a delivery lumen 854 and a port 856. The coolant exits a chamber 857 via a port 860 and flows through a return lumen 864. A separate delivery lumen 867 delivers coolant to the energy emitter assembly 820. A return lumen 869 delivers the coolant out of the energy emitter assembly 820. In some embodiments, coolants are independently delivered to the balloon 810 and the energy emitter assembly 820. Separate lines can be connected to the balloon 810 and the energy emitter assembly 820.

One or move valves can provide for different flow rates through the balloon 810 and the energy emitter assembly 820. For example, a valve system (e.g., one or more valves, throttles, etc.) can provide a first flow rate of coolant through the energy emitting assembly 220 and a second flow rate of coolant through the balloon 810. The first flow rate can be significantly different from the second flow rate. For example, the first flow rate can be significantly greater than the second flow rate. In yet other embodiments, the first flow rate can be generally the same as the second flow rate.

Figure 43:
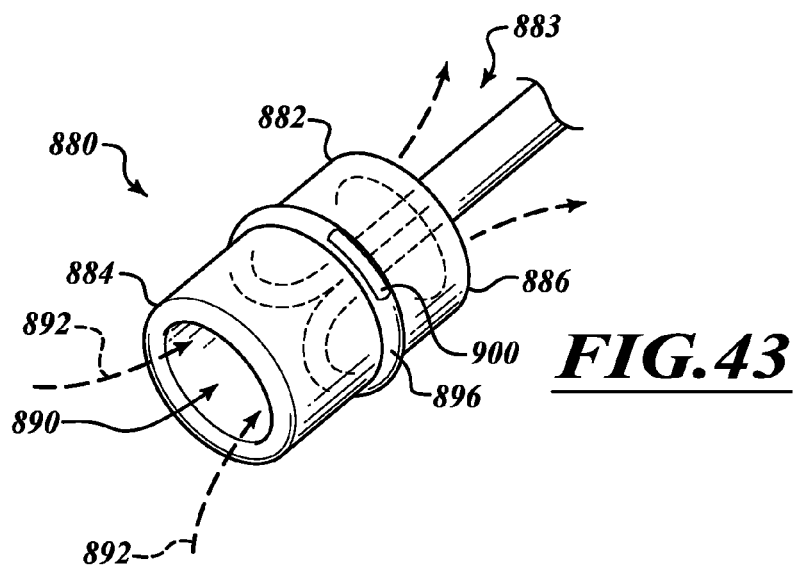
FIG. 43 is an isometric view of an ablation assembly during exhalation.
Figure 44:
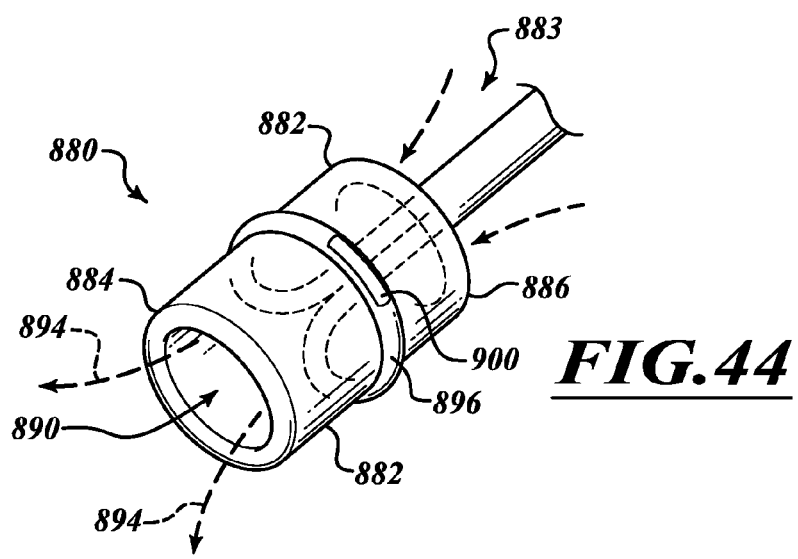
FIG. 44 is an isometric view of the ablation assembly of FIG. 43 during inhalation.
Figure 45:
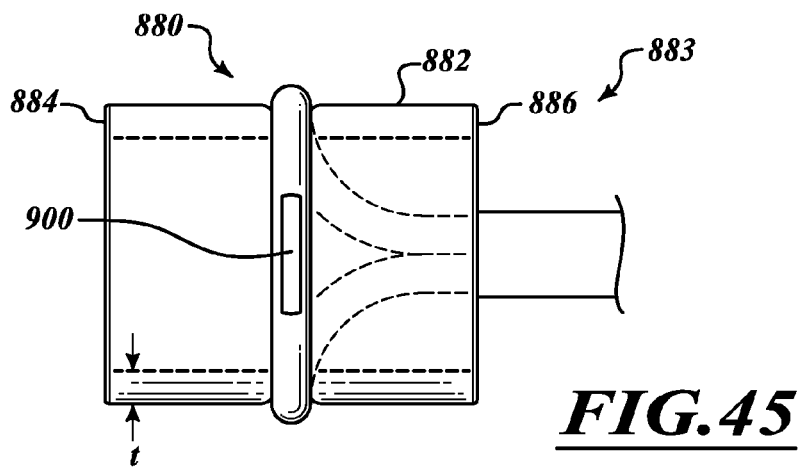
FIG. 45 is a top plan view of the ablation assembly of FIG. 43.

Referring to FIGS. 43-45, a catheter 883 can provide ventilation during ablation treatment of an airway. An expandable element 882 has a distal end 884, a proximal end 886, and a ventilation passageway 890 extending between the ends 884, 886. The expandable element 882 can be a double-walled cylindrical balloon defining a cylindrical chamber between its inner and outer walls. The spacing between the inner and outer walls t (see FIG. 45) can be sufficiently large to permit enough fluid to circulate in the element 882 to expand the energy emitting assembly 896 into engagement with the airway wall and to effectively control tissue temperatures.

The ventilation passageway 890 is configured to allow expiratory airflow, represented by arrows 892 in FIG. 43, and inspiratory airflow, represented by arrows 894 in FIG. 44. A flow velocity sensor can be positioned along the passageway 890 to determine changes in air flow due to the treatment. Additionally or alternatively, a valve (e.g., a one-way valve, a two-way valve, etc.) or flow regulator can be used to control air flow. Such elements can be installed in the passageway 890.

As in the embodiment of FIGS. 39-42, the energy emitter assembly 896 and the expandable element 882 may be independently deployable. The energy emitter assembly 896 can be inflated from a delivery configuration (e.g., a straight configuration) to the illustrated treatment configuration (illustrated as a loop). The expandable element 882 can be inflated to the illustrated tubular configuration. The inflated ends 884, 886 can press against the airway to securely hold the electrode 900 stationary with respect to the expandable element 882. A coolant can circulate through an energy emitter assembly 896 and into the inflatable element 882. For enhanced differential cooling, different coolants can flow through the energy emitter assembly 896 and the inflatable element 882.

Figure 46:
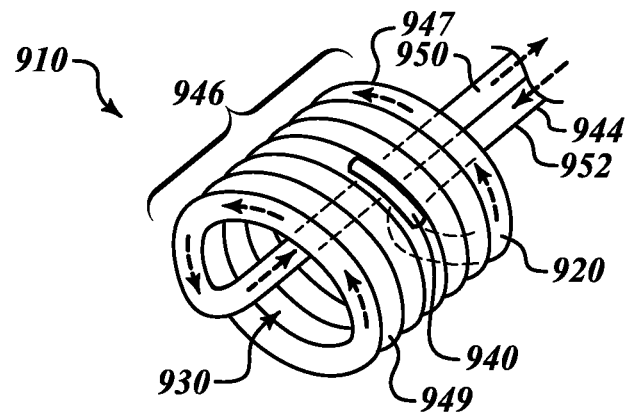
FIG. 46 is an isometric view of a coiled ablation assembly.

FIG. 46 shows an ablation assembly 910 with a coiled energy emitter assembly 920. Coolant flows through a delivery line 944 and a coiled section 946. The coolant absorbs thermal energy from tissue near the coiled section 946. The coolant also cools the electrode 940. The coolant flows to a distal end of the ablation assembly 910 and returns proximally via a return line 950. The delivery line 944 and the return line 950 form the catheter shaft 952. In this manner, both the airway wall and the electrode 940 are simultaneously cooled without utilizing a separate balloon.

The coiled section 946 can be formed of a hollow tubular member and has seven coil turns. The number of coil turns can be increased or decreased to increase or decrease the axial length of the coiled section 946. Each coil turn can be connected to an adjacent coil turn to prevent separation. Alternatively, adjacent coil turns may not be physically coupled together to allow the ablation assembly 910 to uncoil for delivery through airways.

The ablation assembly 910 can be inflated to assume the coiled configuration and can be made, in whole or in part, of a pre-formed material, such as PET or other thermoformed material. Alternatively, the ablation assembly 910 can be formed of shape memory material that assumes different configurations when thermally activated or when released from a constrained configuration.

To help facilitate contact between the electrode 940 and tissue, the electrode 940 can protrude outwardly. The electrode 940 can be a surface mounted plate. In other embodiments, the electrode 940 is a conductive coating.

Figure 47:
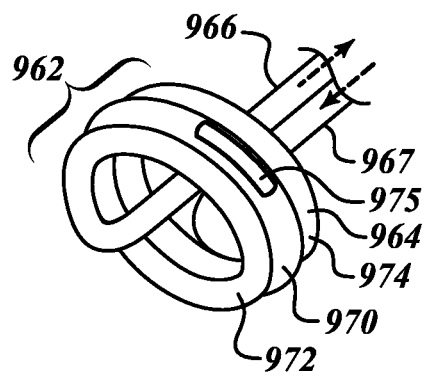
FIG. 47 is an isometric view of a coiled ablation assembly with an enlarged coil.

FIG. 47 shows a coiled section 962 having a tubular member 964 with three coil turns. The central coil turn 970 can be slightly larger than the adjacent coils 972, 974, such that an electrode 975 is positioned radially outward of the coils. Coolant can flow through a delivery line 967, through the coiled section 962, and return via a return line 966. In some embodiments, an inner coil pushes the coil turn 970 outwardly.

Figure 48:
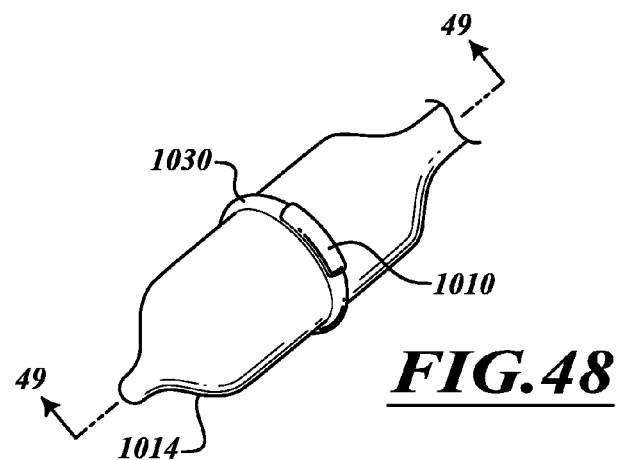
FIG. 48 is an isometric view of an ablation assembly with an open cooling channel.
Figure 49:
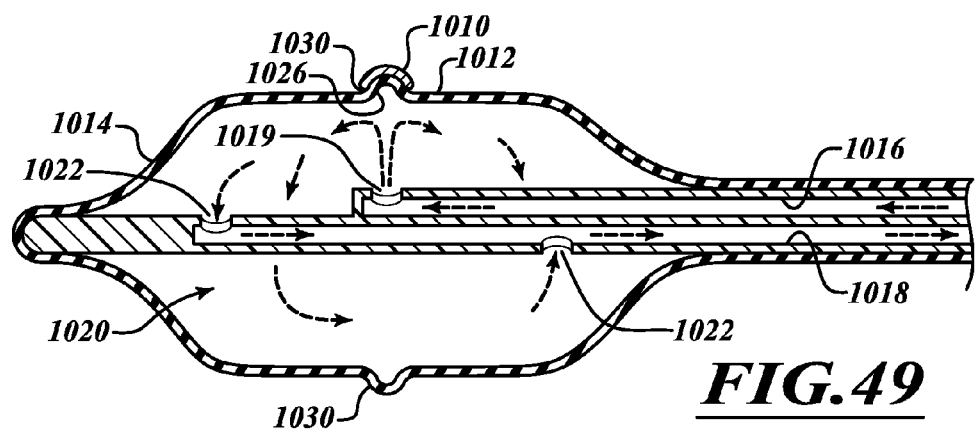
FIG. 49 is a cross-sectional view of the ablation assembly of FIG. 48 taken along a line 49-49.

FIGS. 48 and 49 show an open cooling channel in communication with a chamber of a balloon. An electrode 1010 is mounted to the exterior of balloon 1014. An annular rib 1030 can be formed in the wall of balloon 1014, and the electrode 1010 may have a curved cross-sectional shape which nests over the annular rib to help maintain the position of electrode 1010 and to create greater surface area for heat transfer between the balloon and the electrode. Coolant can be delivered through a delivery lumen 1016. The coolant passes through a port 1019 into a chamber 1020 of a balloon 1014. The port 1019 is configured to direct the coolant towards the electrode 1010 in the form of a stream or spray to cool the electrode. The coolant circulates and exits the chamber 1020 via a port 1022. The coolant flows proximally along a return lumen 1018. To enhance cooling capabilities, the flow of coolant is aimed and delivered towards the electrode 1010.

Figure 50:
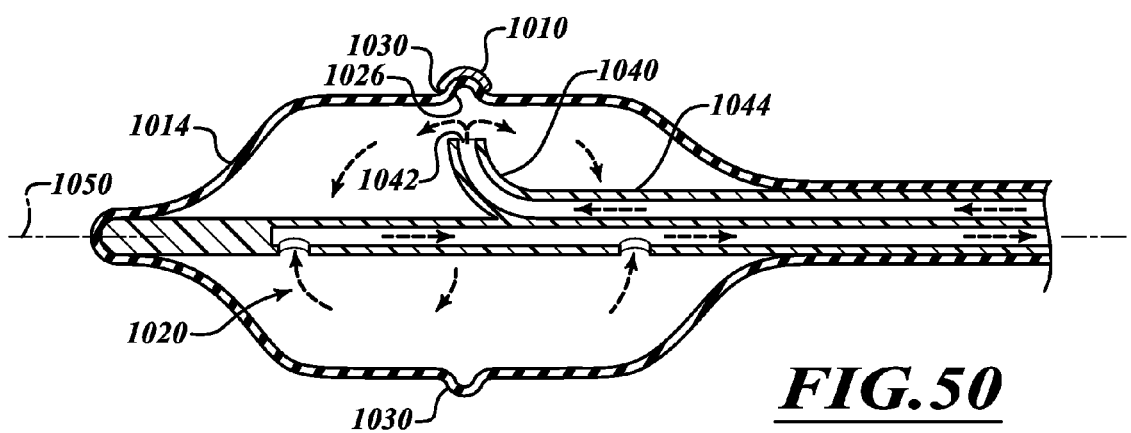
FIG. 50 is a longitudinal cross-sectional view of an ablation assembly in accordance with another embodiment.

As shown in FIG. 50, a delivery conduit 1044 has a tip 1040 that extends laterally away from a longitudinal axis 1050 towards the electrode 1010 such that an outlet port 1042 is positioned in close proximity to electrode 1010. Coolant can exit the port 1042 and flow directly toward electrode 1010 to maximize cooling thereof.

Figure 51:
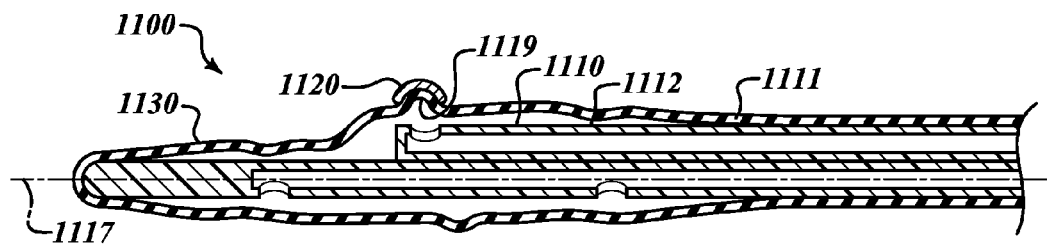
FIG. 51 is a longitudinal cross-sectional view of an ablation assembly with an actuatable delivery conduit.
Figure 52:
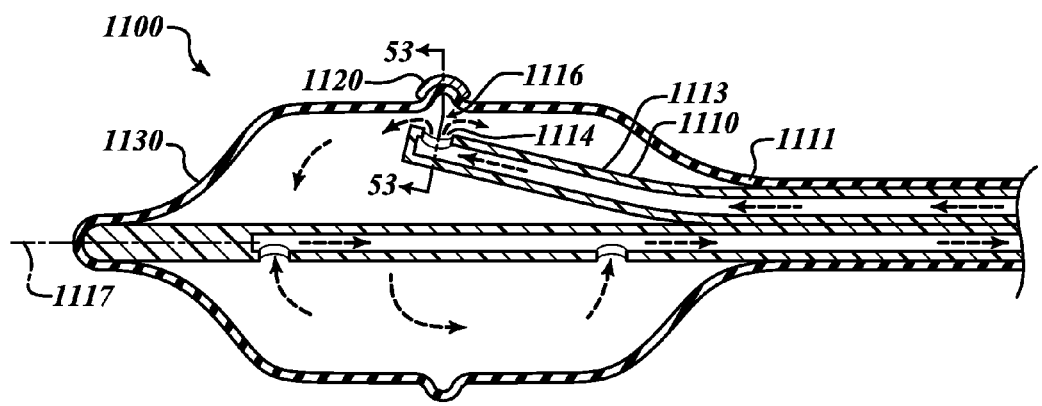
FIG. 52 is a cross-sectional view of the ablation assembly of FIG. 51 in a deployed configuration.

FIG. 51 shows a deflectable delivery conduit 1110 of an elongate body 1111 movable from a delivery position 1112 to a deployed position 1113 of FIG. 52. The delivery conduit is resiliently biased into the deployed position 1113. A deflated balloon 1130 can hold the delivery conduit 1110 in the straight configuration until the balloon 1130 is inflated. Both the balloon 1130 and the biased delivery conduit 1110 can be deployed together. In other embodiments, the delivery conduit 1110 is made of a shape memory material that moves when activated. For example, the delivery conduit 1110 can move from the delivery position 1112 to the deployed position 1113 when heated.

Figure 53:
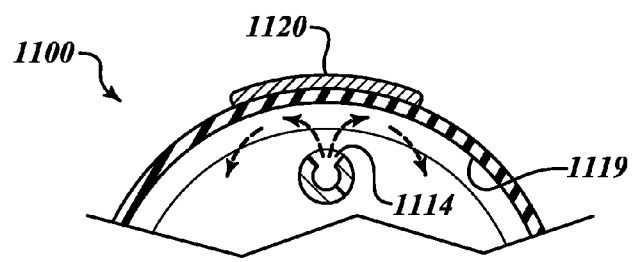
FIG. 53 is a cross-sectional view of a portion of the ablation assembly of FIG. 52 taken along a line 53-53.

With reference to FIG. 53, the port 1114 is closer to a cooling channel 1119 than to a longitudinal axis 1117 (FIG. 52). A fluid jet flows out of the port 1114 and into the channel 1119. The coolant can flow along the entire length and width of the electrode 1120 to provide generally uniform electrode cooling. When the balloon 1130 is deflated, the delivery conduit 1110 is moved back to a generally midline position.

Figure 54:
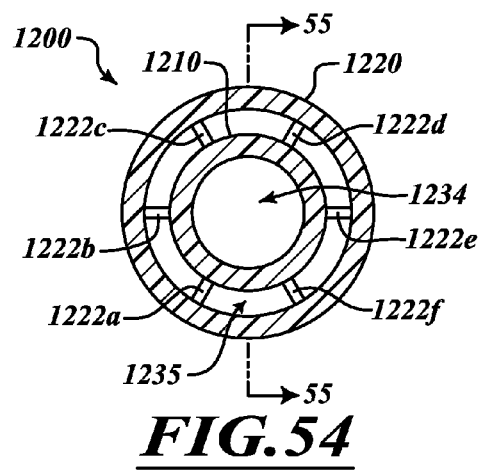
FIG. 54 is a transverse cross-sectional view of an energy emitter assembly.
Figure 55:
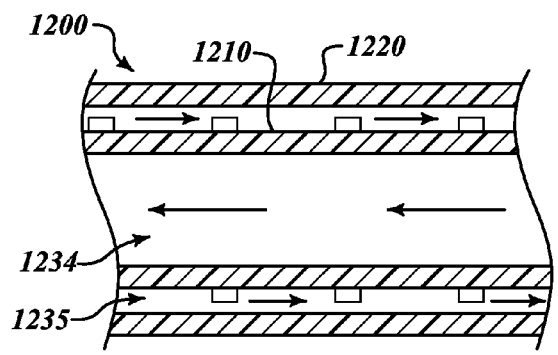
FIG. 55 is a cross-sectional view of the energy emitter assembly of FIG. 54 taken along a line 55-55.

FIGS. 54 and 55 show a portion of an energy emitter assembly 1200 that includes an internal electrode 1210 in an outer member or conduit 1220. Spacers 1222a, 1222b, 1222c, 1222d, 1222e, 1222f (collectively "1222") space the electrode 1210 from the outer member 1220. The electrode 1210 has an inner cooling channel 1234. An outer cooling channel 1235 is between the electrode 1210 and the outer member 1220. As shown in FIG. 55, a coolant can flow in one direction through the cooling channel 1234 and a coolant can flow in the opposite direction through channel 1235.

Figure 56:
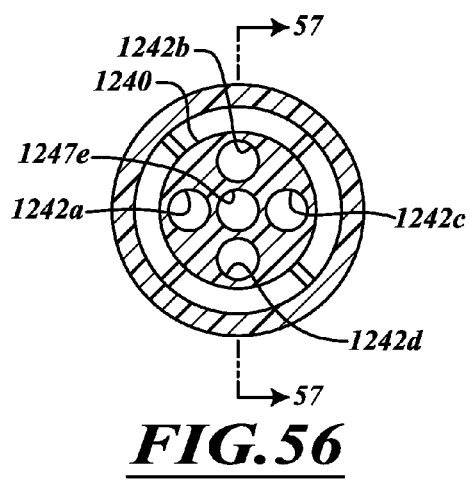
FIG. 56 is a transverse cross-sectional view of an energy emitter assembly with a multi-lumen electrode.
Figure 57:
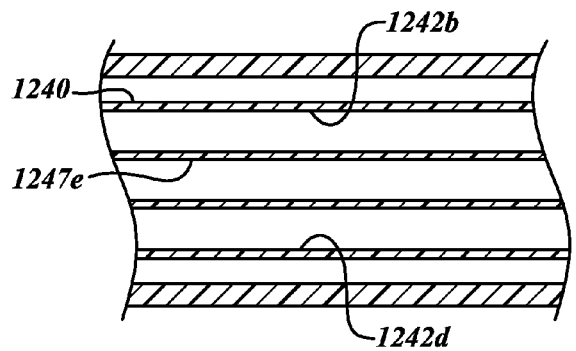
FIG. 57 is a cross-sectional view of the energy emitter assembly of FIG. 56 taken along a line 57-57.

FIGS. 56 and 57 show an electrode 1240 that has a plurality of cooling channels 1242a, 1242b, 1242c, 1242d, 1242e (collectively "1242"). The same fluid can be delivered through all of the channels 1242. Alternatively, different fluids at different temperatures can be delivered through the channels 1242. In some embodiments, coolant flows through some of the channels 1242 in one direction and a different coolant can flow through other channels 1242 in the opposite direction.

Figure 58:
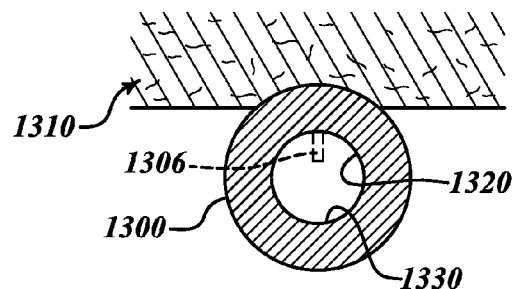
FIGS. 58 and 59 are cross-sectional views of an electrode contacting tissue.
Figure 59:
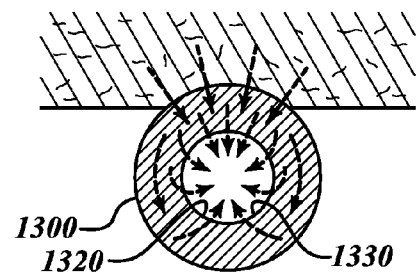

With reference to FIGS. 58 and 59, an electrode 1300 comprises a metal tube. Heat can be conducted about the circumference of the electrode 1300 and into the coolant in a cooling channel 1320. The flow of heat is shown in FIG. 59. Heat can be generally uniformly transferred along the wall of the electrode 1300 so that heat is absorbed by the coolant flowing along the interior surface 1330.

Electrodes can include one or more heat transfer elements for enhancing heat transfer. FIG. 58 shows an optional heat transfer element in the form of a fin 1306, illustrated in dashed line, extending into the coolant channel 1320. Any number of inwardly extending fins can be located in the coolant channel 1320 for enhanced heat transfer via convention. The fins can be made of a material that has a high thermal conductivity. Other types of heat transfer elements or features (e.g., surface texturing) can be used to control heat transfer.

Figure 60:
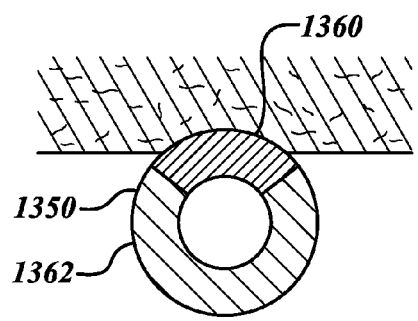
FIGS. 60 and 61 are cross-sectional views of an electrode with a thermally conductive portion contacting tissue.
Figure 61:
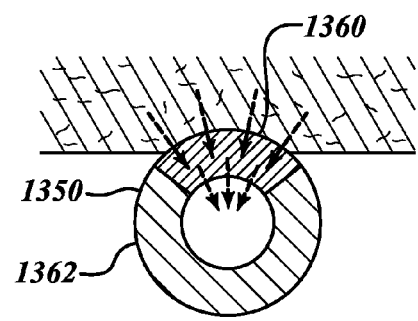

FIGS. 60 and 61 show an electrode 1350 that has a thermally conductive portion 1360 and an insulating portion 1362. The thermally conductive portion 1360 can be made, in whole or in part, of metal or other material with a high thermal conductivity. The insulating portion 1362 can be made of an insulating material, such as rubber, plastic, or the like. As shown in FIG. 61, heat transfer is generally isolated to the thermally conductive portion 1360 to prevent excessive heating of the insulating member 1362, which may be in contact with a temperature sensitive element, such as a balloon.

Figure 62:
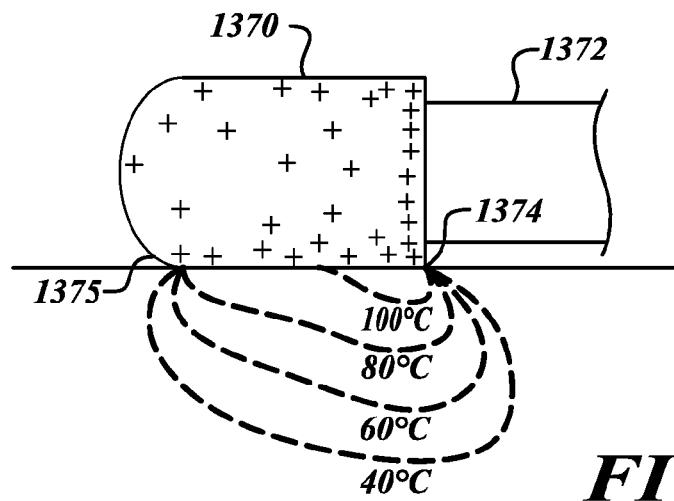
FIGS. 62 and 63 are side elevational views of electrodes heating tissue.

If electrodes have sharp edges at one or both ends, electrons have a tendency to accumulate near those sharp edges and other irregularities. The voltage near the edges is often higher than in other regions of the electrode. FIG. 62 shows an electrode 1370 connected to an insulating member 1372, and an applied charge, represented by plus signs, tends to accumulate along the sharp edge 1374. The high charge causes excessive heating and is referred to as an "edge effect." When the highly charged edge 1374 contacts tissue, the high regional voltage near the electrode edge 1374 results in more power being delivered to the tissue contacting or proximate to the edge 1374. Thus, that tissue becomes hotter than other tissue contacting the electrode 1370. This results in non-uniform heating of the tissue and unwanted hot spots. During RF ablation, lesion formation can be very uneven and excessive tissue damage, and is commonly referred to as edge effects.

Figure 63:
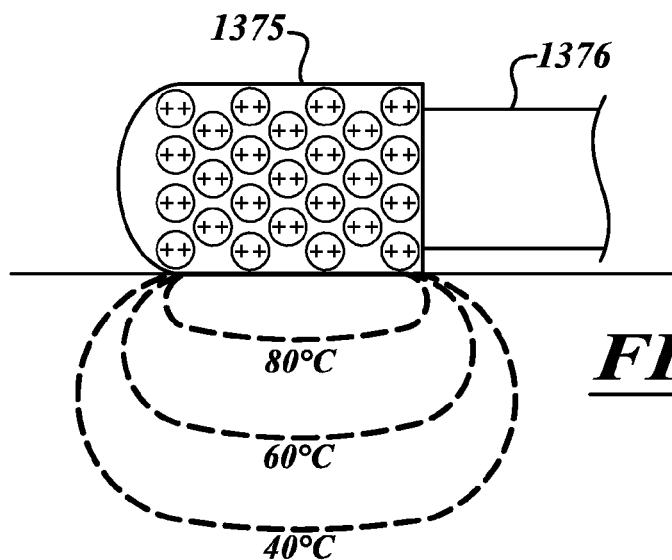

FIG. 63 shows an electrode 1375 connected to an insulator 1376. The electrode 1375 is formed of a plurality of individual electrodes. One or more of the individual electrodes may have sharp edges, but the electrodes are sufficiently small such that the charge density is relatively uniform across the length and breadth of the overall electrode 1375. The charges are generally evenly distributed to minimize, limit, or substantially eliminate edge effects. This results in generally uniform temperatures along the length of the electrode 1375, as shown in FIG. 63.

Figure 64:
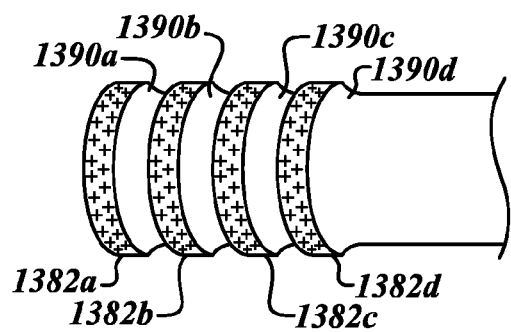
FIG. 64 is a side elevational view of an electrode assembly with ring electrodes.

FIG. 64 shows a plurality of discrete spaced apart electrode elements, illustrated as electrode rings 1382a, 1382b, 1382c, 1382d (collectively "1382"). Each electrode ring 1382 comprises a plurality of individual electrodes to mitigate edge effects. Insulating portions 1390a, 1390b, 1390c, 1390d (collectively "1390") insulate the electrode rings 1382.

Figure 65:
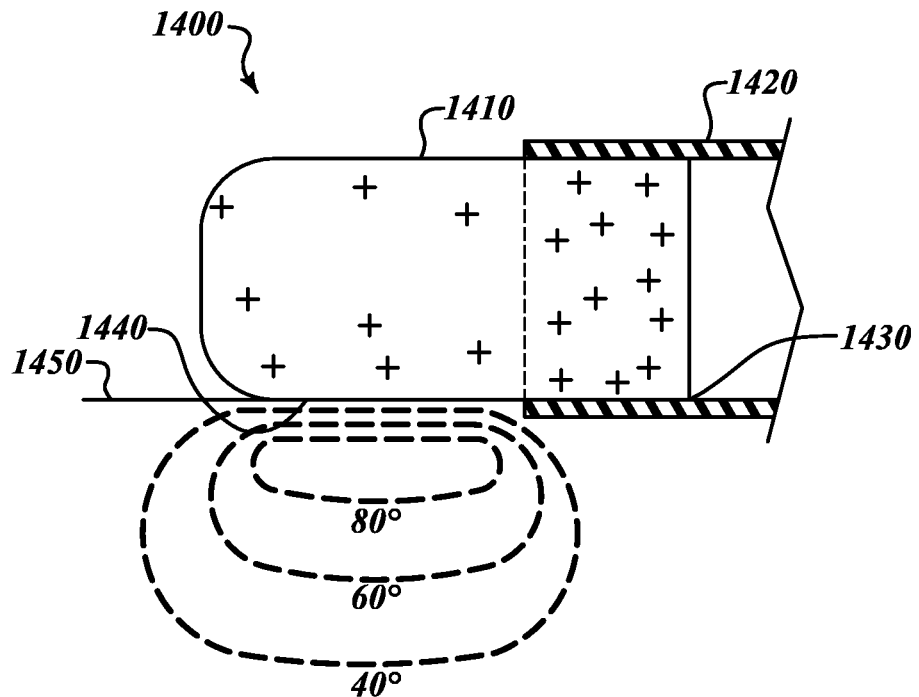
FIG. 65 is a side elevational view of a shielded electrode heating tissue.

FIG. 65 shows an edge 1430 of an electrode element 1410 covered by shielding 1420. An exposed contact surface 1440 of the electrode element 1410 can contact tissue 1450 and can result in generally uniform heating. The shielding 1420 can be an insulating material that inhibits or blocks energy outputted by the electrode element 1410. If the electrode element 1410 outputs electrical energy, the shielding 1420 can be made of an electrically insulating material, such as non-conductive plastic or polymer or other dielectric material.

Figure 66:
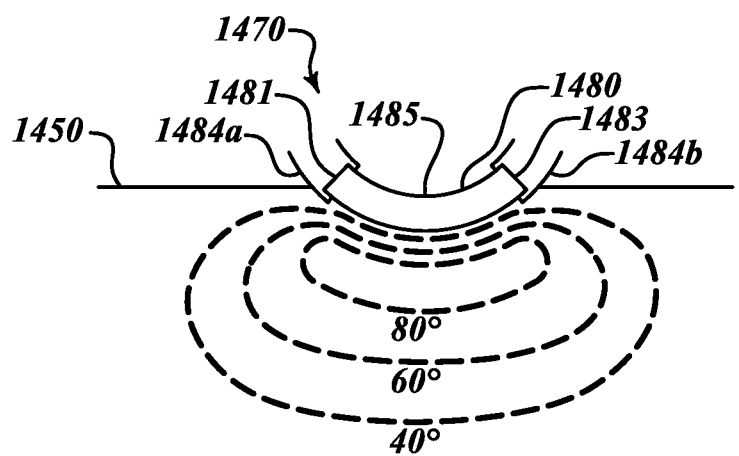
FIG. 66 is a side elevational view of an arcuate shielded electrode heating tissue.

FIG. 66 shows an ablation assembly 1470 that includes an electrode 1480 and shielding portions 1484a, 1484b (collectively "1484"). The electrode 1480 has a first end 1481, a second end 1483, and a main body 1485. Shielding portions 1484a, 1484b cover the ends 1481, 1483 and can be part of an ablation energy insulator. A generally uniform temperature distribution can be produced along a length of the exposed electrode 1480. The length of overlap between the electrode 1480 and the shielding portions 1484 can be selected based on the application. In some embodiments, a length of about 4 mm of the electrode 1480 can be received within each of the shielding portions 1484. The length of the exposed section of the electrode 1480 can be in the range of about 6 mm to 10 mm. The length of the electrode 1480 can be about 8 mm. Other dimensions are also possible.

The shielding portions 1484a, 1484b can be cooling conduits. Coolant can flow through the shielding portions 1484 and through a cooling channel of the electrode 1480. In other embodiments, a Peltier device is used to cool the electrode 1480. It will be understood that any of the electrode embodiments of FIGS. 54-66 may be utilized in any of the energy emitter assemblies disclosed in this application.

Lesion shapes can be controlled by adjusting the temperature of the coolant, coolant flow rates, heat carrying capacity of coolants, thermal characteristics of the balloon (e.g., the heat transfer properties of the balloon), or the amount of delivered power. FIGS. 67A-71B show temperature profiles and corresponding lesions formed by progressively increased cooling by a balloon. The cooling capacity of the balloon can be increased by decreasing the coolant temperature or by increasing the coolant flow rate, or both. Lesion shaping can also be achieved by holding the cooling capacity of the balloon generally constant while varying the coolant capacity of the electrode or by increasing or decreasing the power delivered to the tissue. By way of example, the ablation assembly 208 in FIG. 8 can be used to form the lesions of FIGS. 67B, 68B, 69B, 70B, and 71B. Because the balloon 212 has a larger diameter than the electrode channel 340, there is a relatively low flow velocity along the balloon surface as compared to the high velocity low velocity through the electrode 214. This results in differential cooling. If the electrode 214 and the balloon 212 have independent flows, the coolants can be at different temperatures and/or flow velocities for differential cooling. The ablation assembly 800 of FIGS. 39-42 can be used for differential cooling. The power delivered by the electrode 836 to the tissue can be fixed. The coolant flow rate through the energy emitter assembly 820 can be fixed. The coolant flow rate through the balloon 810 can be varied to form lesions of different shapes.

Figure 67A:
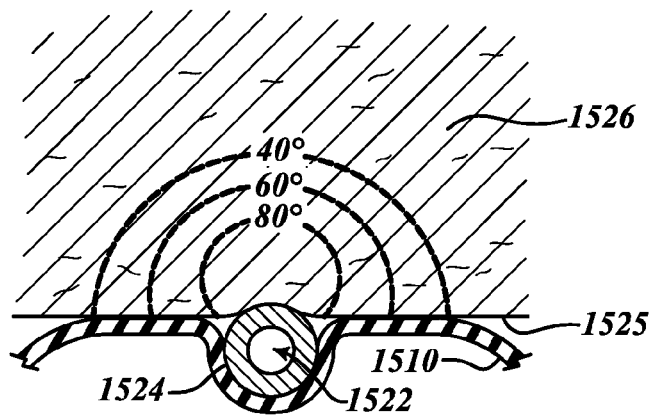
FIGS. 67A-71B show isotherms and corresponding lesions.
Figure 67B:
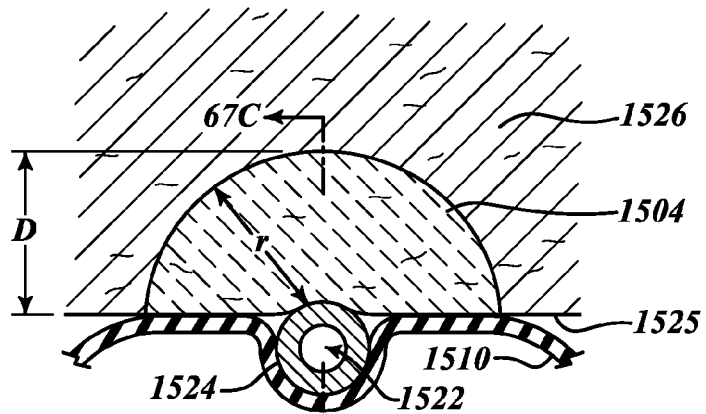
Figure 67C:
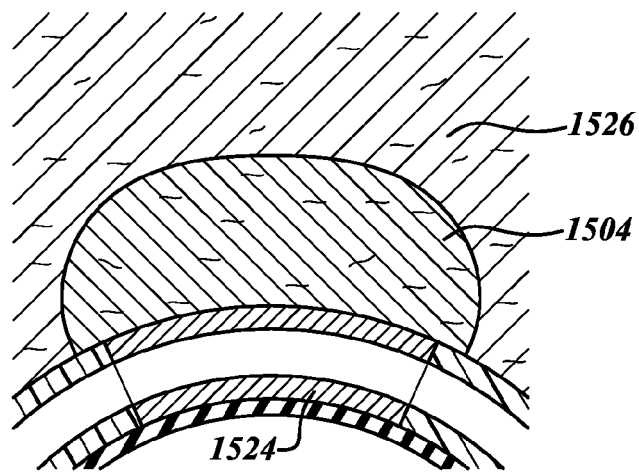

FIG. 67A shows isotherms and temperature distributions in tissue, with isotherms of 80° C., 60° C., and 40° C. FIG. 67B shows a lesion 1504 corresponding to the isotherms of FIG. 67A. The coolant in a cooling channel 1522 is the only coolant that absorbs a significant amount of heat. A balloon 1510 does not absorb a significant amount of thermal energy and can be filled with fluid at a temperature that is generally equal to room temperature or within a range of about 20° C.-30° C. In some embodiments, the balloon 1510 is inflated with ambient air and can hold an electrode 1524 against the tissue 1500. In other embodiments, the balloon 1510 is inflated with warm saline.

FIG. 67B shows the lesion 1504 having a generally semi-circular shape. The radius r and depth D can be increased or decreased by decreasing or increasing, respectively, the temperature of the coolant in the cooling channel 1522. Additionally or alternatively, the radius r and depth D can be increased or decreased by decreasing or increasing, respectively, the flow rate of the coolant.

Figure 68A:
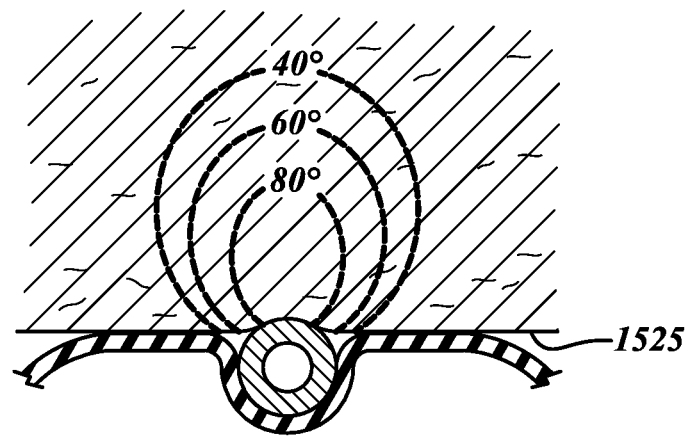
Figure 68B:
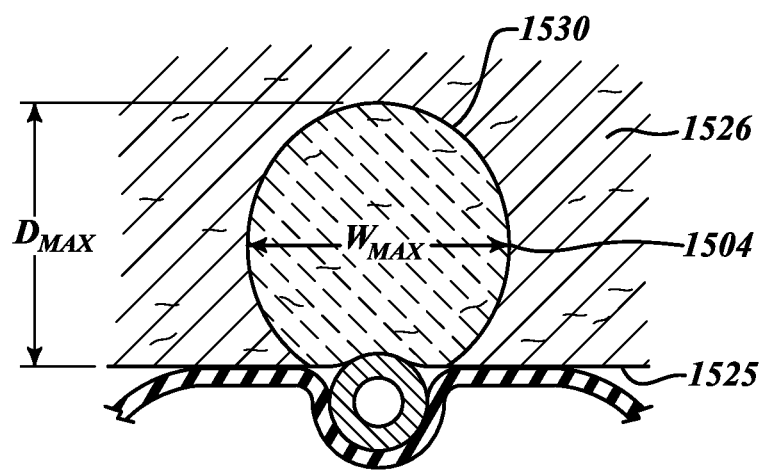

Chilled coolant can be delivered through the balloon 1510 to reduce the cross-sectional width of the lesion at the tissue surface 1525. FIGS. 68A and 68B show isotherms and a corresponding lesion 1527 when a coolant cools the electrode 1524 and when a low temperature coolant flows at a low velocity through the balloon 1510. The coolant in the balloon 1510 absorbs a sufficient amount of thermal energy to protect tissue that contacts or is proximate to the balloon-tissue interface.

The lesion can have a generally elliptical shape. In some embodiments, including the illustrated embodiment of FIG. 68B, the cross-sectional width of the lesion 1504 at the surface 1525 is less than a cross-sectional width of the lesion 1504 of FIG. 67B at the surface 1525. The cross-sectional width of the lesion 1504 of FIG. 68B increases with depth to a maximum width $W_{Max}$ and then decreases to the deepest region 1530. The maximum width $W_{Max}$ is less than the depth D of the lesion 1504. FIG. 68B shows the lesion 1527 at the surface 1525 having a width that is no more than about 150% of the electrode width. FIG. 69B shows a maximum cross-sectional width of the lesion 1527 at the tissue surface 1525 that is about equal to the electrode width.

Figure 69A:
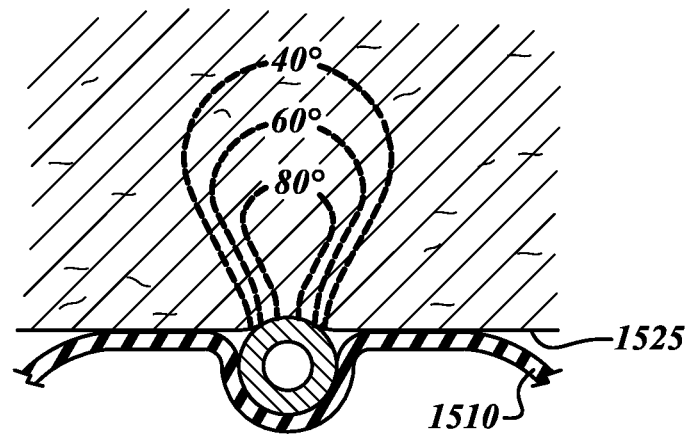
Figure 69B:
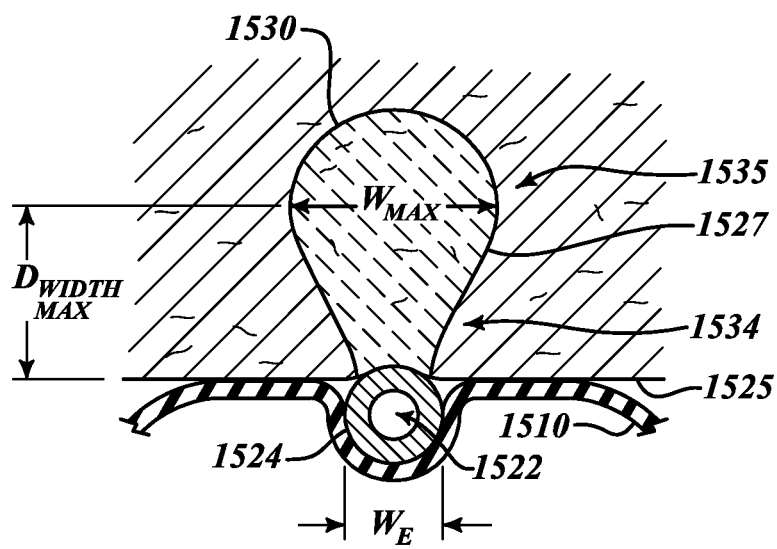

FIGS. 69A and 69B show isotherms and a lesion 1527 when a low temperature coolant flows at a high velocity through the balloon 1510 or a very low temperature coolant flows at a low velocity through the balloon 1510. The somewhat teardrop shaped lesion 1527 extends from the tissue surface 1525. The width of a shallow or narrowed portion 1534 of the lesion 1527 is about equal to the cross-sectional width $W_E$ of the electrode 1524. Thus, the lesion 1527 at the surface 1525 has a maximum cross-sectional width that is no more than about 150% of an electrode-tissue interface. This ensures that a minimal amount of surface tissue is damaged. The lesion 1527 tapers outwardly from the shallow portion 1534 to an enlarged region 1535. The lesion cross-sectional width gradually increases with depth to a maximum width $W_{Max}$. The maximum width $W_{Max}$ can be more than about 1 to about 3 times the cross-sectional width at the surface 1525. The deepest region 1530 of the lesion 1527 has a partially circular shape.

Figure 70A:
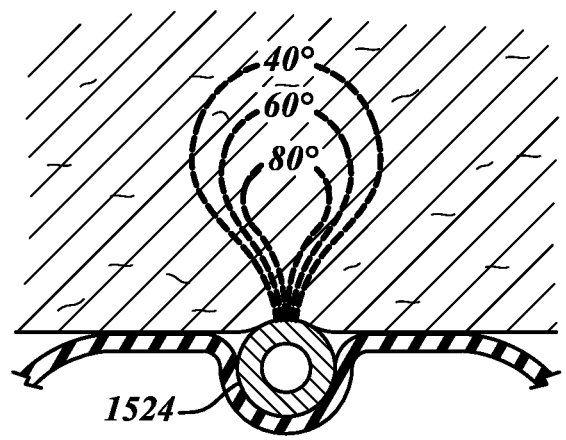
Figure 70B:
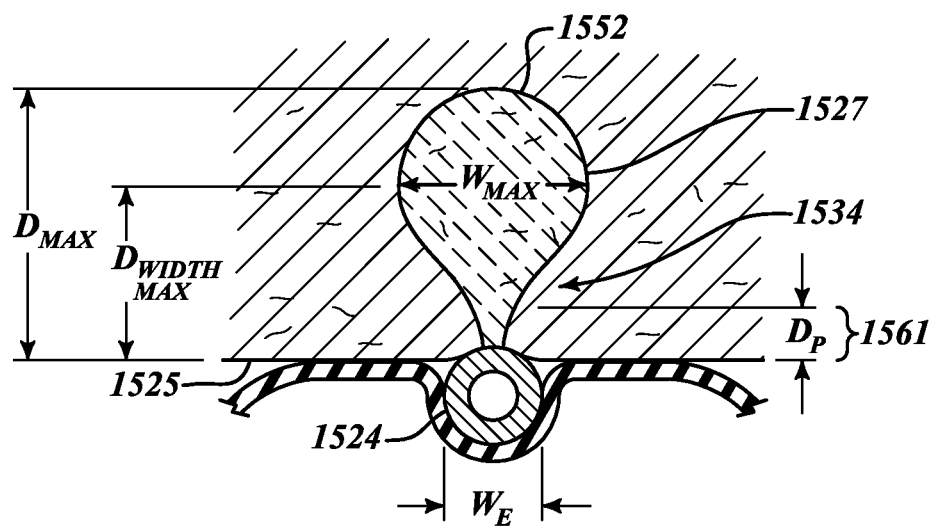

FIGS. 70A and 70B show isotherms and a teardrop shaped lesion 1527 that can be formed when a very low temperature coolant flows at a high velocity through the balloon 1510. The lesion 1527 extends from the tissue surface 1525 and has a narrow shallow region 1534 that rapidly expands outwardly to a wide deep region 1552. The width of the shallow portion 1534 is less than a width $W_E$ of the electrode 1524. The cross-sectional width rapidly increases with depth to a maximum width $W_{Max}$. Thus, most of the volume of the lesion 1527 is deep in the tissue. As such, the depth of the centroid of area is significantly greater than the width of the lesion 1527 at the surface 1525.

Figure 71A:
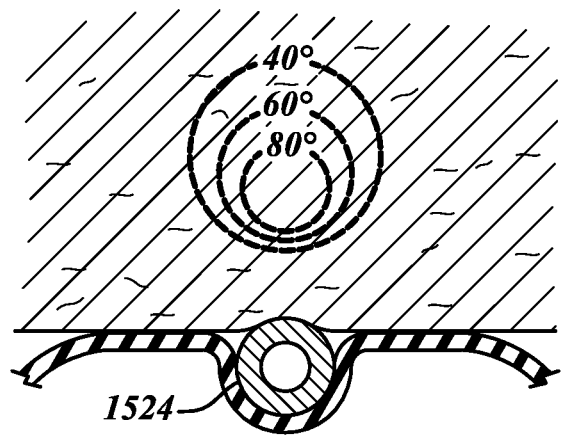
Figure 71B:
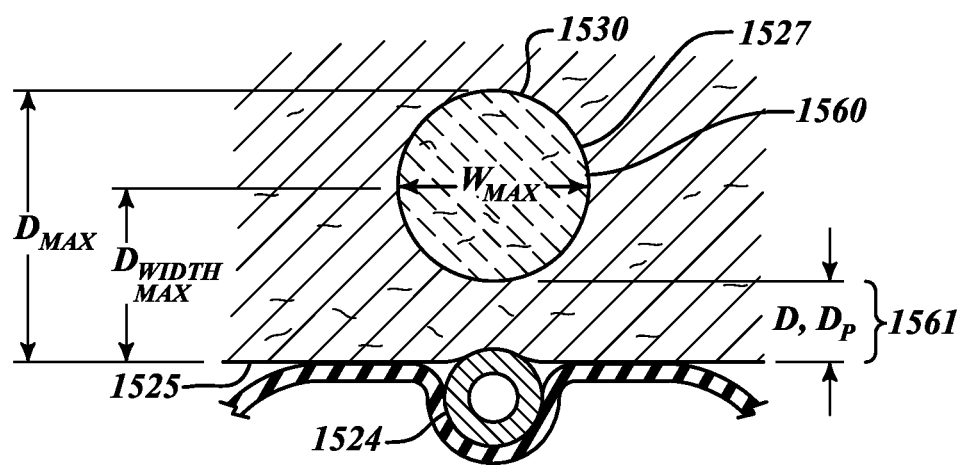

FIGS. 71A and 71B show isotherms and a corresponding circular shaped lesion 1527 that can be formed when a very low temperature coolant flows at a very high velocity through the balloon 1510. The lesion 1527 is disposed at a depth D from the tissue surface 1525. The maximum cross-section width $W_{Max}$ of the lesion 1527 is at a depth $D_{Width\ Max}$. The lesion 1527 is spaced apart from the electrode-tissue interface and can have different shapes depending on the flow rates and the temperatures of the coolants. Differential cooling can be used to achieve other buried lesion shapes, such as generally elliptical shapes, elongated shapes, or the like.

The $D_{Width\ Max}$ can be selected based on the location of the target region. To damage nerve tissue, the $D_{Width\ Max}$ can be at least about 2 mm to ensure that the lesion includes the nerve tissue. The depth D can be at least about 2 mm to mitigate or avoid a significant amount of damage to smooth muscle tissue. Such embodiments are well suited for treating an airway wall because the smooth muscle tissue is typically not below a depth of 2 mm. In this manner, the cross-sectional width of the target region can be maximized at a depth deeper than the smooth muscle tissue. The majority, and in some embodiments substantially all, of the lesion will be in tissue which is not smooth muscle tissue, typically lying deeper in the airway wall than the region of smooth muscle tissue. Further, any damage to smooth muscle cells in the airway wall can be less than the amount of damage that, in the absence of damaging nerve tissue, would be required to substantially alter the responsiveness or constriction of the airway, e.g. as a result of asthma, COPD, or other pulmonary disease.

The lesion can be separated from the tissue surface by a protected region in which a significant amount of the tissue is not permanently damaged. FIGS. 70B and 71B show a protected region 1561 having a depth $D_P$. Advantageously, because a significant amount of tissue in the protected region 1561 is not permanently damaged, tissue functioning can be preserved. The depth $D_P$ can be at least about 1 mm to about 2 mm to ablate nerve tissue.

It will be understood that the term "lesion" as used herein is intended to mean tissue which is permanently damaged, i.e. to the point of cell death. In some cases, the delivery of energy will cause temporary or non-lethal damage to cells outside the region referred to as the "lesion." For example, epithelial or smooth muscle cells may be temporarily damaged or altered by the energy delivery described herein. However, advantageously, through the use of differential cooling, these cells can recover and remain functional, thus are not considered part of the "lesion" created. By contrast, the catheter 207 can impart permanent damage to nerve tissues lying deep in the airway wall or on the outside of the airway wall, thus attenuating nerve signals that are the cause of certain pulmonary diseases.

The catheter 207 of FIG. 8 can form the lesion 1527 of FIG. 71B. The delivery lumen 324, return lumen 326, and electrode channel 340 (FIG. 13) can each have a diameter of about 2.1 mm. The balloon 212 can be made of a low durometer urethane with a wall thickness of about 0.019 mm to about 0.025 mm and a longitudinal length of about 20 mm. The outer diameter of the balloon 212 is about 16 mm and is inflated to a pressure of about 10 psig. Coolant flows through the electrode 214 at a flow rate of about 100-120 ml/min and is chilled saline or water (e.g., ice cold saline or water). The electrode 214 has a length of about 8 mm and delivers about 25 W of power to the tissue to form the lesion 1527 with a maximal depth $D_{Max}$ of about 7 mm to about 8 mm and the protection region 1561 having a $D_P$ of about 1 mm to about 2 mm. In other words, the lesion 1527 is spaced apart a distance at least 1 mm to about 2 mm from the tissue surface.

Figure 72:
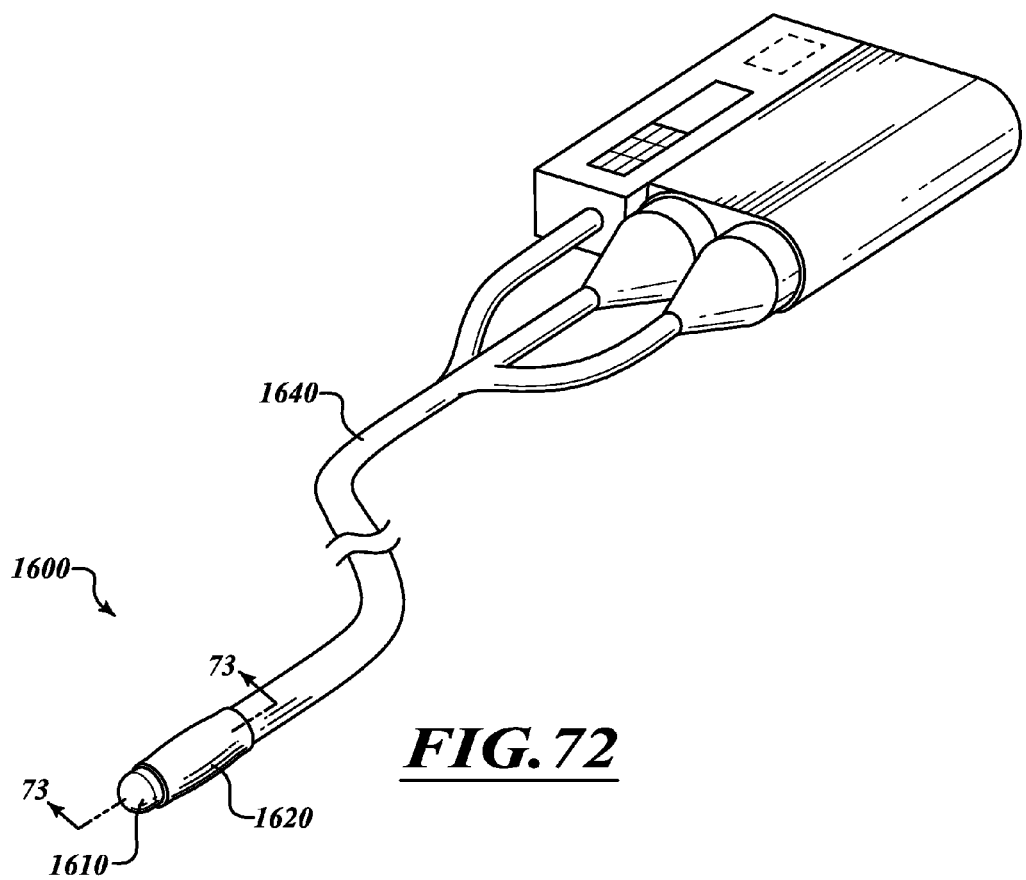
FIG. 72 is an isometric view of a delivery device with a distally distensible, expandable element in a delivery configuration.
Figure 73:
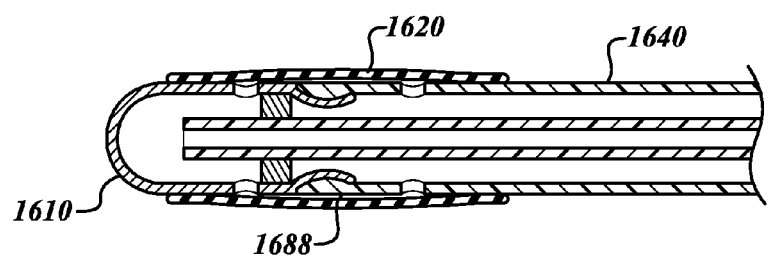
FIG. 73 is a cross-sectional view of an ablation assembly taken along a line 73-73.

FIGS. 72 and 73 show a delivery device 1600 with an electrode 1610 and an expandable element in the form of a balloon 1620. The electrode 1610 extends distally from the deflated balloon 1620, which can closely surround an elongate shaft 1640. A distal section 1688 of the elongate shaft 1640 extends axially through a chamber 1690 and carries the electrode 1610. The balloon 1620 is distensible distally to extend along the electrode 1610 when inflated.

Figure 74:
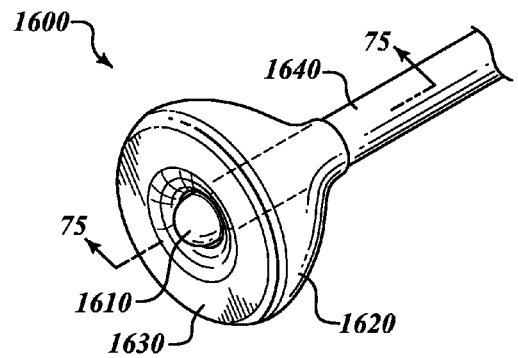
FIG. 74 an isometric view of a delivery device with the distally distensible, expandable element in a deployed configuration.

FIG. 74 shows an inflated generally bell shaped balloon 1620 that defines a distally facing contact surface 1630. The contact surface 1630 surrounds the electrode 1610 and has a generally annular shape. The balloon 1620 can prevent external fluid flow from flowing along the electrode 1610.

Figure 75:
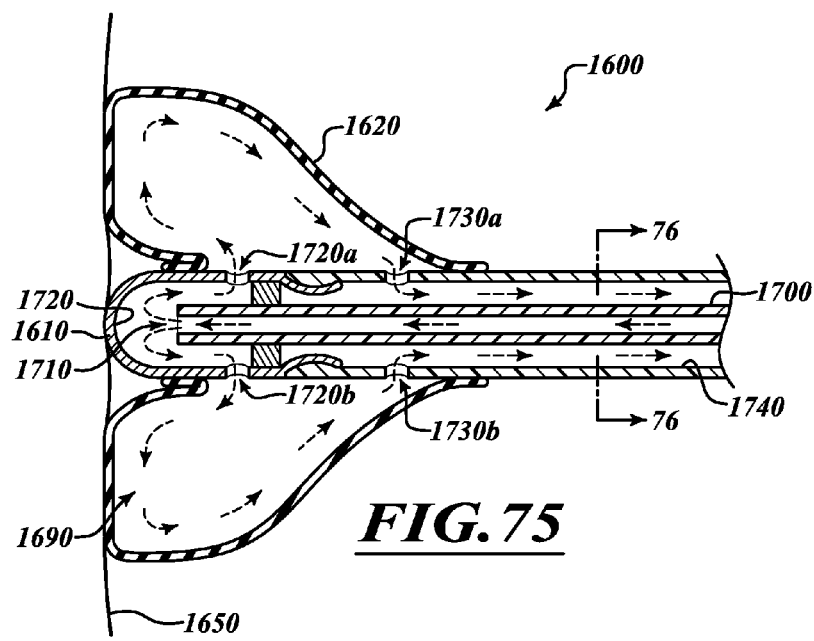
FIG. 75 is a cross-sectional view of an ablation assembly taken along a line 75-75.
Figure 76:
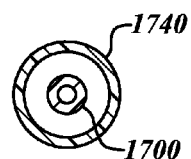
FIG. 76 is a cross-sectional view of an elongate body taken along a line 76-76 of FIG. 75.

FIG. 75 shows coolant flowing along a delivery line 1700. The coolant exits an outlet 1710 and flows along an inner surface 1720 of the electrode 1610. The coolant is heated as it absorbs thermal energy. The coolant exits the electrode 1610 via ports 1720a, 1720b and circulates in a balloon chamber 1690. The coolant absorbs thermal energy to cool tissue. The coolant exits the chamber 1690 via ports 1730a, 1730b and flows through a return line 1740.

If external liquid (e.g., blood, urine, mucous, etc.) flows about the delivery device 1600, the balloon 1620 can block liquid flow along the tissue 1650. The electrode 1610 can deliver energy to the tissue 1650 without an appreciable amount of heat being absorbed by the external fluid flow. For example, if the tissue 1650 is cardiac tissue, the balloon 1620 can prevent a significant amount of blood flow between the balloon 1620 and the tissue 1650, thus preventing tissue near the electrode 1610 from being cooled due to blood flow. Additionally, the balloon 1620 can cool the tissue 1650 to shape lesions, if needed or desired.

FIGS. 77-81 show a delivery device 1800 having an electrode 1810 and a bell-shaped expandable element 1814 coupled to a coaxial shaft 1801. The electrode 1810 is coupled to a distal face of expandable element 1814. An inner lumen 1803 in shaft 1820 delivers cooled inflation fluid to the interior of expandable element 1814 for the expansion thereof. Inflation fluid flows out from expandable element into outer lumen 1850 in shaft 1852. Coolant can flow out of the port 1818 towards a proximal electrode surface 1830 and can circulate through a chamber 1840. Electrode 1810 may be coupled to power wires (not shown), which may extend through the fluid delivery lumen and balloon, to deliver energy to the electrode. Alternatively, a cryogenic fluid may be circulated through the balloon to cool the electrode to cryogenic temperatures to perform cryogenic ablation.

FIGS. 82-86 show a delivery device 1900. A fluid for inflating an expandable element 1910 flows along a delivery lumen 1920 and into a chamber 1930. The fluid exits via a return lumen 1934. Coolant that cools an electrode 1940 flows along delivery lumen 1950 and circulates through an electrode chamber 1954. The coolant exits the chamber 1954 via a return lumen 1960. The electrode coolant and the balloon coolant can be at different temperatures for differential cooling. Advantageously, the flow rates and temperatures of the electrode and balloon coolants can be independently controlled.

The distally ablating delivery devices of FIGS. 72-86 are especially well suited to deliver energy to cardiac tissue. The balloons can be filled with a gas such a carbon dioxide, helium, or air or other fluid with relatively low heat capacity to form endocardial surface lesions, even relatively large endocardial surface lesions. The fluid can be at a temperature that is generally equal to or greater than the normal temperature of the tissue to prevent unwanted cooling. A low temperature coolant can pass through the balloons to protect and cool the tissue near the balloon-tissue interface to limit or eliminate endocardial lesion size and can be used to produce relatively large epicardial lesions.

Figure 87A:
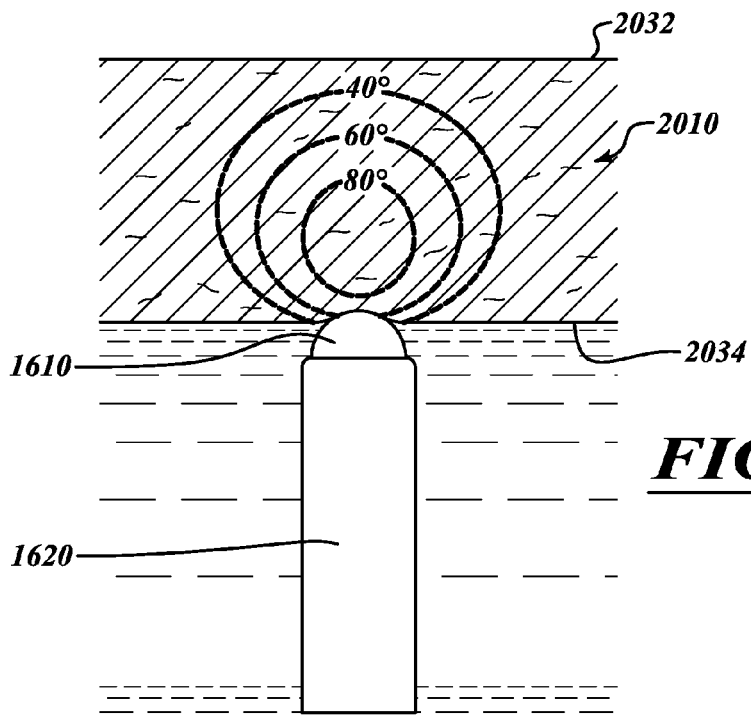
FIGS. 87A-89B show isotherms and corresponding lesions.
Figure 87B:
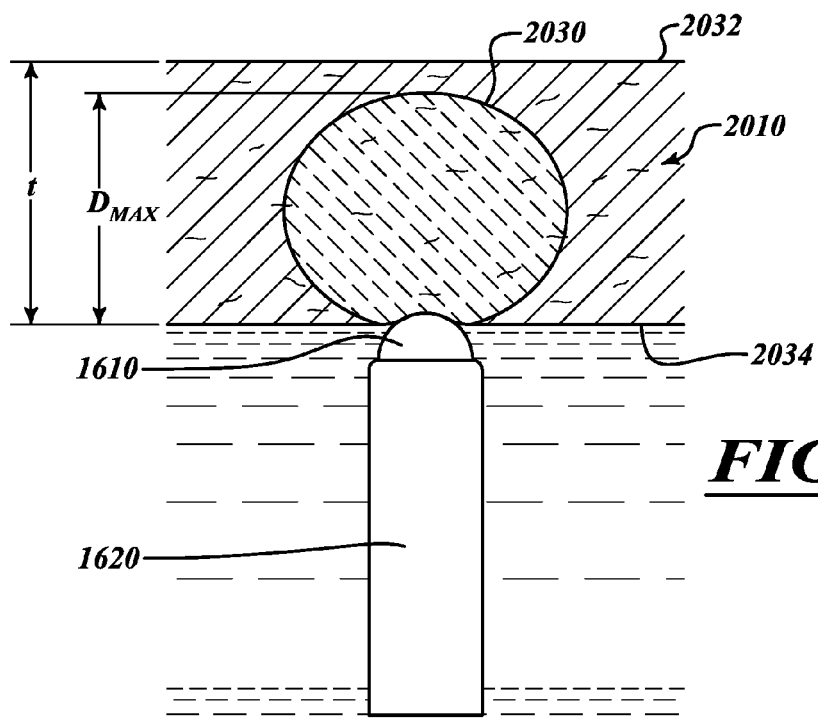

FIGS. 87A-89B show isotherms and corresponding legions. FIG. 87A shows an electrode 1610 delivering energy to tissue 2010. The electrode 1610 can be cooled using a coolant. If the tissue 2010 is cardiac tissue, blood can flow across a tissue surface 2034 and can absorb heat from the tissue 2010 via convection. Accordingly, natural body functioning can help cool the tissue 2010 to form a lesion 2030 with a shape that is similar to the shape of the lesion 1527 in FIG. 68B. The maximal depth $D_{Max}$ of FIG. 87A can be less than the thickness t to avoid damaging the epicardium 2032, but a section of the endocardium 2034 near the electrode 1610 is damaged.

Figure 88A:
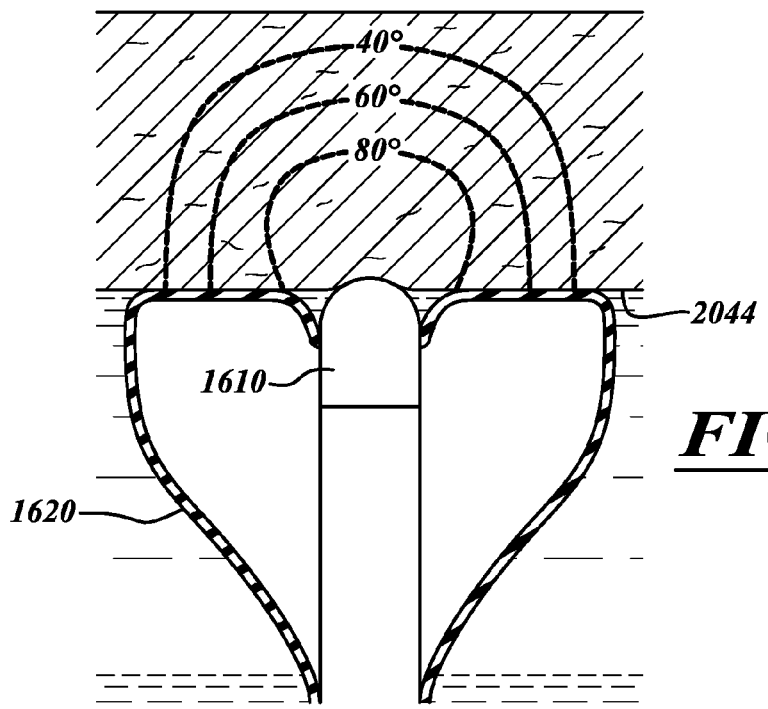
Figure 88B:
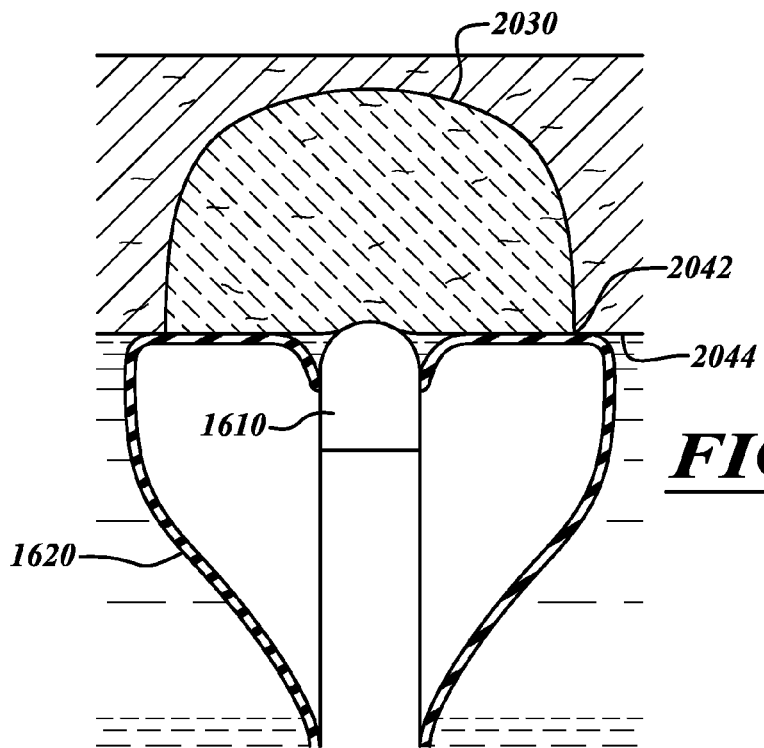

The balloon 1620 can be inflated with a gas (e.g., ambient air) or other fluid that does not absorb a significant amount of thermal energy. The balloon 1620 blocks blood flow and allows ablation of the tissue adjacent to the balloon-tissue interface 2042. As shown in FIG. 88B, the lesion 2030 has a wide base. Thus, the maximum width of the lesion 2030 of FIG. 88B located along the surface 2044.

Figure 89A:
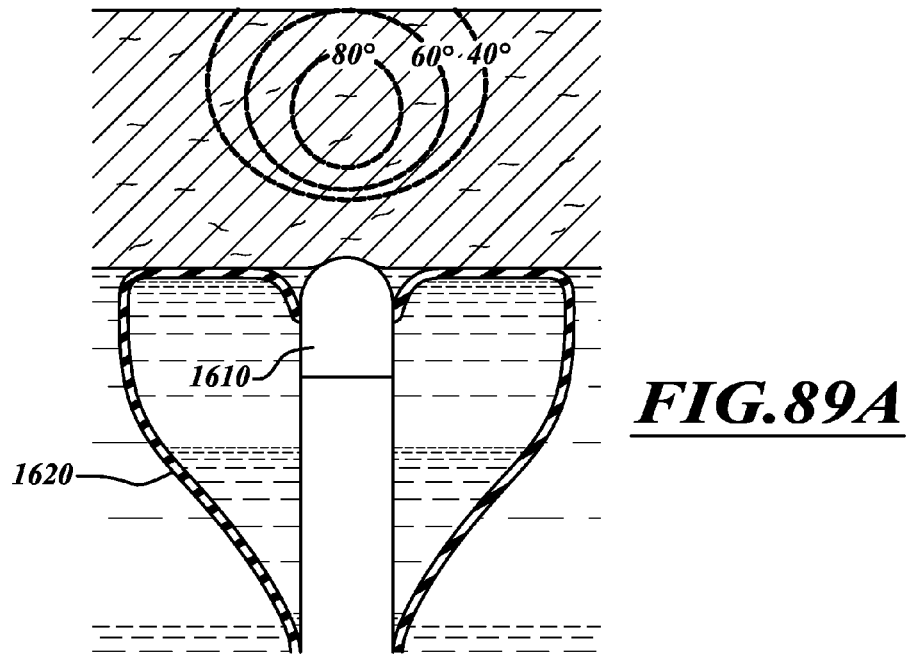
Figure 89B:
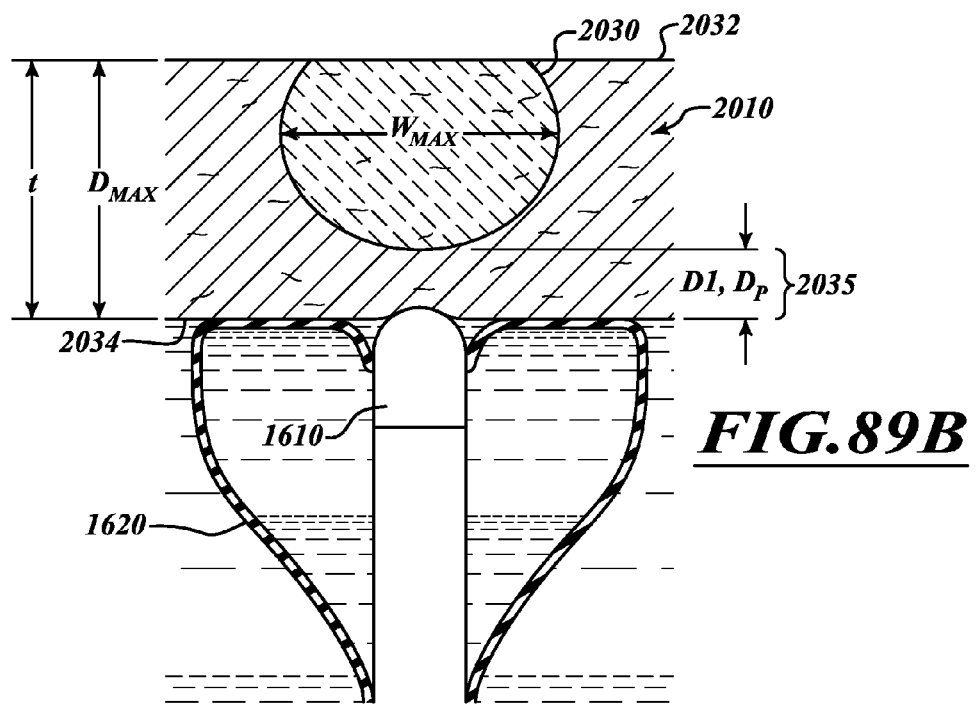

Chilled coolant can be passed through both the electrode 1610 and the balloon 1620 to form lesions spaced apart from the delivery device-tissue interface. FIGS. 89A and 89B show isotherms and a corresponding lesion 2030. A coolant can cool the electrode 1610. A coolant can pass through the balloon 1620 to keep tissue proximate to the balloon 1620 at or below a temperature that induces cell damage or death. The endocardium 2034 can be protected and a significant amount of the epicardium 2032 can be damaged. A protected region 2035 is between the lesion 2030 and the electrode 1610.

Other types of structures can block fluid or blood flow. For example, shields, masks, umbrella structures, or the like can be placed against tissue to prevent the flow of natural bodily fluids along the tissue and, thus, promote shallow lesion formation.

Figure 90:
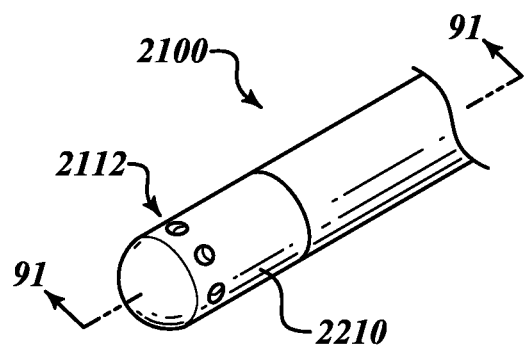
FIG. 90 is an isometric view of a delivery device with discharge ports.
Figure 91:
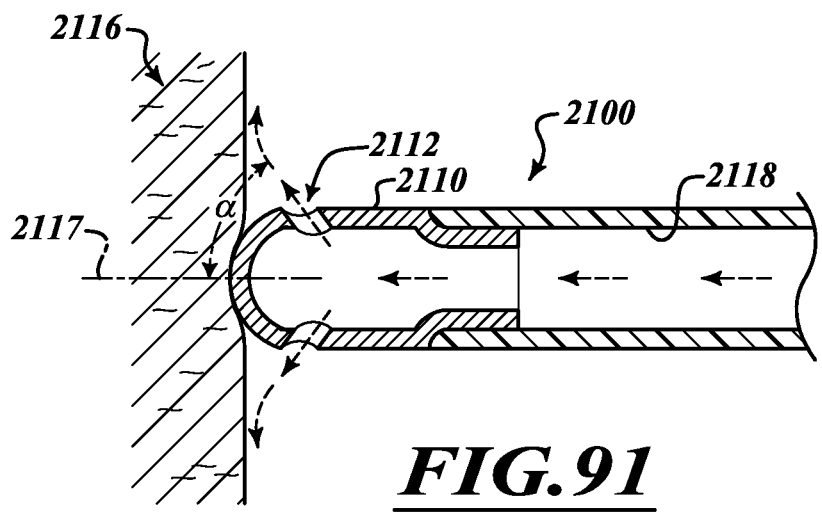
FIG. 91 is a cross-sectional view of the delivery device taken along a line 91-91 of FIG. 90.

FIGS. 90 and 91 show a non-inflatable delivery device 2100 having an electrode 2110 with discharge ports 2112. Advantageously, lesions can be formed without expanding the delivery device 2100. The ports 2112 are circumferentially spaced apart from one another and are configured to spray the coolant towards the tissue 2116. Coolant, represented by arrows, flows out of the ports 2112 and along the tissue 2116. A spray angle α between a longitudinal axis 2117 and the spray can be less than about 90 degrees. In certain embodiments, the spray angle α is less than about 70 degrees to ensure that the coolant absorbs a significant amount of heat via convection.

The coolant can be chilled saline or chilled water, which mixes with bodily fluids (e.g., blood). If the delivery device 2100 is used in organs containing air or other gas, the coolant can be a gas.

Figure 92:
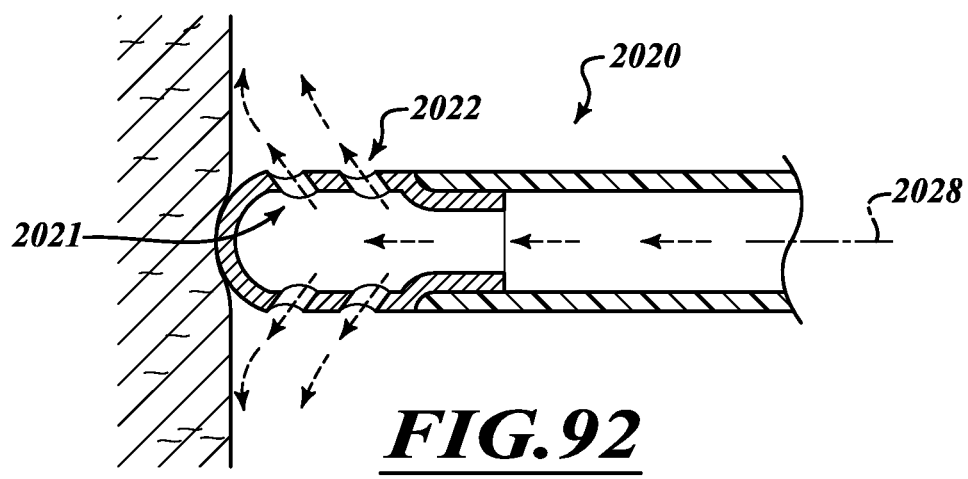
FIG. 92 is a longitudinal cross-sectional view of a delivery device with longitudinally spaced apart discharge ports.

FIG. 92 shows a modified delivery device 2020 that has a first set of circumferentially spaced discharge ports 2021 and a second set of circumferentially spaced discharge ports 2022. The sets of ports 2021, 2022 are axially spaced apart from one another along a longitudinal axis 2028 of the delivery device 2020.

Figure 93:
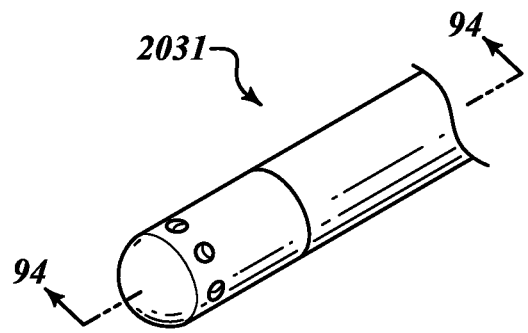
FIG. 93 is an isometric view of a delivery device that performs a throttling process.
Figure 94:
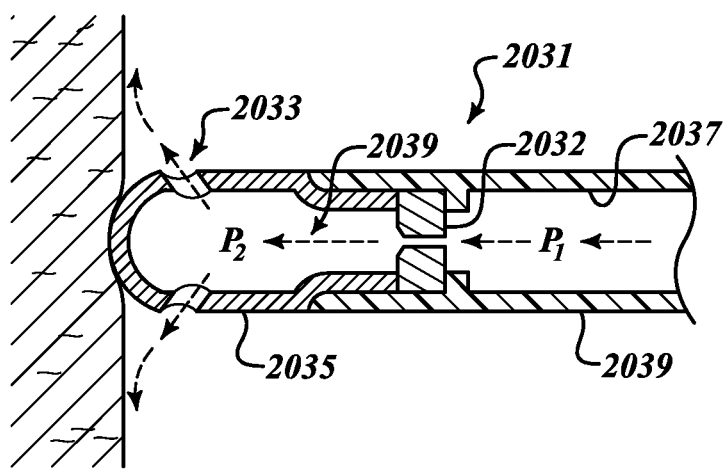
FIG. 94 is a cross-sectional view of the delivery device taken along a line 94-94 of FIG. 93.

FIGS. 93 and 94 show a delivery device 2031 that includes a pressure reducing element 2032 for producing a low temperature fluid. A fluid can flow down a delivery lumen 2037 of an elongate body 2039. The fluid passes through the pressure reducing element 2032 to form a low temperature fluid within the electrode chamber 2039. As used herein, the term "pressure reducing element" refers, without limitation, to a device configured to reduce the pressure of a working fluid. In some embodiments, the pressure reducing element can reduce the pressure of the working fluid to a pressure equal to or less than a vaporization pressure of the working fluid. The working fluid can comprise a refrigerant (e.g., a cryogenic refrigerant or a non-cryogenic refrigerant). In some embodiments, the pressure reducing elements are in the form of pressure reduction or expansion valves that cause vaporization of at least a portion of the working fluid passing therethrough. The pressure reducing element vaporizes an effective amount of the working fluid (e.g., a cryogenic fluid) to reduce the temperature of the working fluid. In some modes, substantially all or most of the working fluid by weight passing through the valve element 2032 is converted to a low temperature and low pressure gas. The low temperature gas flows through the expansion chamber 2039 and exits via the discharge vents 2033. In some embodiments, the pressure reducing element 2032 can be a nozzle valve, a needle valve, a Joule-Thomson throttle, a throttle element, or any other suitable valve for providing a desired pressure drop. For example, a Joule-Thomson throttle can recover work energy from the expansion of the fluid resulting in a lower downstream temperature. In some embodiments, the pressure reducing elements can be substituted with flow regulating elements (e.g., a valve system) especially if the working fluid is a non-refrigerant, such as water.

A high pressure gas $P_1$ of FIG. 94 is passed through the delivery lumen 2037. The high pressure gas $P_1$ passes through the element 2032 and enters the expansion chamber 2039 where the pressure drops to $P_2$. The drop in pressure from $P_1$ to $P_2$ leads to a drop in temperature of the gas from $T_1$ to $T_2$. The magnitude of the temperature change is given by:

$$T_1 - T_2 = \mu(P_1 - P_2)$$

where
T is the temperature of the gas;
P is the pressure of the gas;
μ is the is the Joule-Thomson coefficient of the gas;
Subscript 1 denotes a high pressure condition; and
Subscript 2 denotes a low pressure condition.

A second pressure drop occurs when the gas in the expansion chamber 2039 exits through the ports 2033 and drops to a surround pressure. If the delivery device 2031 is used in the lung, the surrounding pressure is atmospheric pressure. This temperature drop is:

$$T_2 - T_3 = \mu(P_2 - P_{ATM})$$

Thus, the cold gas flowing into the expansion chamber 2039 through the valve element 2032 will cool the electrode 2035 and the cold gas flowing from the expansion chamber 2039 through the ports 2033 can be directed at the surrounding airway and will cool the surrounding tissue.

The Joule-Thomson coefficient (μ) is specific for each gas or combination of gasses. Standard temperature values for μ are:

Carbon dioxide $$\mu_{CO_2} = 1.16 \times 10^{-5} \frac{K}{Pa}$$

Air $$\mu_{air} = 0.23 \times 10^{-5} \frac{K}{Pa}.$$

These coefficients indicate that for a given pressure drop, $CO_2$ will cause a 5 times greater drop in temperature than a similar drop in pressure experienced by air.

The use of air in the lungs can be desirable. Carbon dioxide can be used if the flow rates of coolant gas are sufficiently low so as to not overwhelm the patient's ability to ventilate this additional carbon dioxide out of the lungs. The cooling effect can be enhanced if the coolant in the coolant conduit is a high pressure liquid, such as liquid air or liquid $CO_2$. The high pressure liquid passes through the pressure reducing element 2032 (e.g., a throttle) and undergoes an endothermal phase change from a high pressure liquid to a high pressure gas, which causes the temperature of the gas to be lower than that of the high pressure liquid. It then goes through a Joule-Thomson expansion from $P_1$ to $P_2$ which causes a further drop in temperature, before being vented out of the electrode via the vents 2033.

It will be understood that in any of the embodiments of energy emitter assemblies disclosed herein, the electrodes and/or the tissue adjacent to the electrodes may be cooled by fluids undergoing Joule-Thomson expansion as described above. For example, a pressurized fluid may be passed through a pressure reducing element in any of these energy emitting assemblies such that the fluid undergoes a phase change to gas, which may be vented directly toward the electrodes to be cooled, and/or toward the airway wall tissues adjacent to the area of contact by the electrodes.

Figure 95:
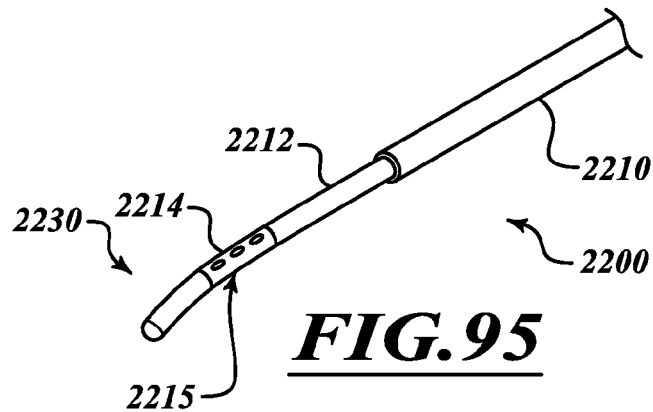
FIG. 95 is an isometric view of a delivery device in a delivery configuration.
Figure 96:
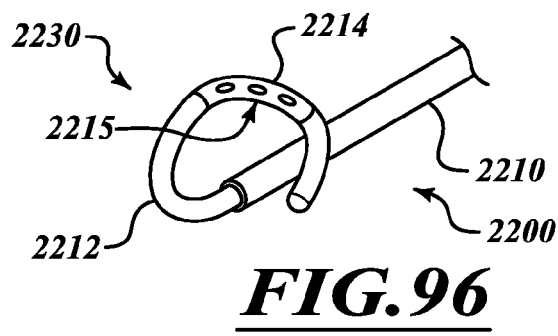
FIG. 96 is an isometric view of the delivery device in a deployed configuration.
Figure 97:
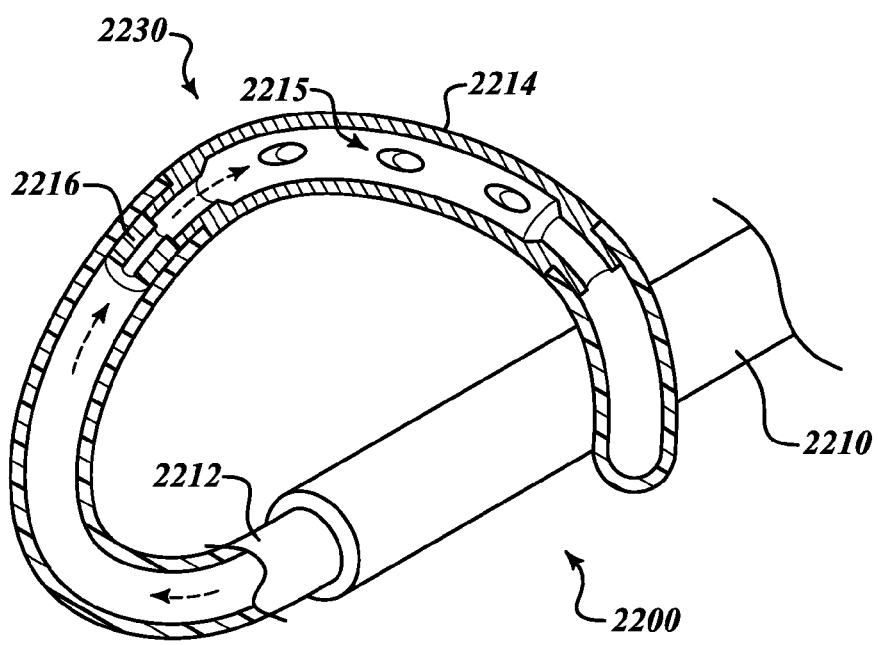
FIG. 97 is a detailed cross-sectional view of a distal section of the delivery device.

FIGS. 95-97 show an actuatable catheter 2200 movable from a delivery configuration of FIG. 95 to a tissue treatment configuration of FIG. 96. The actuatable catheter 2200 includes a sleeve 2210 and an elongate body 2212. The elongate body 2212 includes an electrode 2214 with ports, illustrated as three vents 2215. A coolant, which may be a low temperature liquid such as chilled saline or water, can be discharged via the vents 2215. A valve element 2216 (e.g., a Joule-Thomson element) can reduce the temperature of the working fluid.

The deployed section 2230 can have an arcuate shape for conforming to the inner surface of an airway or other vessel. The arcuate deployed section 2230 can have an axis of curvature which is generally coplanar with a longitudinal axis of the elongate body 2212. A biasing element such as a wire or push rod extending through elongate body 2212 can adjust the configuration of the delivery device 2200. If the biasing element is a wire, the wire can be pulled to move the deployed section 2230 into the arcuate shape. Alternatively, a sleeve 2210 can be slid distally over the distal section 1230 to cover the deployed section 2230 and constrain it in a straightened configuration during delivery. When the sleeve is removed the deployed section 2230 will resiliently return to the arcuate shape. In other embodiments, when a coolant is delivered through the distal section 2230, the pressure of the coolant can cause the distal section 2230 to assume the curved shape (e.g., a spiral configuration, a coiled configuration, or a helical configuration).

Figure 98:
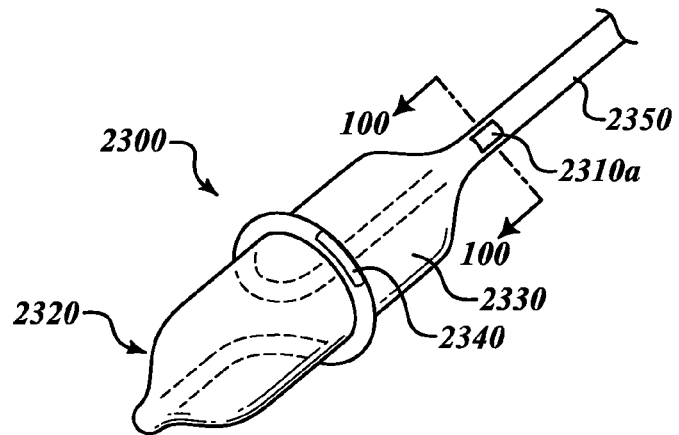
FIG. 98 is an isometric view of a delivery device with positioning features.
Figure 99:
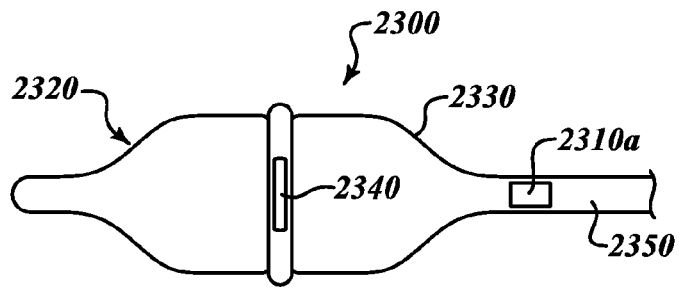
FIG. 99 is a top plan view of the delivery device of FIG. 98.
Figure 100:
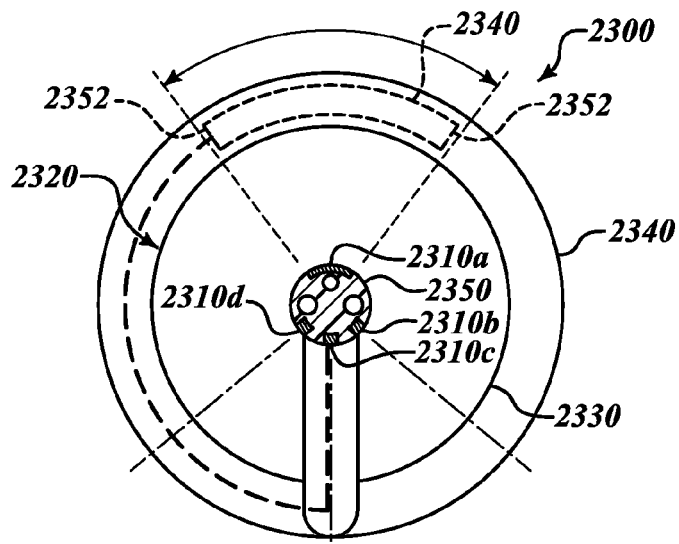
FIG. 100 is a cross-sectional view of the delivery device taken along a line 100-100.

FIG. 98 shows a delivery device 2300 with a visual indicator 2310*a* disposed on shaft 2350. When an assembly 2320 is inflated in an airway, it may be difficult to see an electrode 2340, especially if the electrode 2340 is between cartilaginous rings or if mucous is collected around the exterior of the balloon 2330. Thus, it may be difficult for a physician to accurately position the electrode 2340. The visual indicator 2310*a* is located proximally of the expandable element 2330 and, thus, is viewable from a proximal position relative to the expandable element. The visual indicator 2310*a* corresponds to the position of the electrode 2340. In some embodiments, including the illustrated embodiment, the electrode 2340 is positioned generally radially outward and axially offset of the visual indicator 2310*a*, as shown in FIG. 100. The electrode 2340 of FIG. 100 has an arc length that is generally equal to an arc length of the visual indicator 2310*a*. Based on the location of the visual indicator 2310*a*, the physician can determine the approximate location of the electrode ends 2352, 2354. This makes it easier for the physician to rotate and accurately position the electrode 2340.

The visual indicator or marking 2310*a* can be colored, reflective, or otherwise readily visible through a bronchoscope. In some embodiments, the visual indicator 2310*a* can be a longitudinally-extending stripe or mark. In other embodiments, the visual indicator 2310*a* can be one or more light sources. If the ablation assembly 2320 includes a plurality of electrodes, different visual indicators can correspond to the positions of different electrodes. Visual indicators can be located on the elongate shaft 2350, the balloon 2330, electrode 2340, or other suitable location.

FIG. 100 shows visual indicators positioned about the elongate shaft 2350. Each of the visual indicators 2310*a*, 2310*b*, 2310*c*, 2310*d* (collectively "2310") can be a different color. The user can position the ablation assembly 2320 using the visual indicators 2310. In other embodiments, the proximal end of the balloon 2330 has visual indicators.

Figure 101:
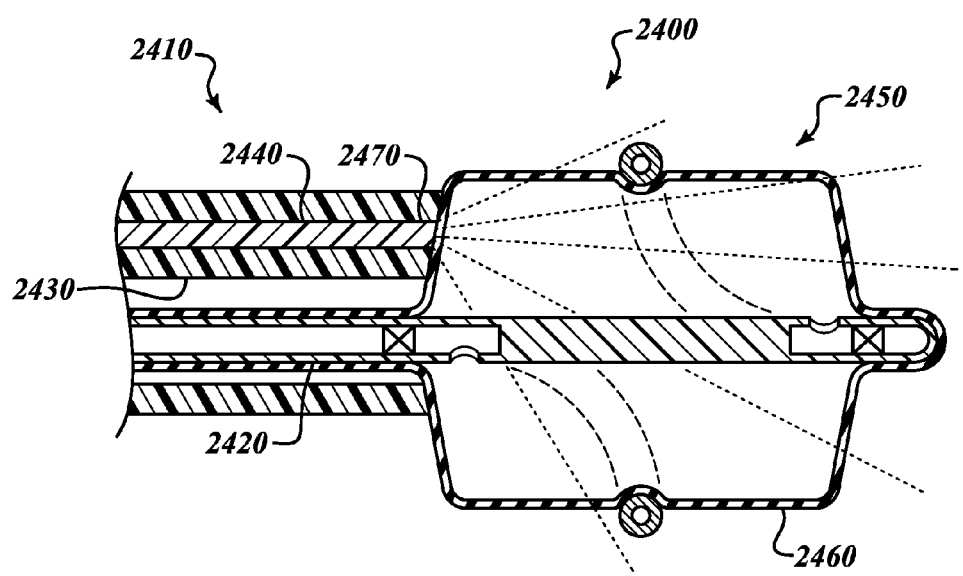
FIG. 101 is a longitudinal cross-sectional view of a delivery apparatus and a delivery device.

FIG. 101 shows a catheter 2400 positioned in a delivery apparatus 2410. An elongate body 2420 extends through a working lumen 2430. An optical element 2440 can be used to view and position the ablation assembly 2450. A balloon 2460 can be transparent or semi-transparent.

The delivery apparatus 2410 is a bronchoscope with camera optics 2440. A distal end 2470 of the camera optics 2440 is optically coupled to the balloon wall. The distal end 2470 can be pressed against the conformable balloon's proximal surface to provide optical coupling. During use, the user may view the electrode or other components or anatomical features through the wall of the balloon and the fluid within the balloon.

In other embodiments, the delivery apparatus 2410 can be a sheath with fiber optics 2440 having lenses, light sources, cameras, or the like. In certain embodiments, the optical element 2440 is integrated or coupled to the balloon 2460. This prevents mucous or other unwanted substances from obscuring the user's view. The balloon geometry, specifically the angle of the proximal balloon wall, may be selected to optimize optical coupling with the camera optics 2440. The proximal balloon wall can have a section which can be aligned with the camera optics 2440 and which is substantially flat, smooth, transparent, and which is parallel to the plane of the distal end 2470 of the camera optics 2440, preferably in some embodiments being disposed at an angle of about 75 degrees to about 105 degrees relative to the longitudinal axis of the elongate body 2420. The material of the proximal balloon wall may be selected to optimize visibility and transparency, e.g. with a refractive index which is compatible with the camera optics 2440 and/or fluid within the balloon.

Figure 102:
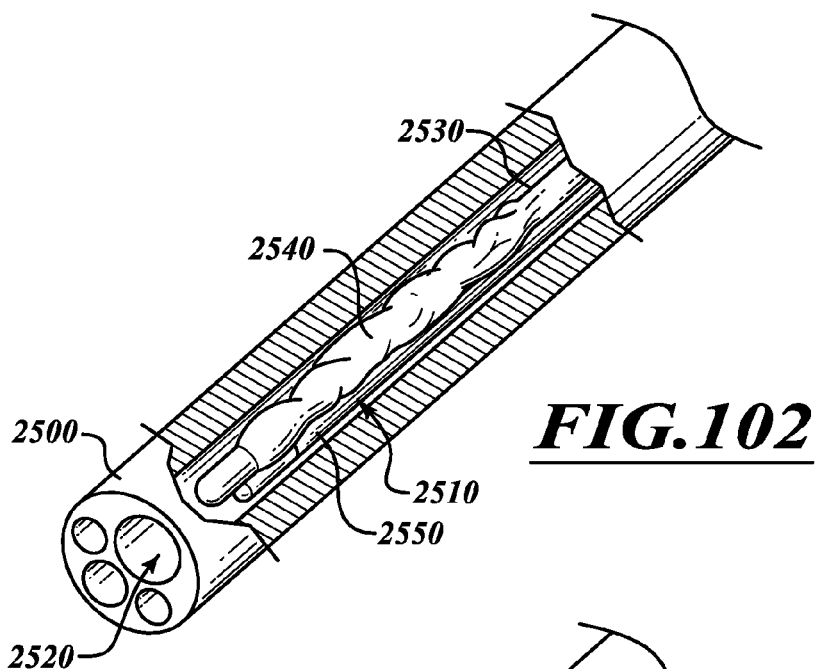
FIG. 102 is an isometric, cutaway view of a delivery apparatus holding a delivery device.
Figure 103:
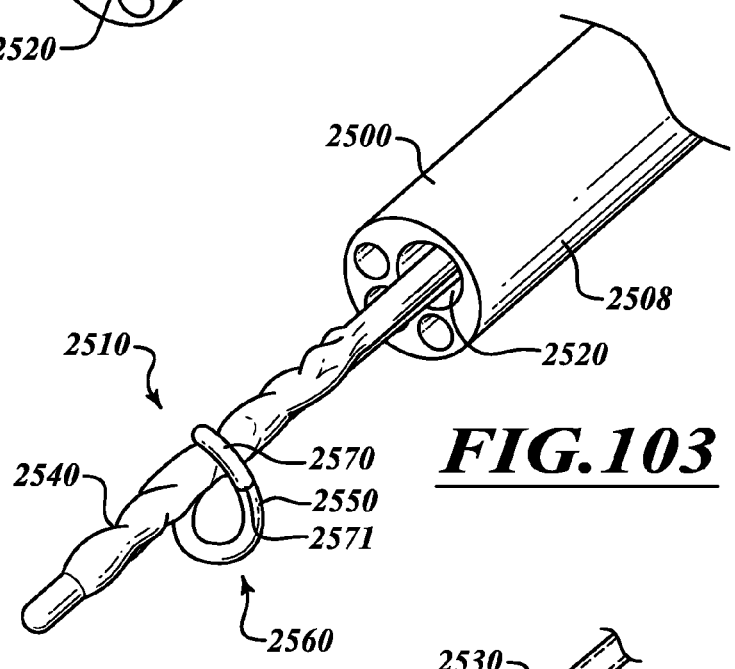
FIG. 103 is an isometric view of the delivery device ready to be deployed.

FIG. 102 shows an ablation assembly 2510 including an elongate shaft 2530, a balloon 2540, and a displaceable energy emitter assembly 2550. The ablation assembly 2510, in a generally straight configuration, can be moved out of a delivery apparatus 2500 to assume a curved configuration, illustrated with an arc length of about 180 degrees. An energy emitter assembly 2550 can be biased to assume the preset spiral or curved shape. When it passes out of the working lumen 2520, it can assume the delivery configuration. Alternatively, the energy emitter assembly 2550 through which coolant can be delivered can be formed of a shape memory material.

Figure 104:
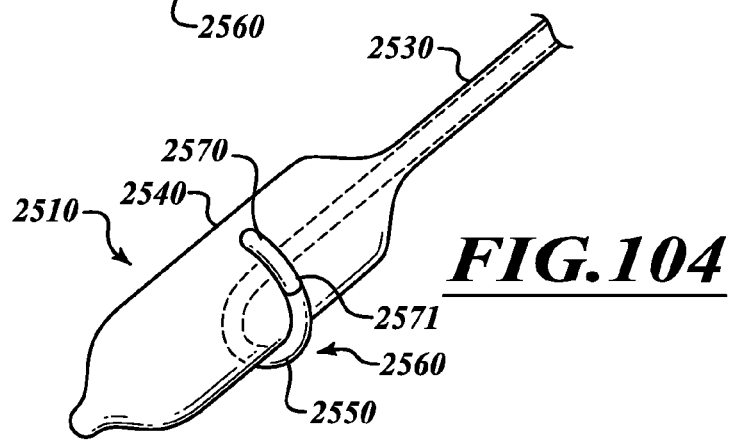
FIG. 104 is an isometric view of the delivery device of FIG. 103 in a deployed configuration.

As shown in FIG. 104, the balloon 2540 extends distally past a tip 2570. The inflated balloon 2540 is received by a curved section 2560 of the energy emitter assembly 2510 such that an electrode 2571 is positioned along the outside of the balloon 2540. The electrode 2571 can be cooled by the balloon 2540. Additionally or alternatively, the energy emitter assembly 2550 can have a cooling channel through which a coolant flows. In some embodiments, the energy emitter 2550 can be similar to the embodiments shown in FIGS. 54-57 that provide counter flows. In yet other embodiments, ports, vents, or other features can be incorporated into the energy emitter assembly 2550 to provide direct cooling of the tissue.

Figure 105:
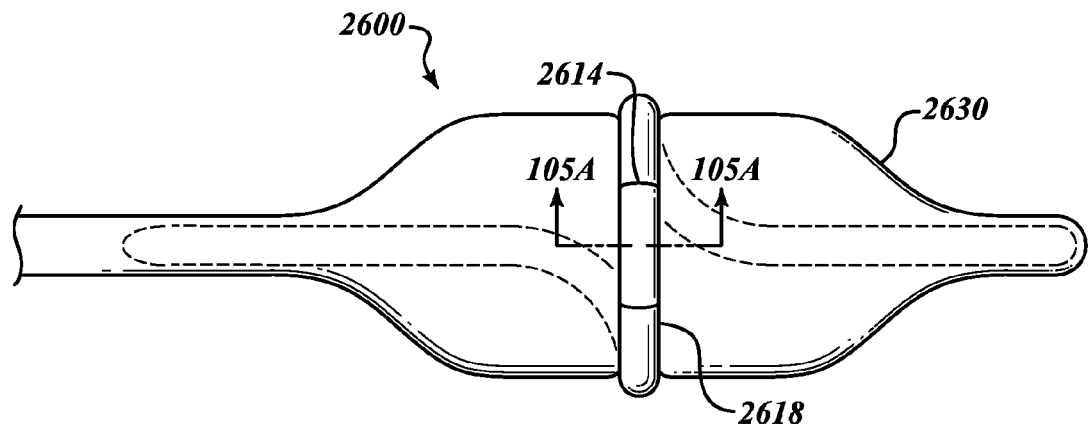
FIG. 105 is a side elevational view of an ablation assembly in a deployed configuration.
Figure 105A:
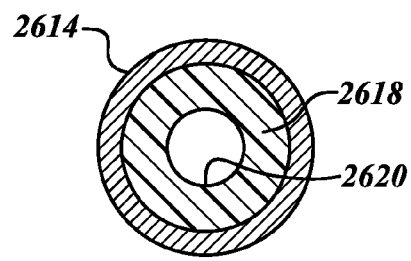
FIG. 105A is a cross-sectional view of an electrode taken along a line 105A-105A of FIG. 105.

FIGS. 105 and 105A show an ablation assembly 2600 that includes a collapsible electrode 2614 carried on a conduit or tubular member 2618. The electrode 2614 can be a coating, thin foil, film, or other electrically conductive material. Different types of coating, plating, or other fabrication techniques can be used to form the electrode 2614. In other embodiments, the electrode 2614 can be coupled to an interior surface 2620 of the tubular member 2618. This prevents direct electrode contact with tissue or bodily fluids.

Figure 106:
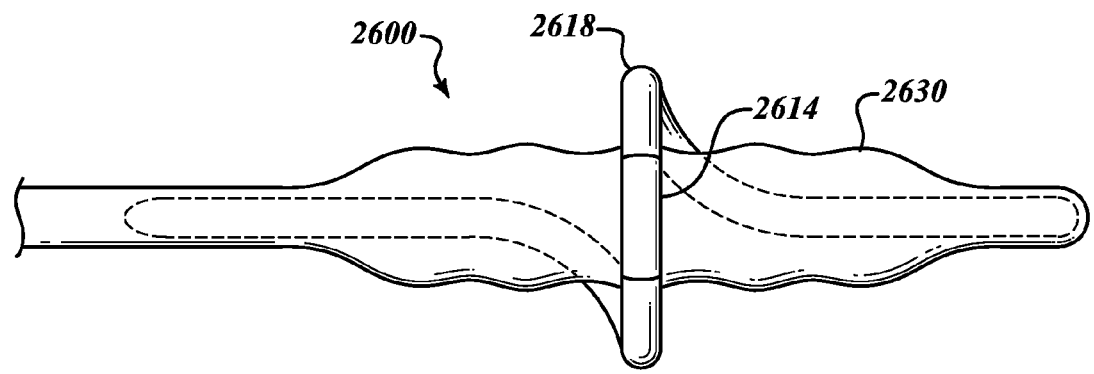
FIG. 106 is a side elevational view of an ablation assembly with an expandable element in a partially inflated state and an inflated energy emitter assembly.
Figure 107:
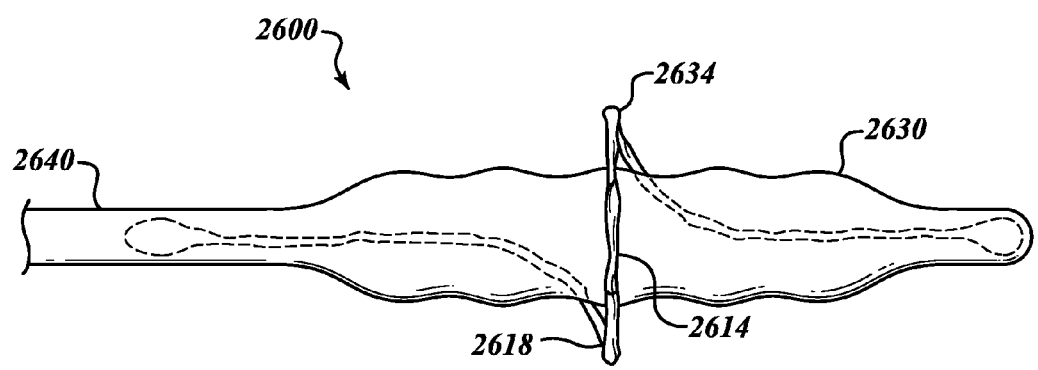
FIG. 107 is a side elevational view of the ablation assembly with a deflated energy emitter assembly.
Figure 108:
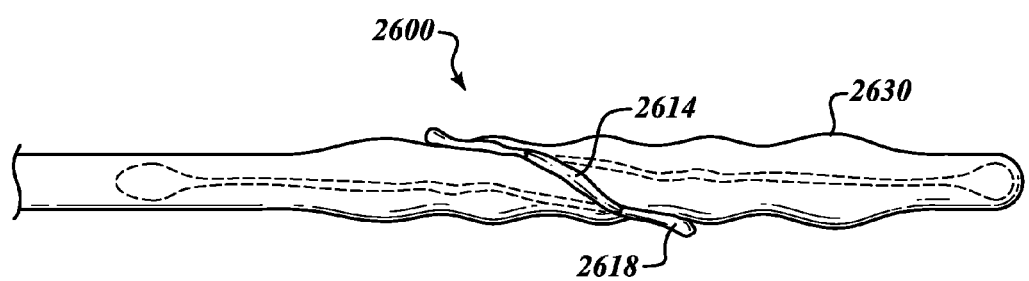
FIG. 108 is a side elevational view of the ablation assembly with the deflated energy emitter assembly in a collapsed configuration.

FIGS. 106-108 show the collapsing process. FIG. 106 shows a balloon 2630 in a partially collapsed configuration. The conduit 2618 holds the electrode 2614 in a deployed configuration.

FIG. 107 shows the balloon 2630 in a fully collapsed configuration and the energy emitter assembly 2634 in a collapsed configuration. The radially collapsed electrode 2614 assumes a relatively small profile. To facilitate the collapsing process, a vacuum can be drawn. As shown in FIG. 108, the electrode 2614 can lay against the elongate body 2640 and the balloon 2630 to assume a relatively low-profile position.

To inflate the ablation assembly 2600, a fluid can flow through and inflate the conduit 2618. An internal throttle valve can control the relative pressure between the conduit 2618 and the balloon 2630. FIG. 106 shows the partially inflated balloon 2630. The fluid continues to fill the balloon 2630 until the balloon 2630 is fully deployed. Thus, the conduit 2618 can be fully inflated before completing inflation of the balloon 2630. Other types of inflation processes can also be used.

Figure 109:
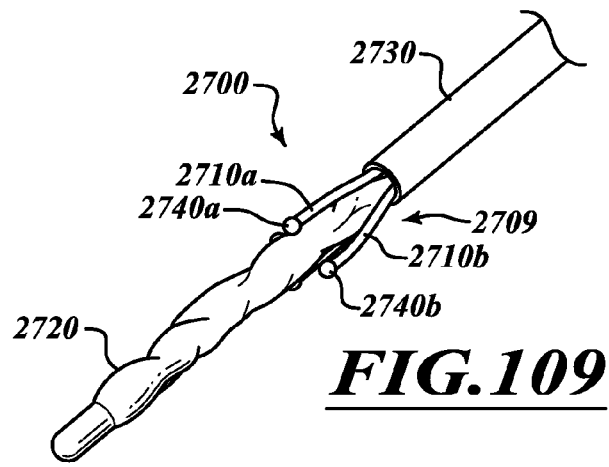
FIG. 109 is an isometric view of a delivery device with an independently deployable electrode assembly and expandable element.
Figure 110:
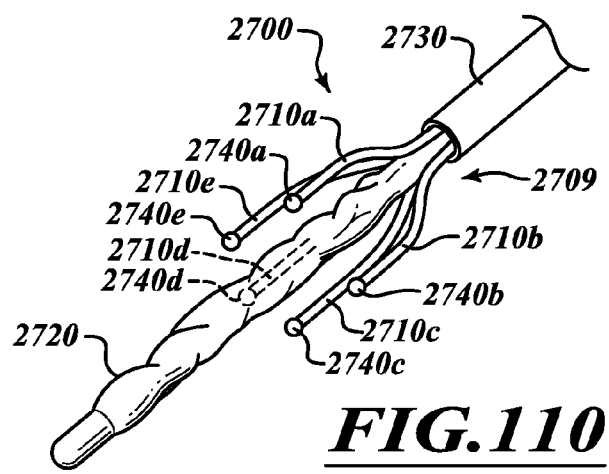
FIG. 110 is an isometric view of the delivery device with the expandable element in a deployed state.
Figure 111:
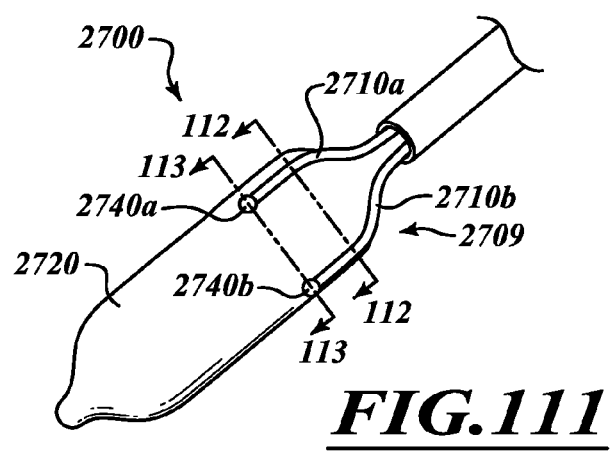
FIG. 111 is an isometric view of the electrode assembly and the expandable element in delivery states.

FIG. 109 shows an ablation assembly 2700 that includes an expandable basket 2709 with displaceable electrode arms 2710a, 2710b, 2710c, 2710d, 2710e (collectively "2710"). The electrode arms 2710 are circumferentially spaced about an expandable element 2720, illustrated as an inflatable balloon. The arms 2710 extend distally from an elongate shaft 2730. Each arm 2710 carries an electrode element 2740a, 2740b, 2740c, 2740d, 2740e (collectively "2740"). The arms 2710, which may be a conductive shape memory material such as Nitinol, are resiliently biased outwardly such that when extended distally from elongate shaft 2730 they return to a radially expanded configuration as shown in FIG. 110. Expandable element 2720 may be expanded to urge the arms 2710 against the airway wall. Further a coolant may be circulated through expandable element 2720 to cool electrodes 2740a-e and the tissue adjacent thereto.

Figure 112:
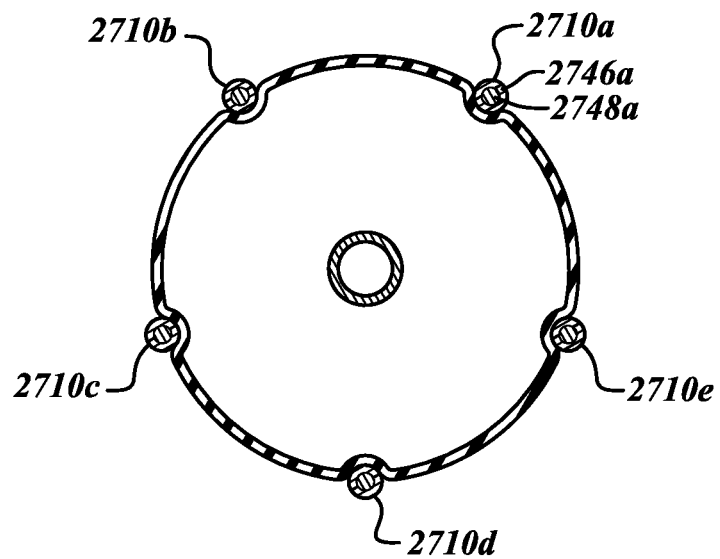
FIG. 112 is a cross-sectional view of the delivery device taken along a line 112-112 of FIG. 111.

FIG. 112 shows the elongate arm 2710a with an insulator 2746a surrounding an electrical conductor 2748a. The electrical conductor 2748a provides electrical communication between the electrode 2740a and the elongate shaft 2730. The electrical conductor may be a conductive metallic material used to form the arms 2710 themselves, such as Nitinol.

Figure 113:
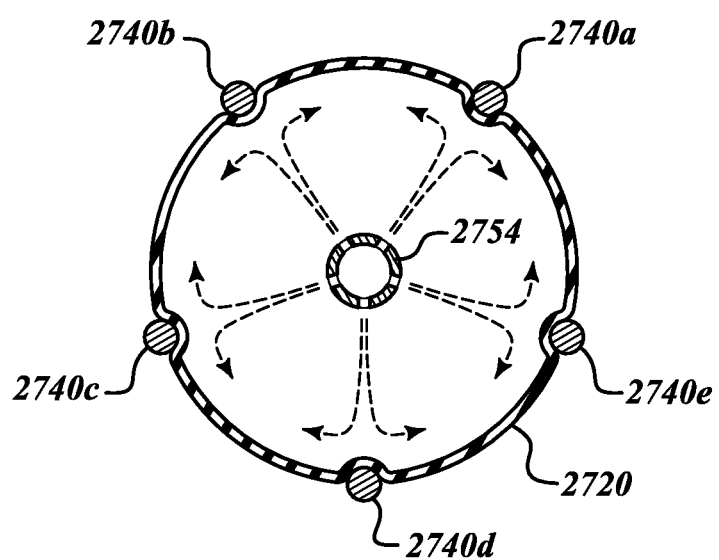
FIG. 113 is a cross-sectional view of the delivery device taken along a line 113-113 of FIG. 111.

FIG. 113 shows the electrodes 2740a-e circumferentially spaced apart about the periphery of the expandable element 2720. The illustrated embodiment includes five electrodes. A higher or lower number of electrodes can be used based on the number of treatment sites. In other embodiments, a plurality of spaced apart electrodes can be positioned along each of the elongate arms. The electrodes can be activated sequentially or concurrently. In some embodiments, the electrodes can be operated in monopolar mode at the same time. Alternatively, the various pairs of plurality of electrodes can be operated in a bipolar mode. A wide range of different modes of operation can be used.

A delivery conduit 2754 of FIG. 113 delivers a coolant, represented by arrows, radially outward towards each electrode 2740. The coolant can circulate in the balloon 2720.

Figure 114:
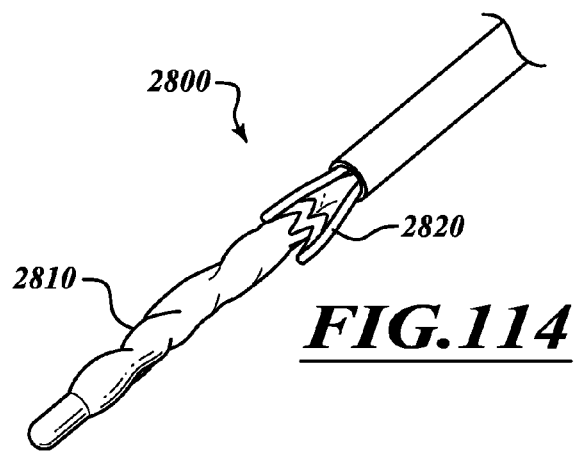
FIG. 114 is an isometric view of a delivery device with a circumferentially expandable electrode.
Figure 115:
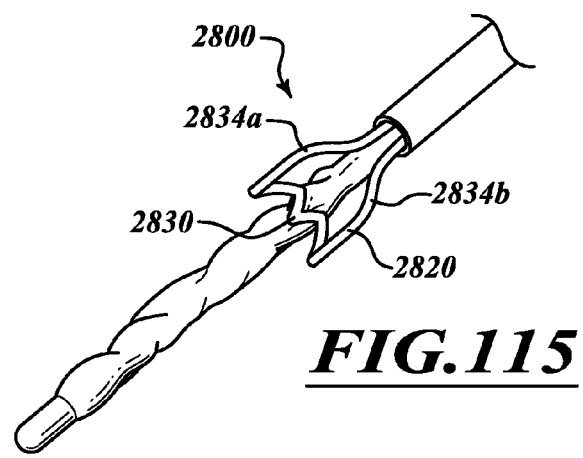
FIG. 115 is an isometric view of the electrode of FIG. 114 in an expanded state.
Figure 116:
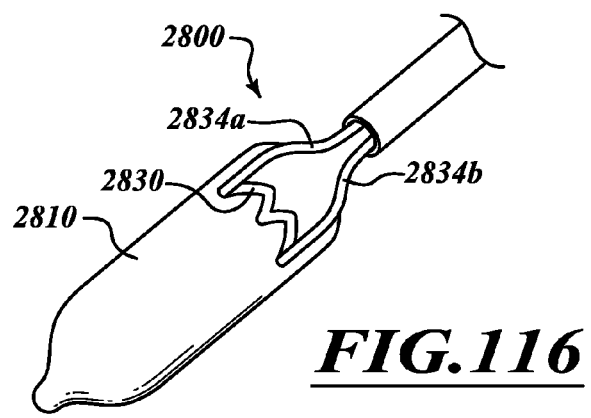
FIG. 116 is an isometric view of an expanded element holding the electrode in the expanded state.

FIGS. 114-116 show an ablation assembly 2800 including an expandable element 2810 and a deployable energy emitter assembly 2820. The energy emitter assembly 2820 can be expanded to deploy a zig-zag or wave-shaped electrode 2830. The deployed electrode 2830 extends between ends of a pair of arms 2834a, 2834b. The illustrated electrode 2830 has a zigzag configuration, but other configurations are also possible.

To position the electrode 2830 near tissue, the expandable element 2810 can be inflated to move the arms 2834a, 2834b outwardly. In some embodiments, the arms 2834a, 2834b are self-expanding. As the ablation assembly 2800 moves out of a working lumen of a delivery assembly, the arms 2834a, 2834b can assume an expanded configuration. In other embodiments, the arm 2834a, 2834b are made of a shape memory material and can be activated to assume the expanded configuration. The arms themselves may be made of a conductive material such as Nitinol to conduct energy to the electrode 2830.

Figure 117:
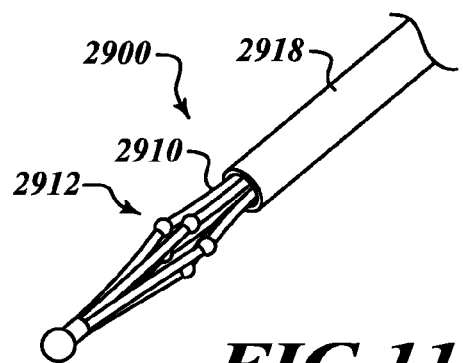
FIG. 117 is an isometric view of a delivery device in accordance with another embodiment.

FIG. 117 shows a delivery device 2090 that includes a deployable basket 2910. The deployable basket 2910 has an elongate shape and includes a plurality of elongated arms or struts carrying electrodes 2912. In other embodiments, the basket 2910 can be generally spherical, ovoid, or can have any other suitable configuration. Advantageously, air can pass through the basket 2910 to maintain ventilation. The plurality of struts can include passageways through which coolant flows, one or more valves (e.g., throttles, Joule-Thomson throttles, or the like). In some embodiments, cryogenic fluids or refrigerant(s) can be delivered through the struts (illustrated with five struts) for enhanced cooling. The embodiments shown in FIGS. 54 and 57 can be incorporated into the struts. In some embodiments, the elements 2912 can be in the form of energy emitting assemblies comprising electrodes and internal throttle valves.

Figure 118:
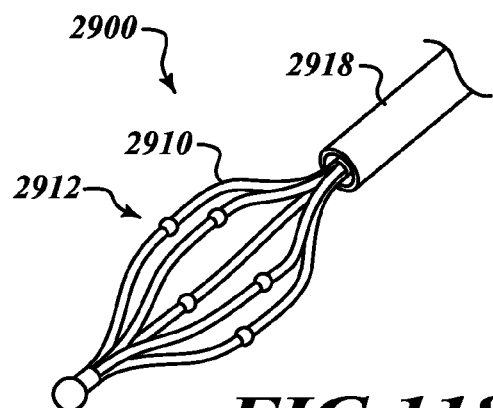
FIG. 118 is an isometric view of the delivery device in an expanded state.
Figure 119:
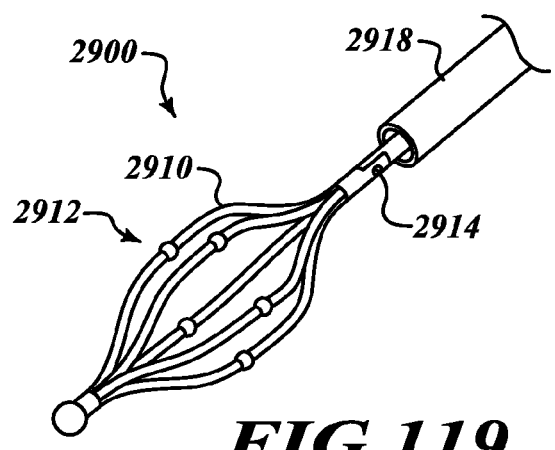
FIG. 119 is an isometric view of the delivery device in an expanded state.

FIG. 118 shows the basket 2910 in a partially expanded configuration. The electrodes 2912 are moved radially outward as the basket expands. FIG. 119 shows the basket 29 under the fully expanded configuration. A pivot or joint 2914 of FIG. 119 can provide rotation of the basket 2910 with respect to an elongate shaft 2918. This allows for flexibility when placing the basket 2910 along highly curved lumens. The pivot 2914 can be formed by an articulating joint, a flexible member, a hinge, or other suitable feature for providing relatively large amount of rotation.

The delivery devices disclosed herein can treat the digestive system, nervous system, vascular system, or other systems. For example, the elongate assemblies, intra-luminal catheters, and delivery devices disclosed herein can be delivered through blood vessels to treat the vascular system. The treatment systems and its components disclosed herein can used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue. Access techniques and procedures used to provide access to a target region can be performed by a surgeon and/or a robotic system. Those skilled in the art recognize that there are many different ways that a target region can be accessed.

The delivery devices disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, as discussed above.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The embodiments and techniques disclosed herein can be used with other procedures, such as bronchial thermoplasty.

Unless the context requires otherwise, throughout the specification and claims which follow, the word "comprise" and variations thereof, such as "comprises" and "comprising" are to be construed in an open, inclusive sense, that is, as "including but not limited to."

The various embodiments described above can be combined to provide further embodiments. These and other changes can be made to the embodiments in light of the above-detailed description. The embodiments, features, systems, devices, materials, methods and techniques described herein may, in some embodiments, be similar to any one or more of the embodiments, features, systems, devices, materials, methods and techniques described in of application Ser. No. 12/463,304 filed on May 8, 2009; U.S. Provisional Patent Application No. 61/255,367 filed Oct. 27, 2009; and U.S. Provisional Patent Application No. 61/260,348 filed Nov. 11, 2009. Each of these applications is incorporated herein by reference in its entirety. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent application Ser. No. 12/463,304. For example, the apparatuses of disclosed in U.S. patent application Ser. No. 12/463, 304 may incorporate the electrodes or other features disclosed herein.

In addition, the embodiments, features, systems, delivery devices, materials, methods and techniques described herein may, in certain embodiments, be applied to or used in connection with any one or more of the embodiments, features, systems, devices, materials, methods and techniques disclosed in the above-mentioned of application Ser. No. 12/463, 304 filed on May 8, 2009; U.S. Provisional Patent Application No. 61/255,367 filed Oct. 27, 2009; and U.S. Provisional Patent Application No. 61/260,348 filed Nov. 11, 2009.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An energy delivery device, comprising:
an elongate shaft through which a coolant is capable of flowing and having a longitudinal axis; and
an ablation assembly coupled to the elongate shaft, the ablation assembly including
an expandable member, and
an energy emitter assembly including a fluid delivery conduit, and at least one ablation electrode that extends along the fluid delivery conduit, wherein the fluid delivery conduit and the at least one ablation electrode are at least partially movable relative to an underlying surface of the expandable member between a first orientation and a second orientation, wherein a first dimension of the ablation electrode is at a smaller angle relative to the longitudinal axis in the first orientation than in the second orientation, and the ablation electrode is arranged to extend circumferentially around the expandable member and fit at least partially within a space between adjacent cartilage rings of an airway of a patient in the second orientation.

2. The energy delivery device of claim 1, wherein the expandable member is configured to cause the energy emitter assembly to move from a low-profile configuration to a deployed configuration as the expandable member expands.

3. The energy delivery device of claim 1, wherein the elongate shaft includes a first delivery lumen in fluid communication with a the fluid delivery conduit and a second delivery lumen in fluid communication with a chamber of the expandable member, the fluid delivery conduit being fluidly connected to the chamber to allow the coolant to flow serially through the energy emitter assembly and the expandable member.

4. The energy delivery device of claim 1, wherein a portion of the energy emitter assembly is moveable with respect to the expandable member to allow the expandable member to urge the ablation electrode of the energy emitter assembly between adjacent cartilage rings of the airway as the expandable member expands.

5. The energy delivery device of claim 1, wherein the at least one ablation electrode is movable relative to a portion of the expandable member that directly underlies the at least one ablation electrode when the at least one ablation electrode is in the second orientation.

6. The energy delivery device of claim 1, wherein the at least one ablation electrode extends partially around the expandable member in the second orientation position without extending completely around the expandable member.

7. The energy delivery device of claim 1, wherein the at least one electrode extends less than 360 degrees around the expandable member.

8. The energy delivery device of claim 1, wherein the at least one ablation electrode includes a plurality of ablation electrodes that fit entirely within the space between the adjacent cartilage rings of the airway in the second orientation.

9. The energy delivery device of claim 8, wherein the plurality of electrodes extend less than 360 degrees around the expandable member.

10. The energy delivery device of claim 1, wherein when the expandable member is in a partially expandable state the at least one ablation electrode is movable relative to the expandable member to both translate along the longitudinal axis relative to the expandable member and to rotate relative to the expandable member up to and past a vertical plane that is perpendicular to the longitudinal axis.

11. The energy delivery device of claim 1, wherein the at least one ablation electrode is positioned in a channel of the fluid delivery conduit.

12. The energy delivery device of claim 1, wherein the electrode is a rigid tube that at least partially defines the fluid delivery conduit.

13. The energy delivery device of claim 1, wherein the at least one ablation electrode is collapsible and expandable together with the fluid delivery conduit.

14. The energy delivery device of claim 1, wherein the fluid delivery conduit is in fluid communication with the expandable member to serially supply fluid from the fluid delivery conduit to the expandable member.

15. An energy delivery device, comprising:
a deployable element movable between a collapsed state and an expanded state; and
an energy emitter assembly including a fluid delivery conduit that curves circumferentially around at least a portion of the deployable element in the expanded state, and an electrode that extends along the fluid delivery conduit, and that is at least partially movable relative to an underlying surface of the deployable element, the electrode being moveable relative to the deployable element from a first position to a second position as the deployable element expands, the electrode extending a first distance along to a longitudinal axis of the energy delivery device in the first position and a second distance along to the longitudinal axis in the second position, the first distance being greater than the second distance,
wherein in the expanded state the deployable element is configured to urge the electrode to at least partially fit within an intercartilaginous space between adjacent cartilage rings of an airway wall of a bronchial tree, and
wherein the fluid delivery conduit is configured to cool the electrode in the second position.

16. The energy delivery device of claim 15, wherein the energy emitter assembly is movable from a delivery configuration when the deployable element is in the collapsed state to a deployed configuration when the deployable element is in the expanded state, and the deployable element in the expanded state is configured to press the energy emitter assembly against the airway wall at least partially within the intercartilaginous space.

17. The energy delivery device of claim 15, wherein the energy emitter assembly protrudes radially outward from the deployable element.

18. The energy delivery device of claim 15, wherein the electrode is configured to rotate about the longitudinal axis from the first position to the second position as the deployable element expands, and wherein a first dimension of the electrode is at a smaller angle relative to the longitudinal axis when in the first position than when in the second position.

19. The energy delivery device of claim 15, wherein the electrode is disposed in an imaginary plane that is transverse to the longitudinal axis when the deployable element is in the expanded state.

20. The energy delivery device of claim 15, wherein a portion of the energy emitter assembly is moveable relative to the underlying surface of the deployable element that directly underlies the portion of the energy emitter assembly when the energy emitter assembly is in the second position.

21. The energy delivery device of claim 15, wherein the electrode is configured to displace along the deployable element in a longitudinal direction of the deployable element a displacement distance that is at least half a distance between the adjacent cartilage rings.

22. The energy delivery device of claim 15, wherein the electrode extends axially adjacent to the deployable element in the first position and the electrode extends circumferentially around the deployable element in the second position.

23. The energy delivery device of claim 15, wherein the fluid delivery conduit forms a loop that extends at least partially around a circumference of the deployable element in a fully expanded state.

24. The energy delivery device of claim 15, further comprising a coolant source,
wherein the fluid delivery conduit is in fluid communication with an interior of the deployable element and the fluid delivery conduit is arranged relative to the deployable element such that coolant from the coolant source is supplied serially to the fluid delivery conduit and then the deployable element.

25. The energy delivery device of claim 15, wherein in the first position, the energy emitter assembly is sized to be held within a working channel of a bronchoscope.

26. The energy delivery device of claim 25, wherein in the first position, the energy emitter assembly has a maximum diameter of about 5 mm to 6 mm.

27. The energy delivery device of claim 25, wherein in the first position, the energy emitter assembly has a maximum diameter of about 2.8 mm to 3 mm.

* * * * *